(12) United States Patent
Harris et al.

(10) Patent No.: US 9,464,324 B2
(45) Date of Patent: Oct. 11, 2016

(54) METHODS OF DETERMINING THE PROGNOSIS OF AN ADENOCARCINOMA

(75) Inventors: Curtis C. Harris, Garrett Park, MD (US); Masahiro Seike, Tokyo (JP); Xin Wei Wang, Rockville, MD (US)

(73) Assignee: The United States of America as represented by the Secretary, DHHS, Washington, DC (US)

( * ) Notice: Subject to any disclaimer, the term of this patent is extended or adjusted under 35 U.S.C. 154(b) by 887 days.

(21) Appl. No.: 12/373,191

(22) PCT Filed: Jul. 16, 2007

(86) PCT No.: PCT/US2007/073637
§ 371 (c)(1),
(2), (4) Date: Jan. 9, 2009

(87) PCT Pub. No.: WO2008/009028
PCT Pub. Date: Jan. 17, 2008

(65) Prior Publication Data
US 2009/0258789 A1 Oct. 15, 2009

Related U.S. Application Data

(60) Provisional application No. 60/830,936, filed on Jul. 14, 2006, provisional application No. 60/885,101, filed on Jan. 16, 2007.

(51) Int. Cl.
*C12Q 1/68* (2006.01)

(52) U.S. Cl.
CPC ....... *C12Q 1/6886* (2013.01); *C12Q 2600/106* (2013.01); *C12Q 2600/112* (2013.01); *C12Q 2600/118* (2013.01); *C12Q 2600/136* (2013.01)

(58) Field of Classification Search
None
See application file for complete search history.

(56) References Cited

U.S. PATENT DOCUMENTS

| 6,613,883 B1 | 9/2003 | Harris et al. |
| 6,618,679 B2 | 9/2003 | Loehrlein et al. |
| 6,960,570 B2 | 11/2005 | Wang et al. |
| 7,049,063 B2 | 5/2006 | Wang et al. |
| 7,171,311 B2 | 1/2007 | Dai et al. |
| 2003/0153013 A1* | 8/2003 | Huang ............ 435/7.9 |
| 2003/0224374 A1 | 12/2003 | Dai et al. |
| 2004/0058340 A1 | 3/2004 | Dai et al. |
| 2004/0063120 A1 | 4/2004 | Beer et al. |
| 2004/0146907 A1 | 7/2004 | Smith |
| 2009/0215053 A1* | 8/2009 | Galon et al. ............ 435/6 |

FOREIGN PATENT DOCUMENTS

| EP | 05292200 | * 10/2005 |
| WO | WO 00/01419 A1 | 1/2000 |
| WO | WO 03/029273 A2 | 4/2003 |
| WO | WO 03/087766 A2 | 10/2003 |
| WO | WO 2004/041196 A2 | 5/2004 |
| WO | WO 2004/044178 A2 | 5/2004 |
| WO | WO 2004/074510 A1 | 9/2004 |
| WO | WO 2005/015236 A2 | 2/2005 |
| WO | WO2007140352 | * 5/2006 |
| WO | WO 2006/060653 A2 | 6/2006 |

OTHER PUBLICATIONS

Tibshirani et al (PNAS, 99:6567-6572, 2002, IDS, Jan. 12, 2009, p. 4, item 3 from bottom).*
Liang et al, WO2007140352, filed on May 26, 2006.*
Wislez et al , Inflamm Res 53: 4-12, 2004.*
Yuan et al, Amer J Res and Crit Care Med 162:1957-1963, 2000.*
Li et al, Lange Arch Surg 388:406-412, 2003.*
SaJi et al, Ann Thorac Cardiovasc Surg 9:295-300, 2003.*
Makino et al, Brit J Surgery 85:1658-62, 1998.*
Li et al Langenbeck Arch Surg 388:405-412, 2003.*
Fukuyama et al., "Cytokine Production of Lung Cancer Cell Lines: Correlation Between Their Production and the Inflammatory/Immunological Responses Both In Vivo and In Vitro," *Cancer Sci.* 98:1048-1054, 2007.
Gemma et al., "Altered Expression of Several Genes in Highly Metastatic Subpopulations of a Human Pulmonary Adenocarcinoma Cell Line," *Eur. J. Cancer* 37:1554-1561, 2001.
Ito et al., "Lung Carcinoma: Analysis of T Helper Type 1 and 2 Cells and T Cytotoxic Type 1 and 2 Cells by Intracellular Cytokine Detection with Flow Cytometry," *Cancer* 85:2359-2367, 1999.
Orditura et al., "Elevated Serum Levels of Interleukin-8 in Advanced Non-Small Cell Lung Cancer Patients: Relationship with Prognosis," *J. Interferon Cytokine Res.* 22:1129-1135, 2002.
Ramaswamy et al., "A Molecular Signature of Metastasis in Primary Solid Tumors," *Nature Genet.* 33:49-54, 2003, Epub Dec. 9, 2002.
AstraZeneca Pharmaceuticals LP , "Types of Lung Cancer," http://www.lungcancerinfo.net/content/types/, 2006.
The Thomas L. Petty Aspen Lung Conference, 2003 Annual Meeting, Jun. 4-7, 2003, Aspen, Colorado.
The Thomas L. Petty Aspen Lung Conference, 49th Annual Meeting, Jun. 7-10, 2006, Aspen, Colorado.
Asselin-Paturel et al., "Quantitative Analysis of Th1, Th2 and TGF-β1 Cytokine Expression in Tumor, TIL and PBL of Non-Small Cell Lung Cancer Patients," *Int. J. Cancer* 77:7-12, 1998.
Bair and Tibshirani, "Semi-Supervised Methods to Predict Patient Survival from Gene Expression Data," *PLoS Biol.* 2:511-522, 2004.

(Continued)

*Primary Examiner* — Lei Yao
(74) *Attorney, Agent, or Firm* — Klarquist Sparkman, LLP

(57) ABSTRACT

Methods are disclosed for determining the prognosis of a subject with an adenocarcinoma in an organ, such as the lung. The methods can include quantitating expression of a plurality of cytokines of interest, such as IL-1a, IL-1b, IL-2, IL-8, IL-10, IL-12, IL-15, IFN-γ and TNF-a in the adenocarcinoma and in non-cancerous tissue in the organ. Altered expression of IL-1a, IL-1b, IL-2, IL-8, IL-10, IL-12, IL-15, IFN-γ and TNF-a in the adenocarcinoma as compared to a control and in non-cancerous tissue in the organ as compared to a control determines the prognosis for the subject. Methods for determining if a therapeutic agent is effective as an anti-cancer agent are also disclosed.

17 Claims, 10 Drawing Sheets

(56) References Cited

OTHER PUBLICATIONS

Beer et al., "Gene-Expression Profiles Predict Survival of Patients with Lung Adenocarcinoma," *Nature Med.* 8:816-824, 2002.
Bertomeu et al., "Interleukin 1-Induced Cancer Cell/Endothelial Cell Adhesion In Vitro and Its Relationship to Metastasis In Vivo: Role of Vessel Wall 13-HODE Synthesis and Integrin Expression," *Clin. Exp. Metastasis* 11:243-250, 1993.
Bhattacharjee et al., "Classification of Human Lung Carcinomas by mRNA Expression in Profiling Reveals Distinct Adenocarcinoma Subclasses," *Proc. Natl. Acad. Sci. USA* 98:13790-13795, 2001.
Cabanes et al., "Enhancement of Antitumor Activity of Polyethylene Glycol-coated Liposomal Doxorubicin with Soluble and Liposomal Interleukin 2," *Clin. Cancer Res.* 5:687-693, 1999.
Chen et al., "Global Analysis of Gene Expression in Invasion by a Lung Cancer Model," *Cancer Res.* 61:5223-5230, 2001.
Dennis et al., "Markers of Adenocarcinoma Characteristics of the Site of Origin: Development of a Diagnostic Algorithm," *Clin. Cancer Res.* 11:3766-3772, 2005.
Eifuku et al., "Heterogeneous Response Patterns of Alveolar Macrophages from Patients with Lung Cancer by Stimulation with Interferon-$\gamma$," *Jpn. J. Clin. Oncol.* 30:295-300, 2000.
Elaraj et al., "The Role of Interleukin 1 in Growth and Metastasis of Human Cancer Xenografts," *Clin. Cancer Res.* 12:1088-1096, 2006.
Endoh et al., "Prognostic Model of Pulmonary Adenocarcinoma by Expression Profiling of Eight Genes as Determined by Quantitative Real-Time Reverse Transcriptase Polymerase Chain Reaction," *J. Clin. Oncol.* 22:811-819, 2004.
Garber et al., "Diversity of Gene Expression in Adenocarcinoma of the Lung," *Proc. Natl. Acad. Sci. USA* 98:13784-13789, 2001.
Gordon et al., "A Prognostic Test for Adenocarcinoma of the Lung From Gene, Expression Profiling Data," *Cancer Epidemiol. Biomarkers Prevent.* 12:905-910, 2003.
Guo et al., "Constructing Molecular Classifiers for the Accurate Prognosis of Lung Adenocarcinoma," *Clin. Cancer Res.* 12:3344-3354, 2006.
Haku et al., "Interleukin-12-Mediated Killer Activity in Lung Cancer Patients," *Cytokine* 9:846-852, 1997.
Hardiman, "Microarray Technologies 2003—An Overview," *Pharmacogenomics* 4:251-256, 2003.
Harris, "Microenvironment and Cancer: Inflammation and MicroRNA," Abstract for Aspen Cancer Conference, 2006.
Kuninaka et al., "Direct Influences of Pro-Inflammatory Cytokines (IL-1$\beta$, TNF-$\alpha$, IL-6) on the Proliferation and Cell-Surface Antigen Expression of Cancer Cells," *Cytokine* 12:8-11, 2000.
Meazza et al., "Gene Transfer of a Secretable Form of IL-15 in Murine Adenocarcinoma Cells: Effects on Tumorigenicity, Metastatic Potential and Immune Response," *Int. J. Cancer* 87:574-581, 2000.
Miura et al., "Laser Capture Microdissection and Microarray Expression Analysis of Lung Adenocarcinoma Reveals Tobacco Smoking- and Prognosis-related Molecular Profiles," *Cancer Res.* 62:3244-3250, 2002.
Narasimhan, "Prediction Analysis of Microarrays in Excel," Proceedings of the $3^{rd}$ International Workshop on Distributed Statistical Computing (DSC 2003), Mar. 20-22, 2003, Vienna, Austria.
Ohshima et al., "Differential Chemokine, Chemokine Receptor, Cytokine and Cytokine Receptor Expression in Pulmonary Adenocarcinoma: Diffuse Down-Regulation is Associated with Immune Evasion and Brain Metastasis," *Int. J. Oncol.* 23:965-973, 2003.
Saji et al., "Significance of Expression of TGF-$\beta$ in Pulmonary Metastasis in Non-small Cell Lung Cancer Tissues," *Ann. Thorac. Cardiovasc. Surg.* 9:295-300, 2003.
Segal et al., "From Signatures to Models: Understanding Cancer Using Microarrays," *Nature Genet.* 37:S38-S45, 2005.
Seike et al., "Proteomic Signature of Human Cancer Cells," *Proteomics* 4:2776-2788, 2004.
Seike et al., "Use of a Cytokine Gene Expression Signature in Lung Adenocarcinoma and the Surrounding Tissue as a Prognostic Classifier," *J. Natl. Cancer Inst.* 99:1257-1269, 2007.
Soria et al., "Lack of Interleukin-10 Expression Could Predict Poor Outcome in Patients with Stage I Non-Small Cell Lung Cancer," *Clin. Cancer Res.* 9:1785-1791, 2003.
Takada et al., "Prediction of Lymph Node Metastasis by Analysis of Gene Expression Profiles in Non-Small Cell Lung Cancer," *J. Surg. Res.* 122:61-69, 2004.
Tibshirani et al., "Diagnosis of Multiple Cancer Types by Shrunken Centroids of Gene Expression," *Proc. Natl. Acad. Sci. USA* 99:6567-6572, 2002.
Tibshirani et al., "Prediction Analysis of Microarrays for R: Installation Guide and Manual," http://www-stat.stanford.edu/%7Etibs/PAM/Rdist/doc/readme.html, 2006.
Tran et al., "Prognostic Significance of Tumor Necrosis Factors and Their Receptors in Nonsmall Cell Lung Carcinoma," *Cancer* 83:276-282, 1998.
Wigle et al., "Molecular Profiling of Non-Small Cell Lung Cancer and Correlation with Disease-free Survival," *Cancer Res.* 62:3005-3008, 2002.
Yamazaki et al., "Clinical Significance of Serum $T_H1/T_H2$ Cytokines in Patients With Pulmonary Adenocarcinoma," *Surgery* 131:S236-S241, 2002.
Yanaihara et al., "Unique MicroRNA Molecular Profiles in Lung Cancer Diagnosis and Prognosis," *Cancer Cell* 9:189-198, 2006.
Yuan et al., "Interleukin-I Messenger Ribonucleic Acid Expression Correlates with Tumor Progression, Tumor Angiogenesis, Patient Survival, and Timing of Relapse in Non-Small-Cell Lung Cancer," *Am. J. Respir. Crit. Care Med.* 162:1957-1963, 2000.
US 6,512,094, 01/2003, Xu et al. (withdrawn)

* cited by examiner

Step 1. Biopsy patient with lung adenocarcinoma

Non-cancerous tissue (N)  Tumor tissue (T)

Step 2. Profile samples (N) and (T) by real time quantitative RT-PCR

<Data N>  <Data T>

|         | Patient A |
|---------|-----------|
| IL-1a   | 1.33      |
| IL-1b   | 2.02      |
| IL-2    | 0.76      |
| IL-8    | 0.25      |
| IL-10   | 0.22      |
| IL-12p35| 0.48      |
| IL-15   | 1.26      |
| IFNr    | 7.01      |
| TNFa    | 0.74      |
| CSF1    | 0.57      |
| IL-6    | 1.04      |

Export the CLASS-11 data as a excel table

|         | Patient A |
|---------|-----------|
| IL-1a   | 0.25      |
| IL-1b   | 0.96      |
| IL-2    | 1.53      |
| IL-8    | 0.04      |
| IL-10   | 0.20      |
| IL-12p35| 1.68      |
| IL-15   | 1.28      |
| IFNr    | 5.66      |
| TNFa    | 0.62      |
| CSF1    | 0.42      |
| IL-6    | 0.02      |

Step 3. Assign the patient by the two classifiers* provided using PAM

*Two classifiers are based on the expression of 11-cytokine genes in 80 adenocarcinoma cases Step 4. Final prognostic decision FIG. 7A
FIG. 7B
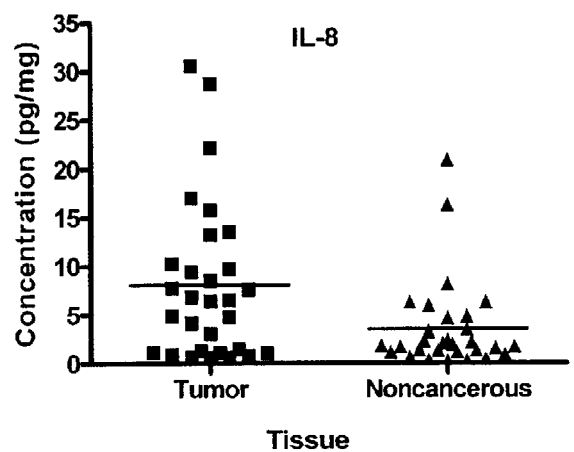
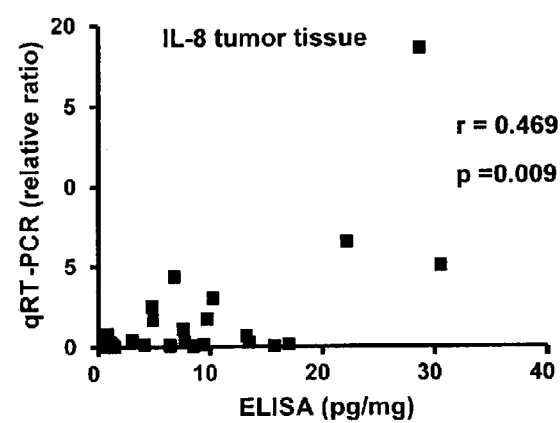
FIG. 7C
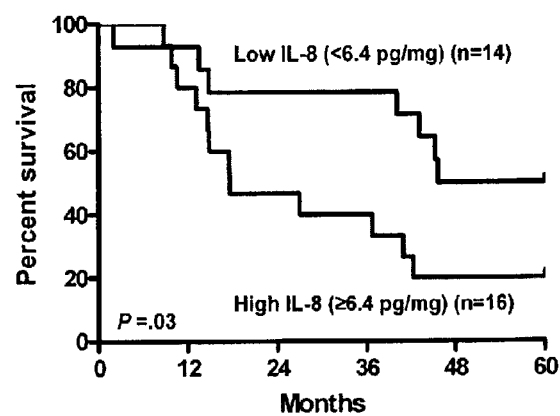

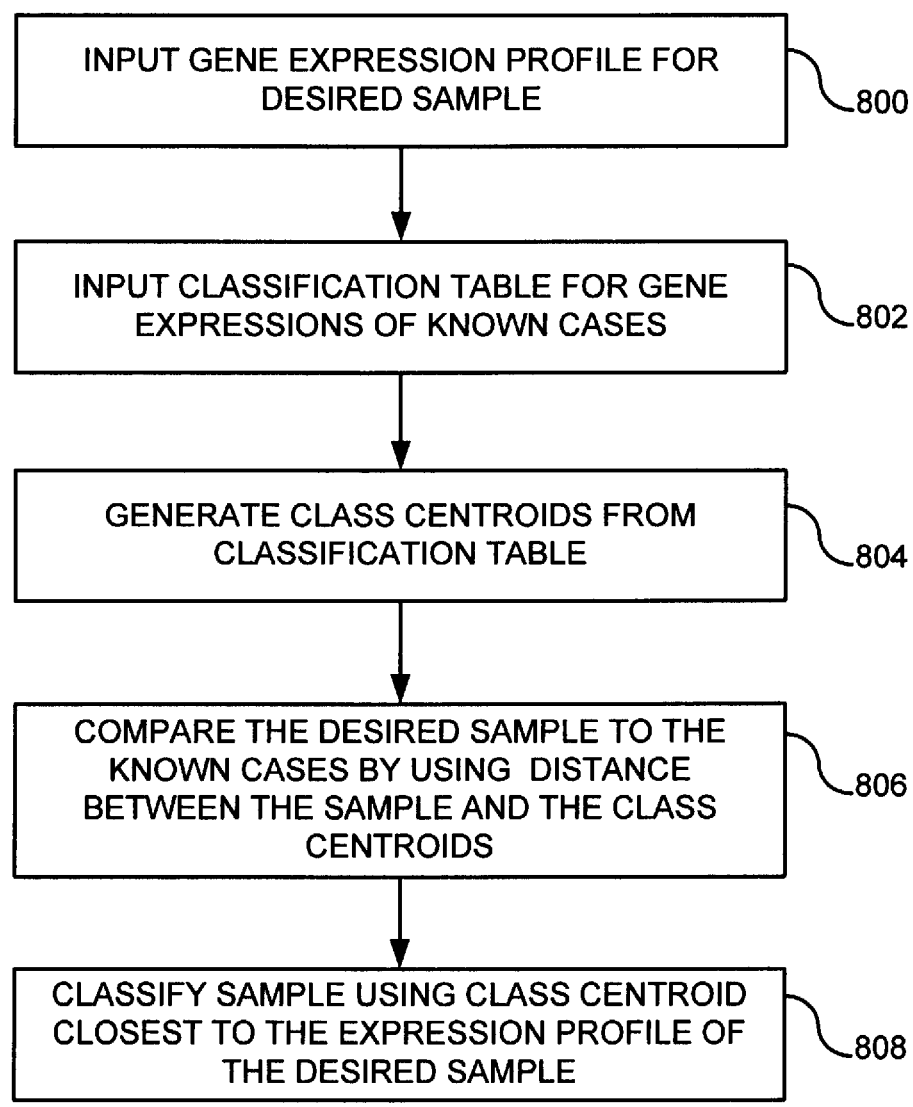

METHODS OF DETERMINING THE PROGNOSIS OF AN ADENOCARCINOMA

CROSS-REFERENCE TO RELATED APPLICATIONS

This is the U.S. National Stage of International Application No. PCT/US2007/073637, filed Jul. 16, 2007, which was published in English under PCT Article 21(2), which in turn application claims the benefit of U.S. Provisional Application Nos. 60/830,936, filed Jul. 14, 2006 and 60/885,101 filed Jan. 16, 2007, both herein incorporated by reference.

FIELD

This relates to the field of cancer, specifically to methods for determining the prognosis of an adenocarcinoma, as well as arrays and kits that can be used for such methods.

BACKGROUND

Cancer is a class of disease characterized by uncontrolled division of cells and the ability of these cells to invade other tissues, either by direct growth into adjacent tissue of by implantation into distant sites via metastasis. Cancer affects people at all ages, but risk tends to increase with age. Cancer is a leading cause of death in developed countries. Adenocarcinoma is one form of cancer that originates in glandular tissues and/or has secretory properties. Adenocarcinomas can originate in many different tissues, such as the lung, breast, prostate, colon, stomach, pancreas, and cervix.

Lung cancer is the leading cause of cancer deaths in the United States, among both men and women. It is now the most common form of cancer diagnosed in the United States and a major cause of death. Lung cancer accounts for 14% of all cancers and 28% of all cancer deaths. The American Cancer Society estimates annual lung cancer deaths in the United States at about 163,510 in 2005 (Jemal et al., *CA Cancer J. Clin.* 55:10-30, 2005).

Lung cancers are divided into two general groups: small cell and non-small cell lung cancer. Small cell lung cancer spreads aggressively and accounts for about 20 percent of lung cancers in the United States. Non-small cell lung cancer accounts for the remaining 80 percent of lung cancers. There are three major categories of non-small cell lung cancer (NSCLC): (i) squamous cell carcinoma; (ii) adenocarcinoma; and (iii) large cell carcinoma. Adenocarcinoma is the predominant histological subtype of NSCLC (Devesa et al., *Int. J. Cancer* 117:294-9, 2005). Even when curative resection of early-stage NSCLC on a patient is performed, the risk of developing metastasis remains substantial. Lymph node metastasis and distant metastases through lymph and blood flow frequently occur and prove fatal; the 5-year survival rate of patients in pathological stage IA and IB are only 67% and 57%, respectively (Mountain, *Cell* 100:57-70, 2000).

Several mRNA and microRNA microarray-based studies have demonstrated that there can be unique molecular profiles of tumor tissues associated with metastasis and survival. However, a need remains for a set of markers that can be used to determine the prognosis of a subject, or that can be used to determine if NSCLC will metastasize.

Intensive research on prevention, causes, diagnosis and treatment of adenocarcinomas, such as lung cancer, is ongoing. In spite of this considerable research, patients' lung cancers are often in advanced stages at the time of detection, and current therapies, which are generally based on a combination of chemotherapy or surgery and radiation, continue to prove inadequate in many patients. Consequently, new methods to prevent, diagnose and treat lung cancer are needed.

SUMMARY

There is a need to determine the prognosis of subject with an adenocarcinoma. For example, the determination of the prognosis can lead a medical professional to select a specific therapeutic regimen or can provide information that is of benefit to a patient. For example, if it is determined that a subject has a poor prognosis, a more aggressive therapeutic method can be used to treat the subject. If it is determined that the subject has a good prognosis, then a less aggressive therapeutic strategy could be pursued. It is also of interest to determine if a therapeutic strategy is likely to be effective in a subject with an adenocarcinoma.

The inventors have identified a cytokine gene signature that can be used to determine the lymph node status and prognosis of a subject having adenocarcinoma, such as lung adenocarcinoma. The cytokine gene signature, referred to as the Cytokine Lung Adenocarcinoma Survival Signature of 11 genes (CLASS-11), accurately classifies patients according to risk of death from adenocarcinoma, including stage I disease. The cytokine gene signature of noncancerous lung tissue primarily reflected the lymph node status, whereas the gene signature of the corresponding lung tumor tissue was associated with prognosis independent of lymph node status. CLASS-11 prognostic classification was statistically significantly associated with survival and was an independent prognostic factor for stage I patients (hazard ratio for death in the high risk CLASS-11 group compared with the low risk CLASS-11 reference group=7.46, 95% confidence interval=2.14 to 26.05; P=0.002). Therefore, the disclosed methods and arrays can be used to identify stage I lung adenocarcinoma patients who have good or poor prognosis.

Methods are provided for determining the prognosis of a subject having an adenocarcinoma in an organ. In particular examples, the method includes measuring expression of a plurality of cytokines of interest in the adenocarcinoma and in non-cancerous tissues in the organ, wherein the cytokines of interest consist essentially of interleukin (IL)-1a, IL-1b, IL-2, IL-6, IL-8, IL-10, IL-12, IL-15, colony stimulating factor (CSF)-1, interferon (IFN)-γ and tumor necrosis factor (TNF)-a. In some examples, expression levels are quantitated. The expression of IL-1a, IL-1b, IL-2, IL-6, IL-8, IL-10, IL-12, IL-15, CSF-1, IFN-γ and TNF-a in the adenocarcinoma and in the non-cancerous tissue can be compared to a control, or not. Exemplary controls include reference values of cytokine expression for known subjects (e.g. Tables 1-4), which can be raw values or values normalized to a disease-free normal individual, and cytokine expression values from a disease-free normal individual. Altered expression of at least two of IL-1a, IL-1b, IL-2, IL-6, IL-8, IL-10, IL-12, IL-15, CSF-1, IFN-γ and TNF-a in the adenocarcinoma and in the non-cancerous tissue (for example as compared to the control) can indicate the prognosis for the subject. In particular examples, increased expression of at least IL-8 and TNF-a indicates poor prognosis. In particular examples, the cytokine expression values are classified using an algorithm (such as PAM), which provides an output of metastasis and prognosis, such as an output indicating a low or high risk of death within the next 5 years. In some examples, the algorithm compares the cytokine expression values to control values for known cases (such as Tables 1-2 or 3-4).

Methods are also provided for evaluating the effect of an anti-cancer agent in a mammalian subject with an adenocarcinoma in an organ. The method can include obtaining a first sample of the adenocarcinoma and a first sample of a non-cancerous tissue from the organ of the subject prior to administration of the anti-cancer agent. Expression of a plurality of cytokines of interest is evaluated in the first sample of the adenocarcinoma and the first sample of the noncancerous tissue, wherein the cytokines of interest consist essentially of IL-1a, IL-1b, IL-2, IL-6, IL-8, IL-10, IL-12, IL-15, CSF-1, IFN-γ and TNF-a. The agent is then administered to the mammalian subject. A second sample of the adenocarcinoma and a sample of a noncancerous tissue is obtained from the organ of the subject following administration of the agent to the mammalian subject. The expression of a plurality of cytokines of interest is evaluated in the second sample of the adenocarcinoma and the second sample of the noncancerous tissue, wherein the cytokine of interest consist essentially of IL-1a, IL-1b, IL-2, IL-6, IL-8, IL-10, IL-12, IL-15, CSF-1, IFN-γ and TNF-a. Altered expression of at least two of IL-1a, IL-1b, IL-2, IL-6, IL-8, IL-10, IL-12, IL-15, CSF-1, IFN-γ and TNF-a in the first samples as compared to the second samples in the organ determines if the anti-cancer agent is effective.

Also provided are arrays that include probes specific for essentially IL-1a, IL-1b, IL-2, IL-6, IL-8, IL-10, IL-12, IL-15, CSF-1, IFN-γ and TNF-a. Such an array can further include control sequences, and in particular examples does not include more than 1-5 additional cytokine sequences (such as probes that are specific for 1, 2, 3, 4, or 5 additional cytokines).

The foregoing and other features will become more apparent from the following detailed description of several embodiments, which proceeds with reference to the accompanying figures.

BRIEF DESCRIPTION OF THE FIGURES

FIGS. 7A-7C are graphs showing the correlation between IL-8 expression as measured by qRT-PCR and ELISA. (A) Protein concentrations for IL-8 of tumor tissue and noncancerous tissue in 30 lung adenocarcinoma patients. Median values of tumor tissue and noncancerous tissue were marked by lines (6.45 and 1.89, respectively). (B) Spearmen's correlation analysis of gene expression by qRT-PCR and protein concentrations by ELISA for IL-8 in tumor tissue (Spearman's rho=0.47, P=0.009). (C) The thirty patients were divided into two groups by the median value in tumor tissue. Kaplan-Meier survival curve between cases with high-IL-8 (≥6.4 pg/mg) (n=16) and low-IL-8 levels (<6.4 pg/mg) in tumor tissue (n=14) (P=0.03). P-value was calculated by the COX-Mantel log-rank test and statistical significance was considered to be <0.05.

FIG. 9 is a more detailed flowchart of a method used by the class prediction software of FIG. 8.

DETAILED DESCRIPTION

I. Abbreviations

Figure 1A:
FIGS. 1A-1B is a schematic representation of a particular example of how the disclosed methods can be practiced.
Figure 1A:
Figure 1A:
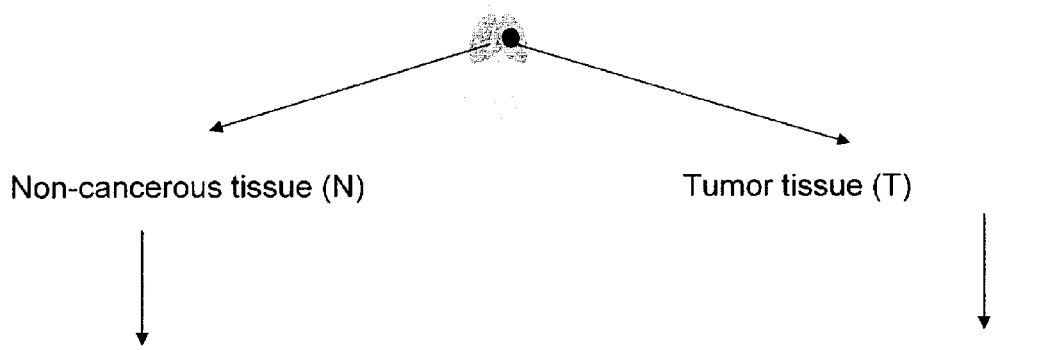

ANAX1: annexin 1
CSF: colony stimulating factor

ELISA: enzyme linked immunosorbent assay
HCC: hepatocellular carcinoma
HLA: human leukocyte antigen
IFN: interferon
IL: interleukin
NSCLC: non-small cell lung cancer
PAM: predication analysis of microarrays
PRG: platelet proteoglycan
qRT-PCR: quantitative real time reverse transcriptase PCR
RIA: radioimmuno assay
SELDI-TOF: surface-enhanced laser desorption-ionization time-of-flight
TNF: tumor necrosis factor
TNM: Tumor-Node-Metastasis II. Terms Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). All GenBank Accession Nos. are those sequences available as of Jan. 16, 2007.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Adenocarcinoma: Carcinoma derived from glandular tissue or in which the tumor cells form recognizable glandular structures. Adenocarcinomas can be classified according to the predominant pattern of cell arrangement, as papillary, alveolar, etc., or according to a particular product of the cells, as mucinous adenocarcinoma. Adenocarcinomas arise in several tissues, including the kidney, breast, colon, cervix, esophagus, gastric, pancreas, prostate, and lung.

Adjuvant Therapy (for cancer): The administration of an additional therapy or therapeutic regiment, such as chemotherapy or radiation, following the surgical resection of a cancer, such as an adenocarcinoma.

Administration: To provide or give a subject an agent, such as an anti-neoplastic chemotherapeutic agent, by any effective route. Exemplary routes of administration include, but are not limited to, oral, injection (such as subcutaneous, intramuscular, intradermal, intraperitoneal, and intravenous), sublingual, rectal, transdermal, intranasal, vaginal and inhalation routes.

Amplifying a nucleic acid molecule: To increase the number of copies of a nucleic acid molecule, such as a gene or fragment of a gene, for example a region of a gene encoding a cytokine. The resulting products are called amplification products.

An example of in vitro amplification is the polymerase chain reaction (PCR), in which a biological sample obtained from a subject (such as a sample containing tumor cells or cells for adjacent non-cancerous tissue) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time RT-PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Annexin A1 (ANXA1): A molecule that belongs to a family of $Ca^{2+}$-dependent phospholipid binding proteins which have a molecular weight of approximately 35,000 to 40,000 and are preferentially located on the cytosolic face of the plasma membrane. Native annexin I protein has an apparent relative molecular mass of 40 kDa, with phospholipase A2 inhibitory activity. Annexin I may have anti-inflammatory activity.

ANXA1 sequences are publicly available. For example, GENBANK® Accession number NC_000009.10 discloses a human ANXA1 gene sequence, and GENBANK® Accession numbers NM_000700.1 and NP_000691 disclose human ANXA1 mRNA and protein sequences, respectively. One skilled in the art will appreciate that ANXA1 nucleic acid and protein molecules can vary from those publicly available, such as those having one or more substitutions, deletions, insertions, or combinations thereof, while still retaining ANXA1 biological activity.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-100 addressable locations, such as 5-50 addressable locations. In particular examples, an array consists essentially of probes or primers (such as those that permit amplification) specific for IL-1a, IL-1b, IL-2, IL-6, IL-8, IL-10, IL-12, IL-15, CSF-1, IFN-γ and TNF-a.

In particular examples, an array includes nucleic acid molecules, such as oligonucleotide sequences that are at least 15 nucleotides in length, such as about 15-40 nucleotides in length Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to at least nine different cytokines.

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. For example a probe or primer specific for a nucleic acid molecule encoding a cytokine can stably bind to the nucleic acid molecule encoding the cytokine.

Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Cancer: Malignant neoplasm that has undergone characteristic anaplasia with loss of differentiation, increase rate of growth, invasion of surrounding tissue, and is capable of metastasis. In cancer treatment, "chemotherapy" or "administration of an anti-cancer agent" refers to the administration of one or a combination of compounds or physical processes (such as irradiation) to kill or slow the reproduction of rapidly multiplying cells. Anti-neoplastic chemotherapeutic agents include those known by those skilled in the art, including, but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. "Chemotherapy-resistant disease" is a cancer that is not significantly responsive to administration of one or more chemotherapeutic agents. A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

cDNA (complementary DNA): A piece of DNA lacking internal, non-coding segments (introns) and regulatory sequences which determine transcription. cDNA can be synthesized by reverse transcription from messenger RNA extracted from cells.

Cytokine/Interleukin (IL): A generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many growth factors and cytokines act as cellular survival factors by preventing programmed cell death. Cytokines and interleukins include both naturally occurring peptides and variants that retain full or partial biological activity. Although specific cytokines/interleukins are described in the specification, they are not limited to the specifically disclosed sequences.

Colony-Stimulating Factor 1 (CSF-1): A cytokine also known as macrophage colony-stimulating factor. At least four different transcript variants encoding three different isoforms of CSF-1 are known. The human gene for CSF-1 maps to chromosome 1p21-p13 and has 9 exons spanning approximately 19 kb. It is understood that CSF-1 includes both naturally occurring and recombinant CSF-1 peptides, as well as CSF-1 fragments and CSF-1 variants that retain full or partial CSF-1 biological activity.

CSF-1 is produced by macrophages/monocytes, fibroblasts, epithelial, and endothelial cells. It promotes the proliferation, differentiation, and survival of macrophages. It also induces secretion of cytokines and proteases by macrophages. In addition, CSF-1 promotes differentiation and proliferation of osteoclast progenitors.

CSF-1 sequences are publicly available. For example, GENBANK® Accession number NC_000001.9 discloses a human CSF-1 gene sequence, and GENBANK® Accession numbers NM_000757.3, NM_172211.1, NM_172212.1, and NM_172210.1 disclose known transcript variants of human CSF-1 mRNA sequences. GENBANK® Accession numbers NP_000748, NP_757350, NP_757351, and NP_757349 disclose known isoforms of human CSF-1 protein sequences. One skilled in the art will appreciate that CSF-1 nucleic acid and protein molecules can vary from those publicly available, such as those having one or more substitutions, deletions, insertions, or combinations thereof, while still retaining CSF-1 biological activity.

DNA (deoxyribonucleic acid): A long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Differential expression or altered expression: A difference, such as an increase or decrease, in the conversion of the information encoded in a gene (such as a cytokine gene) into messenger RNA, the conversion of mRNA to a protein, or both. In some examples, the difference is relative to a control or reference value, such as an amount of gene expression in tissue not affected by a disease, such as an adenocarcinoma (for example lung cancer), from the same subject, or an amount expected in a different subject who does not have an adenocarcinoma (such as lung cancer). The difference can also be in a non-cancerous tissue from a subject (that has the cancer in the same organ) as compared to tissue from a different subject not afflicted with the adenocarcinoma. Detecting differential expression can include measuring a change in gene or protein expression, such as a change in expression of one or more cytokine genes or proteins. See also, "downregluated" and "upregulated," below.

Downregulated or decreased: When used in reference to the expression of a nucleic acid molecule (such as a cytokine nucleic acid molecule), such as a gene, refers to any process which results in a decrease in production of a gene product. A gene product can be RNA (such as mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In several examples, a control is a relative amount of gene expression or protein expression in one or more subjects who do not have a specific adenocarcinoma, such as the relative amount of gene expression or protein expression in "cancer-free" subjects who do not have any known cancer.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule (such as a nucleic acid encoding a cytokine) can be altered relative to a normal (wild type) nucleic acid molecule. Alterations in gene expression, such as differential expression, includes but is not limited to: (1) overexpression; (2) underexpression; or (3) suppression of expression. Alternations in the expression of a nucleic acid molecule can be associated with, and in fact cause, a change in expression of the corresponding protein.

Protein expression (such as expression of a cytokine) can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have an adenocarcinoma) as well as laboratory values, even though possibly arbitrarily set. Laboratory standards and values may be set based on a known or determined population value and can be supplied in the format of a graph or table that permits comparison of measured, experimentally determined values.

Gene expression profile (or fingerprint): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 3, at least 4, at least 5, at least 9, at least 10, at least 11, or at least 15. A gene expression profile (also referred to as a fingerprint) can be linked to a tissue or cell type (such as lung tissue), to a particular stage of normal tissue growth or disease progression (such as adenocarcinoma), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have the cancer of interest). In one example, a gene expression profile in a subject is read on an array (such as a nucleic acid or protein array).

HLA-DPA1: A molecule of the human major histotocompatability complex. HLA-DPA1 sequences are publicly available. For example, GENBANK® Accession number NC_000006.10 discloses a human HLA-DPA1 gene sequence, and GENBANK® Accession numbers NM_033554.2 and NP_291032 disclose human HLA-DPA1 mRNA and protein sequences, respectively. One skilled in the art will appreciate that HLA-DPA1 nucleic acid and protein molecules can vary from those publicly available, such as those having one or more substitutions, deletions, insertions, or combinations thereof, while still retaining HLA-DPA1 biological activity.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

In particular examples, probes or primers can hybridize to one or more cytokine molecules (such as mRNA or cDNA molecules), for example under very high or high stringency conditions.

The following is an exemplary set of hybridization conditions and is not limiting:

| Very High Stringency (detects sequences that share at least 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share at least 80% identity) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share at least 50% identity) | |
| Hybridization: | 6x SSC at RT to 55° C. for 16-20 hours |
| Wash at least twice: | 2x-3x SSC at RT to 55° C. for 20-30 minutes each. |

Interferons: A family of more than 15 related proteins with three major classes ($\alpha$, $\beta$, and $\gamma$). Viruses are the prototypic inducer of interferon production. Interferons are pleiotropic cellular modulators which induce expression of a wide variety of genes including, but not limited to, chemokines, adhesion proteins, intracellular enzymes, and transcription factors.

Interferon-gamma (IFN-$\gamma$): A member of the interferon family. In vivo, interferon-$\gamma$ is a cytokine that is a dimeric protein glycosylated at two sites with subunits of 146 amino acids, and functional variants thereof. Murine and human IFN-$\gamma$ have approximately 40% sequence homology at the protein level. The human IFN-$\gamma$ gene is approximately 6 kb, contains four exons and maps to chromosome 12. At least six different variants of naturally occurring IFN-$\gamma$ have been described, and differ from each other by variable lengths of the C-terminal ends. IFN-$\gamma$ includes both naturally occurring and recombinant peptides, as well as IFN-$\gamma$ fragments and variants that retain full or partial IFN-$\gamma$ biological activity.

In T helper cells (Th cells) IL2 induces the synthesis of IFN-$\gamma$ and other cytokines. IFN-$\gamma$ also stimulates the expression of Ia antigens on the cell surface, the expression of CD4 in T helper cells, and the expression of high-affinity receptors for IgG in myeloid cell lines, neutrophils, and monocytes.

IFN-$\gamma$ sequences are publicly available. For example, GENBANK® Accession number NC_000012.10 discloses a human IFN-$\gamma$ gene sequence, and GENBANK® Accession numbers NM_000619.2 and NP_000610 disclose human IFN-$\gamma$ mRNA and protein sequences, respectively. One skilled in the art will appreciate that IFN-$\gamma$ nucleic acid and protein molecules can vary from those publicly available, such as those having one or more substitutions, deletions, insertions, or combinations thereof, while still retaining IFN-$\gamma$ biological activity.

IL-1a: A cytokine that is produced mainly by mononuclear and epithelial cells in response to infection or injury. It induces fever and activation of T-cells and macrophages. IL-1a activates a wide variety of genes involved in the acute phase response, including, but not limited to, other cytokines and cytokine receptors, inflammatory mediators (such as nitric oxide synthase), growth factors (such as fibroblast growth factor, keratinocyte growth factor, and insulin-like growth factor), clotting agents, extracellular matrix molecules, and oncogenes.

In vivo, IL-1a is a cytokine that is found as an 18 kDa monomeric protein of 159 amino acids, and functional variants thereof. Human and murine IL-1a share approximately 62% identity at the amino acid level. Human IL-1a and IL-1b have approximately 22% homology to one another. The gene for IL-1a is localized to chromosome 2q14 and spans approximately 12 kb with 7 exons. IL-1a includes both naturally occurring and recombinant peptides, as well as IL-1a fragments and variants that retain full or partial biological activity.

IL-1a sequences are publicly available. For example, GENBANK® Accession number NC_000002.10 discloses a human IL-1a gene sequence, and GENBANK® Accession numbers NM_000575.3 and NP_000566 disclose human IL-1a mRNA and protein sequences, respectively. One skilled in the art will appreciate that IL-1a nucleic acid and protein molecules can vary from those publicly available, such as those having one or more substitutions, deletions, insertions, or combinations thereof, while still retaining IL-1a biological activity.

IL-1b: A cytokine with activities very similar to that of IL-1a. Despite their relatively low homology, they bind to and activate the same receptors. A difference between IL-1a and IL-1b is that IL-1b is not active until its precursor molecule is cleaved and secreted from monocytes, while the precursor form of IL-1a is active and remains intracellular.

In vivo, IL-1b is a cytokine that is found as a monomeric protein of 17 kDa, having a length of 153 amino acids, and functional variants thereof. Human IL-1a and IL-1b have approximately 22% identity. Human and murine IL-1b share approximately 69% identity at the amino acid level. The gene encoding IL-1b maps to chromosome 2q14, spanning approximately 7 kb and having 7 exons. IL-1b includes both naturally occurring and recombinant peptides, as well as IL-1b fragments and variants that retain full or partial biological activity.

IL-1b sequences are publicly available. For example, GENBANK® Accession number NC_000002.10 discloses a human IL-1b gene sequence, and GENBANK® Accession numbers NM_000576.2 and NP_000567 disclose human IL-1b mRNA and protein sequences, respectively. One skilled in the art will appreciate that IL-1b nucleic acid and protein molecules can vary from those publicly available, such as those having one or more substitutions, deletions, insertions, or combinations thereof, while still retaining IL-1b biological activity.

IL-2: A cytokine that is produced by activated T-cells. It acts primarily as a T-cell growth factor, but B-cells, natural killer cells, and lymphokine-activated killer cells also respond to IL-2.

IL-2 is found in vivo as a 15 kDa glycoprotein having 153 amino acids, and functional variants thereof. Human and murine IL-2 are approximately 63% identical at the amino acid level. The human IL-2 gene maps to chromosome 4q26-q27 and contains 4 exons, spanning approximately 5 kb. IL-2 includes both naturally occurring and recombinant peptides, as well as IL-2 fragments and variants that retain full or partial biological activity.

IL-2 sequences are publicly available. For example, GENBANK® Accession number NC_000004.10 discloses a human IL-2 gene sequence, and GENBANK® Accession numbers NM_000586.2 and NP_000577 disclose human IL-2 mRNA and protein sequences, respectively. One skilled in the art will appreciate that IL-2 nucleic acid and protein molecules can vary from those publicly available, such as those having one or more substitutions, deletions, insertions, or combinations thereof, while still retaining IL-2 biological activity.

IL-6: A cytokine having numerous biological activities, which is demonstrated by the many acronyms under which IL6 has been described. For example, IL-6 is also known in the art as interferon, beta 2 (IFNβ2). IL6 is a pro-inflammatory cytokine secreted by T cells and macrophages that influences antigen-specific immune responses and inflammatory reactions.

IL-6 is found in vivo in humans as a protein of 185 amino acids glycosylated at amino acids 73 and 172, and is synthesized as a precursor protein of 212 amino acids. Murine and human IL-6 show 65% sequence homology at the DNA level and 42% homology at the protein level. The human IL-2 gene maps to chromosome 7p21 and contains 5 exons, spanning approximately 5 kb. IL-6 includes both naturally occurring and recombinant peptides, as well as IL-6 fragments and variants that retain full or partial biological activity.

IL-6 sequences are publicly available. For example, GENBANK® Accession number AF372214.2 discloses a human IL-6 gene sequence, and GENBANK® Accession numbers BC015511.1 and AAH15511.1 disclose human IL-6 mRNA and pre-protein sequences, respectively. One skilled in the art will appreciate that IL-6 nucleic acid and protein molecules can vary from those publicly available, such as those having one or more substitutions, deletions, insertions, or combinations thereof, while still retaining IL-6 biological activity.

IL-8: A cytokine that is produced by a variety of cells, such as T-cells, monocytes, neutrophils, fibroblasts, and endothelial cells in response to infection or inflammatory stimuli. IL-8 is a potent activator of neutrophils, which follow the IL-8 concentration gradient to the site of infection or inflammation.

IL-8 is found in vivo as a monomeric protein of approximately 8 kDa, and functional variants thereof. At least four forms of IL-8 exist, having 79, 77, 72, and 69 amino acids. IL-8 is a member of the CXC chemokine superfamily. The gene encoding IL-8 maps to chromosome 4q13-q21, and consists of 4 exons spanning approximately 3 kb. IL-8 includes both naturally occurring and recombinant peptides, as well as IL-8 fragments and variants that retain full or partial biological activity.

IL-8 sequences are publicly available. For example, GENBANK® Accession number NC_000004.10 discloses a human IL-8 gene sequence, and GENBANK® Accession numbers NM_000584.2 and NP_000575 disclose human IL-8 mRNA and protein sequences, respectively. One skilled in the art will appreciate that IL-8 nucleic acid and protein molecules can vary from those publicly available, such as those having one or more substitutions, deletions, insertions, or combinations thereof, while still retaining IL-8 biological activity.

IL-10: A cytokine that can inhibit the synthesis of a number of cytokines such as IFN-γ, IL-2 and TNF-β in Tc1 subpopulations of T-cells. This activity can be antagonized by IL-4. IL-10 also inhibits mitogen- or anti-CD3-induced proliferation of T-cells in the presence of accessory cells and reduces the production of IFN-γ and IL-2.

IL-10 is found in vivo as a homodimeric protein with subunits having 160 amino acids, and functional variants thereof. Human IL-10 shows 73% amino acid homology with murine IL-10, and 81% homology with murine IL-10 at the nucleotide level. The human gene for IL-10 maps to chromosome 1q31-q32, has 5 exons, and spans approximately 5 kb. However, it is understood that IL-10 includes both naturally occurring and recombinant IL-10 peptides, as well as IL-10 fragments and IL-10 variants that retain full or partial IL-10 biological activity. IL-10 is produced, for example, by activated CD8+ peripheral blood T-cells and by Tc2 cells.

IL-10 sequences are publicly available. For example, GENBANK® Accession number NC_000001.9 discloses a human IL-10 gene sequence, and GENBANK® Accession numbers NM_000572.2 and NP_000563 disclose human IL-10 mRNA and protein sequences, respectively. One skilled in the art will appreciate that IL-10 nucleic acid and protein molecules can vary from those publicly available, such as those having one or more substitutions, deletions, insertions, or combinations thereof, while still retaining IL-10 biological activity.

IL-12: A cytokine that is secreted by peripheral lymphocytes after induction. It is produced mainly by B-cells and to a lesser extent by T-cells. The most powerful inducers of IL-12 are bacteria, bacterial products, and parasites. IL-12 is produced after stimulation with phorbol esters or calcium ionophore by human B-lymphoblastoid cells. IL-12 activates NK-cells positive for CD56, and this activity is blocked by antibodies specific for TNF-alpha.

IL-12 is found in vivo as a heterodimeric 70 kDa glycoprotein consisting of a 35 kDa subunit (IL-12A) and a 40 kDa subunit (IL-12B) linked by disulfide bonds, and functional variants thereof. The human IL-12A gene is localized to chromosome 3p12-q13.2, covers about 7 kb and has seven exons. The human IL-12B gene has 8 exons spanning approximately 15 kb and maps to chromosome 5q31.1-q33.1. Human IL-12A has 60% identity to mouse IL-12A at the amino acid level, while human and mouse IL-12B share approximately 70% identity at the protein level. It is understood that IL-12 includes both naturally occurring and recombinant IL-12 peptides, as well as IL-12 fragments and IL-12 variants that retain full or partial IL-12 biological activity.

IL-12 sequences are publicly available. For example, GENBANK® Accession number NC_000003.10 discloses a human IL-12A gene sequence, and GENBANK® Accession numbers NM_000882.2 and NP_000873 disclose human IL-12A mRNA and protein sequences, respectively. GENBANK® Accession number NC_000005.8 discloses a human IL-12B gene sequence, while GENBANK® Accession numbers NM_002187.2 and NP_002178 disclose human IL-12B mRNA and protein sequences, respectively. One skilled in the art will appreciate that IL-12 nucleic acid and protein molecules can vary from those publicly available, such as those having one or more substitutions, deletions, insertions, or combinations thereof, while still retaining IL-12 biological activity.

IL-15: A cytokine that stimulates the proliferation of B-cells, NK cells, and activated CD4+, CD8+ T cells. It is produced by many cells, such as monocytes/macrophages, fibroblasts, keratinocytes, epithelial cells, heart, lung, and liver.

IL-15 is found in vivo as a monomeric protein of 114 amino acids and approximately 18 kDa, and functional variants thereof. The gene for human IL-15 maps to chromosome 4q31, spans approximately 96 kb, and has 8 exons. The mouse and human IL-15 proteins share approximately 72% identity. IL-15 includes both naturally occurring and recombinant IL-15 peptides, as well as IL-15 fragments and IL-15 variants that retain full or partial IL-15 biological activity.

IL-15 sequences are publicly available. For example, GENBANK® Accession number NC_000004.10 discloses a human IL-15 gene sequence, and GENBANK® Accession numbers NM_172174.1 and NP_751914 disclose human IL-15 mRNA and protein sequences, respectively. One skilled in the art will appreciate that IL-15 nucleic acid and protein molecules can vary from those publicly available, such as those having one or more substitutions, deletions, insertions, or combinations thereof, while still retaining IL-15 biological activity.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include cytokine molecules (such as DNA or RNA) and proteins purified by standard purification methods. The term also embraces nucleic acid molecules and proteins prepared by recombinant expression in a host cell as well as chemically synthesized nucleic acid molecules and proteins. For example, an isolated cell, such as an lung cancer cell, is one that is substantially separated from other types of cells.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. For example a nucleic acid molecule or an antibody that specifically binds to a cytokine molecule can include a label. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Lung cancer: A cancer of the lung tissue. Four main histologic subtypes of lung cancer are regularly distinguished by tumor morphology under the light microscope. Squamous and small cell tumors account for roughly 30% and 18% of all lung cancers, respectively. Theses tumors are believed to derive mainly from epithelial cells that line the larger airways. Adenocarcinomas comprise 30% of all lung cancers; these tumors are believed to be from epithelial cells that line the peripheral small airways. In addition, about 10% of lung tumors are classified as large cell, a poorly differentiated subtype usually diagnosed by exclusion of the other three types of lung cancer. Generally adenocarcinomas and large cell tumors are located in the periphery of the lung. Patients with nonsmall cell lung tumors (squamous, adenocarcinoma (AC), and large cell) are treated differently from those with small cell tumors. The classification of lung cancer is known in the art, see, for example, Travis et al. (1999) *WHO International Histological Classification of Tumors: Histological Typing of Lung and Pleural Tumors* (Springer, Heidelberg). In one example, a lung adenocarcinoma is a non small cell lung cancer (NSCLC).

A tumor can be "staged" which is a value representing the nature and extent of spread of a neoplasm and, thus, the therapeutic options and prognosis in individual patients. Stages also provide a standard by which various therapies can be compared. A combination of clinical, laboratory, radiologic, and pathologic investigations are used to stage various neoplasms.

Different staging systems have been developed for different cancers. For lung cancer, specifically for non-small cell lung cancer, the most widely used scheme for staging NSCLC is the TNM classification. The TNM staging system takes into account the degree of spread of the primary tumor, represented by T; the extent of regional lymph node involvement, represented by N; and the presence or absence of distant metastases, represented by M. In the TNM systems, four stages are further subdivided into I-III and A or B subtypes. These stages have important therapeutic and prognostic implications. One of skill in the art can readily stage a lung cancer.

Major Histocompatibility Complex: The major histocompatibility complex of humans includes both class I and class II molecules. These include class II, DR alpha (HLA-DRA), which is one of the HLA class II α chain paralogues. This class II molecule is a heterodimer consisting of an alpha and a beta chain, both anchored in the membrane. MHC plays a central role in the immune system by presenting peptides derived from extracellular proteins. Class II molecules are expressed in antigen presenting cells (APC: B lymphocytes, dendritic cells, macrophages). In humans, the alpha chain is approximately 33-35 kDa and its gene contains 5 exons.

Exon 1 encodes the leader peptide, exons 2 and 3 encode the two extracellular domains, and exon 4 encodes the transmembrane domain and the cytoplasmic tail. DRA does not have polymorphisms in the peptide binding part and acts as the sole alpha chain for DRB1, DRB3, DRB4 and DRB5.

Metastasize: The progression stage in tumor formation and development in which a range of cellular changes allow the formation of altered blood supplies (tumor vascularization) and the adoption of a malignant state in which small clumps of tumor cells termed metastases, migrate to other sites to form new tumor growths. For example, in a primary lung adenocarcinoma is can metastasize to other sites within the lung, as well as to organs outside the lung such as the lymph nodes, brain, or colon.

Nearest centroid method: A statistical method that computes a standardized centroid for each class in the training set. For example, this can be the average gene expression for each gene in each class divided by the within-class standard deviation for that gene. Nearest centroid classification takes the gene expression profile of a new sample, and compares it to each of these class centroids. The class, whose centroid it is closest to, in squared distance, is the predicted class for that new sample. "Nearest shrunken centroid classification" includes a modification to the nearest centroid method. It "shrinks" each of the class centroids toward the overall centroid for all classes by an amount called "the threshold." This shrinkage consists of moving the centroid towards zero by subtracting the threshold, setting it equal to zero if it hits zero. For example if threshold was 2.0, a centroid of 3.2 would be shrunk to 1.2, a centroid of −3.4 would be shrunk to −1.4, and a centroid of 1.2 would be shrunk to zero. The amount of shrinkage is determined by cross-validation. After shrinking the centroids, the new sample is classified by the usual nearest centroid rule, but using the shrunken class centroids.

The shrinkage has two effects: (1) it can make the classifier more accurate by reducing the effect of noisy genes; (2) it does automatic gene selection for genes that characterize the classes. The use of shrunken centroids to evaluate gene expression is disclosed in Tibshirani et al. (*Proc. Natl. Acad. Sci.* 99: 6567-72, 2002, incorporated herein by reference). A computer program that evaluates shrunken centroids can be downloaded from the Stanford University department of statistics, Tibshirani homepage, from the internet (available on Jul. 12, 2006).

Normal Tissue: The tissue from an organ of an individual that is not affected by a disease process of interest, such as cancer. Thus, "normal tissue," with regard to cancer is tissue from an individual who does not have cancer, such as an adenocarcinoma. A product, such as protein or mRNA from a "normal tissue pool" is product isolated from at least two subjects not affected by a disease process, such as from subjects who are cancer-free.

Nucleotide: Includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length, for example about 6 to 300 contiguous nucleotides of a nucleic acid molecule encoding a cytokine. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides. In particular examples, an oligonucleotide includes these numbers of contiguous nucleotides of a cytokine molecule. Such an oligonucleotide can be used on a nucleic acid array or as primers or probes to detect the presence of cytokines nucleic acid molecule.

Prediction Analysis of Microarrays (PAM): A statistical method that used unsupervised hierarchical clustering and evaluate centered correlating distance and average linkage according to the ratios of abundance in each tissue sample as compared with a control, such as a tissue pool. PAM analysis generally utilizes the nearest shrunken centroid classification with 10-fold cross validation. The method is disclosed in Tibshirani et al. (*Proc. Natl. Acad. Sci.* 99: 6567-72, 2002, incorporated herein by reference). The computer program can be downloaded from the Stanford University department of statistics, Tibshirani homepage on the internet.

Primers: Short nucleic acid molecules, for instance DNA oligonucleotides 10-100 nucleotides in length, such as about 15, 20, 25, 30 or 50 nucleotides or more in length, such as this number of contiguous nucleotides of a nucleotide sequence encoding a cytokine or other protein. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (*In Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length.

In one example, a primer includes at least 15 consecutive nucleotides of a cytokine nucleotide molecule, such as at least 18 consecutive nucleotides, at least 20, at least 25, at least 30, at least 35, at least 40, at least 45, at least 50 or more consecutive nucleotides of a nucleotide sequence (such as a gene, mRNA or cDNA). Such primers can be used to amplify a cytokine nucleotide sequence encoding a cytokine or other protein, for example using PCR.

Probe: A short sequence of nucleotides, such as at least 8, at least 10, at least 15, at least 20, at least 21, at least 25, or at least 30 nucleotides in length, used to detect the presence of a complementary sequence (such as one of the 11 cytokines of CLASS-11) by molecular hybridization. In particular examples, oligonucleotide probes include a label that permits detection of oligonucleotide probe:target sequence hybridization complexes. For example, an oligonucleotide probe can include these numbers of contiguous nucleotides of a cytokine, along with a detectable label.

Such an oligonucleotide probe can be used on a nucleic acid array to detect the presence of the cytokine.

Prognosis: The likelihood of the clinical outcome for a subject afflicted with a specific disease or disorder. With regard to cancer, the prognosis is a representation of the likelihood (probability) that the subject will survive (such as for one, two, three, four or five years) and/or the likelihood (probability) that the tumor will metastasize. A "poor prognosis" indicates a greater than 50% chance that the subject will not survive to a specified time point (such as one, two, three, for or five years), and/or a greater than 50% chance that the tumor will metastasize. In several examples, a poor prognosis indicates that there is a greater than 60%, 70%, 80%, or 90% chance that the subject will not survive and/or a greater than 60%, 70%, 80% or 90% chance that the tumor will metastasize. Conversely, a "good prognosis" indicates a greater than 50% chance that the subject will survive to a specified time point (such as one, two, three, for or five years), and/or a greater than 50% chance that the tumor will not metastasize. In several examples, a good prognosis indicates that there is a greater than 60%, 70%, 80%, or 90% chance that the subject will survive and/or a greater than 60%, 70%, 80% or 90% chance that the tumor will not metastasize.

Proteoglycan 1, secretory granule (PRG1): A molecule also known as a hematopoietic cell granule proteoglycan. Proteoglycans stored in the secretory granules of many hematopoietic cells also contain a protease-resistant peptide core, which may be important for neutralizing hydrolytic enzymes. This encoded protein was found to be associated with the macromolecular complex of granzymes and perforin, which may serve as a mediator of granule-mediated apoptosis.

PRG1 sequences are publicly available. For example, GENBANK® Accession number NC_000010.9 discloses a human PRG1 gene sequence, and GENBANK® Accession numbers NM_002727.2 and NP_002718 disclose human PRG1 mRNA and protein sequences, respectively. One skilled in the art will appreciate that PRG1 nucleic acid and protein molecules can vary from those publicly available, such as those having one or more substitutions, deletions, insertions, or combinations thereof, while still retaining PRG1 biological activity.

Purified: The term "purified" does not require absolute purity; rather, it is intended as a relative term. Thus, for example, a purified protein preparation is one in which the protein referred to is more pure than the protein in its natural environment within a cell. For example, a preparation of a protein (such as a cytokine) is purified such that the protein represents at least 50% of the total protein content of the preparation. Similarly, a purified oligonucleotide preparation is one in which the oligonucleotide is more pure than in an environment including a complex mixture of oligonucleotides.

Quantitative real-time PCR (or real time RT-PCR): A method for determining the level of specific DNA or RNA molecules in a biological sample. The accumulation of PCR product is measured at each cycle of a PCR reaction and is compared with a standard curve or quantitated relative to a control DNA or RNA. Quantitative real-time PCR is based on the use of fluorescent dyes or probes to measure the accumulation of PCR product. This may be accomplished through a TAQMAN® assay, where a fluorescently labeled probe is displaced during DNA synthesis by Taq polymerase, resulting in fluorescence, or by inclusion in the PCR reaction of a fluorescent dye such as SYBR® Green, which binds non-specifically to the accumulating double-stranded DNA.

If a standard curve is used to quantitate DNA or RNA, a series of samples containing known amounts of DNA or RNA are run simultaneously with unknown samples. The resulting fluorescence measured from the unknowns may be compared with that from the known samples in order to calculate the quantity of DNA or RNA in the sample. One application of this method is to quantify the expression of a cytokine mRNA in one or more samples from subjects with adenocarcinoma.

Quantitative real-time PCR may also be used to determine the relative quantity of a specified RNA present in a sample in comparison to a control sample when knowing the absolute copy number is not necessary. One application of this method is to determine the number of copies of an mRNA in a sample from a subject. The PCR product generated is assessed to determine how many PCR cycles is required from the PCR product to be detectable.

Sample: A biological specimen containing genomic DNA, RNA (including mRNA), protein, or combinations thereof, obtained from a subject. Examples include, but are not limited to, peripheral blood, urine, saliva, tissue biopsy, surgical specimen, and autopsy material. In one example, a sample includes a biopsy of an adenocarcinoma, a sample of noncancerous tissue, or a sample of normal tissue (from a subject not afflicted with a known disease or disorder, such as a cancer-free subject).

Subject or individual of interest: Living multi-cellular vertebrate organisms, a category that includes human and non-human mammals, such as veterinary subjects. In a particular example, a subject is one who has an adenocarcinoma, such as a lung cancer.

Test agent: Any substance, including, but not limited to, a protein (such as an antibody), nucleic acid molecule, organic compound, inorganic compound, small molecule, drug, anti-neoplastic chemotherapeutic agent, or other molecule of interest. In particular examples, a test agent can permeate a cell membrane (alone or in the presence of a carrier). In particular examples, a test agent is one whose effect on an adenocarcinoma is to be determined.

Therapeutically effective amount: An amount of a pharmaceutical preparation that alone, or together with a pharmaceutically acceptable carrier or one or more additional therapeutic agents, induces the desired response. A therapeutic agent, such as an anti-neoplastic chemotherapeutic agent, is administered in therapeutically effective amounts.

Therapeutic agents can be administered in a single dose, or in several doses, for example daily, during a course of treatment. However, the effective amount of can be dependent on the source applied, the subject being treated, the severity and type of the condition being treated, and the manner of administration. Effective amounts a therapeutic agent can be determined in many different ways, such as assaying for a sign or a symptom of an adenocarcinoma. Effective amounts also can be determined through various in vitro, in vivo or in situ assays. For example, a pharmaceutical preparation can decrease one or more symptoms of an adenocarcinoma, for example decrease a symptom by at least 20%, at least 50%, at least 70%, at least 90%, at least 98%, or even at least 100%, as compared to an amount in the absence of the pharmaceutical preparation.

TNFα: TNFα is primarily secreted by macrophages and exerts pro-inflammatory activity. Local activity of TNFα helps to contain infection, however, when infection spreads to the blood and there is systemic release of TNFα, septic shock and organ failure can occur due to loss of plasma volume as a result of increased vascular permeability. A cytokine found in vivo in humans as a 17 kDa homotrimeric protein with subunits having 157 amino acids, and variants thereof. Human and mouse TNFα have approximately 80% identity at the amino acid level. The human TNFα gene maps to chromosome 6p21.3, has 4 exons, and spans approximately 3 kb. It is understood that TNFα includes both naturally occurring and recombinant TNFα peptides, as well as TNFα fragments and TNFα variants that retain full or partial IL-15 biological activity.

TNFα sequences are publicly available. For example, GENBANK® Accession number NC_000006.10 discloses a human TNFα gene sequence, and GENBANK® Accession numbers NM_000594.2 and NP_000585 disclose human TNFα mRNA and protein sequences, respectively. One skilled in the art will appreciate that TNFα nucleic acid and protein molecules can vary from those publicly available, such as those having one or more substitutions, deletions, insertions, or combinations thereof, while still retaining TNFα biological activity.

Treating a disease: "Treatment" refers to a therapeutic intervention that ameliorates a sign or symptom of a disease or pathological condition, such a sign or symptom of an adenocarcinoma, such as a lung adenocarcinoma. Treatment can also induce remission or cure of a condition, or can reduce the pathological condition, such as a reduction in tumor size, a reduction in tumor burden, a reduction in a sign or a symptom of a tumor (such as cachexia), or a decreased ability of a tumor to metastasize. In particular examples, treatment includes preventing a disease, for example by inhibiting the full development of a disease, such as decreasing the ability of a tumor to metastasize. Prevention of a disease does not require a total absence of disease. For example, a decrease of at least 50% can be sufficient.

Under conditions sufficient for: A phrase that is used to describe any environment that permits the desired activity.

In one example, includes administering a test agent to a subject sufficient to allow the desired activity. In particular examples, the desired activity is altering the expression of a cytokine, for example normalizing such activity to control levels (such as a level found in a subject likely to survive or likely to have non-metastatic disease).

Upregulated or activation: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA, such as a cytokine.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product, such as a cytokine. In certain examples, production of a gene product increases by at least 2-fold, for example at least 3-fold or at least 4-fold, as compared to a control (such an amount of gene expression in a normal cell). In one example, a control is a centroid value obtained from subjects that do not have adenocarcinoma of the organ of interest.

Evaluation of Cytokine Expression in a Subject with an Adenocarcinoma

Provided herein are methods of evaluating a subject with adenocarcinoma, such as to determine the prognosis for the subject. For example, the methods disclosed herein can be used to determine the prognosis of the subject, which includes the likelihood (probability) of survival of the subject, or the likelihood (probability) that the adenocarcinoma will metastasize, or a combination thereof. In particular examples, the method can determine with a reasonable amount of sensitivity and specificity whether a subject is likely to survive one, two, three, four or five years. In additional examples, the method can be used to determine if an adenocarcinoma will metastasize, such as to other organs (including the lymph nodes). The adenocarcinoma can be any adenocarcinoma of interest, including lung adenocarcinoma, esophagus adenocarcinoma, gastric adenocarcinoma, renal cell adenocarcinoma, prostate adenocarcinoma, colon adenocarcinoma, pancreas adenocarcinoma, cervix adenocarcinoma, or breast adenocarcinoma. In one specific, non-limiting example, the methods disclosed herein are of use to determine the prognosis of a subject with a lung adenocarcinoma.

In additional examples, the method is utilized to determine a therapeutic regimen for the subject. In one example, the therapeutic regimen is adjuvant therapy. Thus, if the subject has a poor prognosis, a more aggressive therapeutic regimen, such as adjuvant therapy can be utilized. In particular examples, the method also includes administering an appropriate treatment therapy to subjects who have adenocarcinoma. It is helpful to be able to classify the prognosis of the subject, because there are a variety of treatments and protocols for an adenocarcinoma. Hence, using the results of the disclosed assays to help distinguish subjects that are likely to have metastasis, or are likely not to survive, offers a substantial clinical benefit, and allows subjects to be selected for more aggressive therapy.

In particular examples, methods of evaluating an adenocarcinoma involve detecting expression (such as quantitating gene or protein expression) of a plurality of cytokines of interest in the adenocarcinoma and in non-cancerous tissue in the same organ (such as non-cancerous tissue surrounding the adenocarcinoma). The cytokines of interest can include, consist essentially of, or consist of interleukin (IL)-1a, IL-1b, IL-2, IL-6, IL-8, IL-10, IL-12, IL-15, colony stimulating factor (CSF)-1 interferon (IFN)-γ and tumor necrosis factor (TNF)-a. The method can also include evaluating the expression of one or more of IL-4 and IL-5. The method can also include evaluating the expression of one or more of human leukocyte antigen (HLA)-DR, HLA-DPA1, annexin A1 (ANXA1) and platelet proteoglycan (PRG)1. In some examples, the method also includes detecting expression (such as quantitating gene or protein expression) of a plurality of cytokines of interest in tissue from organs of subjects that do not have the adenocarcinoma ("cancer-free" individuals). For example, the expression of the plurality of cytokines of interest can be compared to the expression of these cytokines in tissue from individuals that are free of cancer in the organ of interest (cancer-free) or to non-cancerous tissue. However, cancer free individuals may have had cancer in the past.

"Consists essentially of" in this context indicates that the expression of additional molecules can be evaluated (such as a control), but that these molecules do not include more than six other cytokines. Thus, in one example, the expression of a control, such as a housekeeping protein or rRNA can be assessed (such as 18S RNA, beta-microglobulin, GAPDH, and/or 18S rRNA). In some examples, "consist essentially of" indicates that no more than 5 other molecules are evaluated, such as no more than 4, 3, 2, or 1 other molecules. In this context "consist of" indicates that only the expression of the stated molecules are evaluated; the expression of additional molecules is not evaluated.

In some examples, expression values are compared to a reference value, such as a value representing expression for the same cytokine in an individual with a known metastasis status and prognosis. For example, the resulting difference in expression levels can be represented as differential expression, which can be represented by increased or decreased expression in the at least one cytokine (for instance, a nucleic acid molecule or a protein). For example, differential expression includes, but is not limited to, an increase or decrease in an amount of a nucleic acid molecule or protein, the stability of a nucleic acid molecule or protein, the localization of a nucleic acid molecule or protein, or the biological activity of a nucleic acid molecule or protein. Specific examples include evaluative methods in which changes in gene expression in at least IL-1a, IL-1b, IL-2, IL-6, IL-8, IL-10, IL-12, IL-15, CSF-1, IFN-γ and TNF-a are determined. In some examples, the expression of only IL-1a, IL-1b, IL-2, IL-6, IL-8, IL-10, IL-12, IL-15, CSF-1, IFN-γ and TNF-a are evaluated.

Figure 1B:
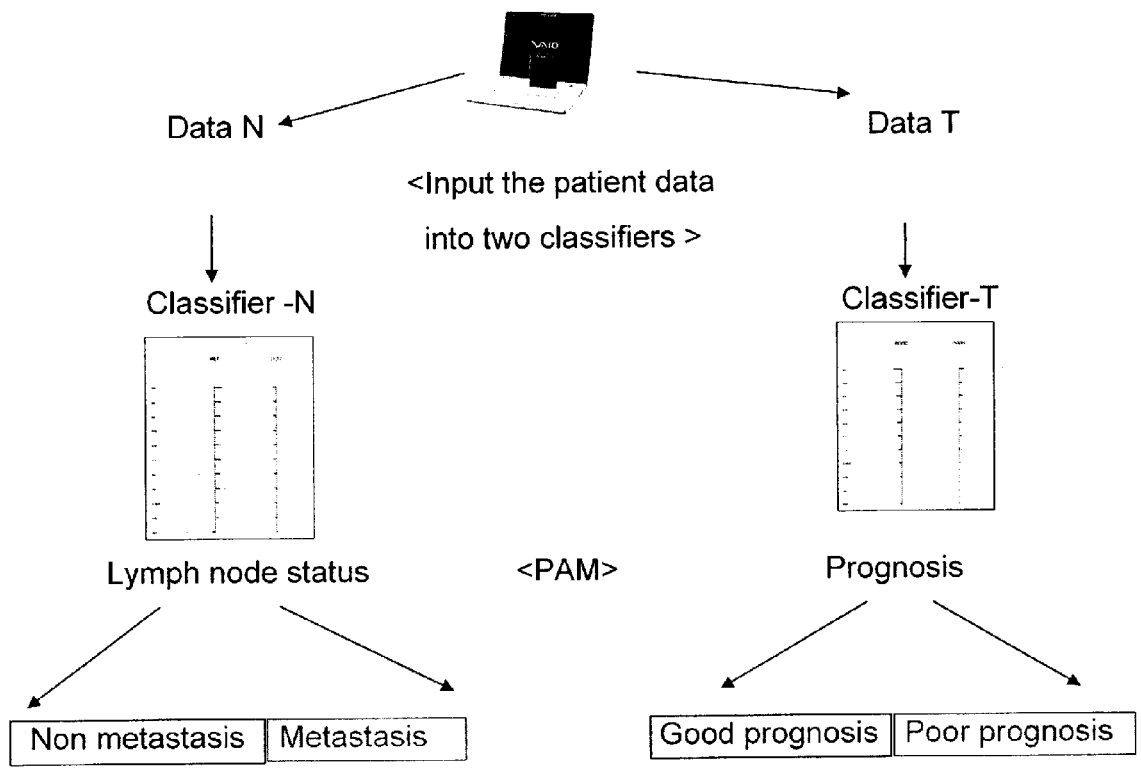
Figure 1B:
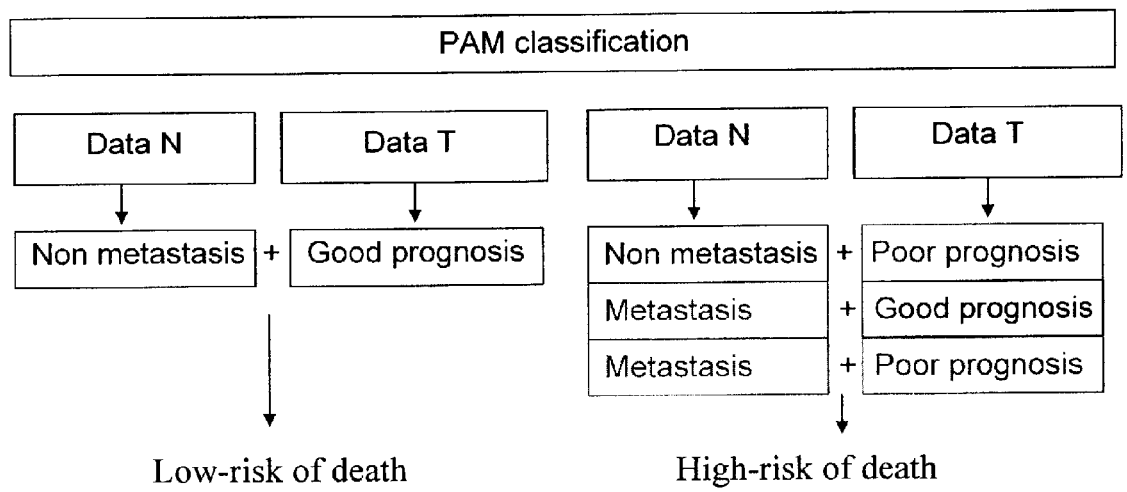

A particular embodiment of the disclosed methods is provided in FIGS. 1A and 1B. As shown in FIG. 1A, expression of IL-1a, IL-1b, IL-2, IL-6, IL-8, IL-10, IL-12, IL-15, CSF-1, IFN-γ and TNF-a are evaluated in both the adenocarcinoma and in noncancerous tissue from the same organ of the subject of interest (such as surrounding non-cancerous tissue). In some examples controls, 1-6 additional cytokines, or combinations thereof, are also evaluated. For example, real time RT-PCR can be used to quantitate mRNA expression. However, one skilled in the art will appreciate that other methods can be used to detect expression, such as other nucleic acid molecule detection methods, or protein expression can be determined. Such methods are routine in the art. The obtained raw data can be used directly, or normalized to a control. Exemplary controls include a reference value or range of values representing expression of the cytokine in normal tissue. As such, the expression of IL-1a, IL-1b, IL-2, IL-6, IL-8, IL-10, IL-12, IL-15, CSF-1, IFN-γ and TNF-a can also evaluated in normal tissue, such as a pool of sample from individuals that do not have the cancer of interest in the organ of interest. For example, in the study described herein, the normal tissue pool was from four cancer-free patients (two had a bronchial carcinoma, one had hamartoma, and one had fibrous soft tissue tumor). In such an example, the raw data for each cytokine (or control) is normalized to the appropriate cytokine (or control) reference value for the normal tissue, and this normalized value used for further analysis.

As shown in FIG. 1B, the raw or normalized cytokine expression data from adenocarcinoma (Data T) is classified as non-metastasis or metastasis, and the raw or normalized cytokine expression data from noncancerous tissue (Data N) is classified as good or poor prognosis. In a particular example, the classification of metastasis or no metastasis and good or poor prognosis is determined using a classification table with data for known cases, that is, with known metastasis status and known prognosis. Table 1 provides an exemplary classification table for raw data from non-cancerous tissue (generated from 80 US subjects see Example 1); Table 2 provides an exemplary classification table for raw data from tumor tissue (generated from 80 US subjects see Example 1); Table 3 provides an exemplary classification table for normalized data from non-cancerous tissue (generated from 80 US subjects see Example 1); Table 4 provides an exemplary classification table for normalized data from tumor tissue (generated from 80 US subjects see Example 1). For Tables 1-4, NON=non metastasis, MET=metastasis, GOOD=good prognosis, POOR=poor prognosis, and N#=patient number. Although particular classification tables are provided, one skilled in the art can generate similar tables from tumor and non-cancerous samples from adenocarcinoma positive subjects with known metastasis status and known prognosis (e.g. 5 year survival status). A final prognosis of low or high risk of death is then determined.

TABLE 1

Exemplary classification table for raw data from non-cancerous tissue.

| | N1 NON | N2 NON | N3 NON | N4 NON | N5 NON | N6 NON | N7 NON | N8 NON | N9 NON | N10 NON |
|---|---|---|---|---|---|---|---|---|---|---|
| IL-1a | −0.03 | 0.45 | 0.07 | 0.63 | 0.46 | −1.30 | −1.34 | −0.20 | −1.23 | −1.20 |
| IL-1b | 0.69 | 0.85 | 1.75 | 0.83 | 1.22 | −0.25 | −0.26 | 0.18 | 0.40 | −1.04 |
| IL-2 | −1.49 | −0.57 | 0.08 | −0.52 | −0.85 | | −1.82 | −1.52 | −1.38 | −2.50 |
| IL-8 | 1.56 | 0.79 | 2.11 | 1.59 | 1.88 | 0.03 | 0.83 | 1.27 | 1.58 | −0.96 |
| IL-10 | −0.70 | −0.89 | 1.00 | −0.86 | −0.47 | | −1.77 | −0.59 | −1.30 | −2.36 |
| IL-12p35 | −1.50 | −0.17 | −0.37 | −0.51 | −0.72 | | −1.38 | −0.57 | −1.25 | −1.00 |
| IL-15 | −1.09 | −0.58 | −0.35 | −0.24 | 0.01 | −0.76 | −0.67 | | | −1.33 |
| IFNr | −1.95 | −1.42 | −0.68 | −2.61 | −1.98 | | | | | |
| TNFa | 0.43 | 0.71 | 1.74 | 0.91 | 1.10 | | −0.77 | −0.39 | 0.76 | −0.27 | −0.49 |
| CSF1 | 0.32 | 0.16 | 0.97 | 0.60 | 0.59 | −0.01 | 0.45 | 1.26 | −0.08 | 0.62 |
| IL-6 | −0.12 | −1.46 | −0.70 | 0.47 | 0.00 | 0.44 | −0.08 | | 0.84 | −0.75 |

| | N11 NON | N12 NON | N13 NON | N14 NON | N15 NON | N16 NON | N17 NON | N18 NON | N19 NON | N20 NON |
|---|---|---|---|---|---|---|---|---|---|---|
| IL-1a | −1.16 | 1.09 | −0.12 | 1.00 | −0.95 | 1.02 | −0.58 | −0.93 | −0.19 | −0.50 |
| IL-1b | | 1.56 | 0.84 | 1.39 | −0.49 | 1.66 | 0.27 | −0.27 | 0.31 | 0.25 |
| IL-2 | | 0.39 | −0.60 | −0.59 | −0.67 | 0.14 | −1.97 | −1.74 | −1.83 | −1.10 |
| IL-8 | −0.57 | 0.83 | 1.43 | −0.08 | 0.57 | 2.38 | 1.52 | 0.47 | 1.48 | 1.44 |
| IL-10 | | −1.77 | −0.29 | −1.94 | −0.52 | 0.56 | −1.39 | −1.37 | −0.33 | −0.53 |

TABLE 1-continued

Exemplary classification table for raw data from non-cancerous tissue.

| | | | | | | | | | | |
|---|---|---|---|---|---|---|---|---|---|---|
| IL-12p35 | | 0.44 | −0.26 | −0.76 | −0.88 | | −1.75 | −1.80 | −0.78 | 0.24 |
| IL-15 | −1.22 | 0.80 | 0.26 | 0.62 | −0.84 | | −1.17 | −1.18 | −0.21 | −0.08 |
| IFNr | | −1.41 | −1.45 | −0.68 | −1.96 | | −2.19 | −2.60 | | −1.70 |
| TNFa | −0.94 | 1.65 | | 1.59 | 0.37 | | 0.13 | −0.01 | 0.69 | 1.25 |
| CSF1 | −1.40 | −0.22 | −0.48 | 0.32 | −0.27 | 0.48 | 1.08 | 0.44 | 0.90 | −0.10 |
| IL-6 | −0.21 | 0.01 | −0.50 | 0.81 | −0.14 | 0.61 | 0.79 | −0.65 | −0.35 | 0.01 |

| | N21 NON | N22 NON | N23 NON | N24 NON | N25 NON | N26 NON | N27 NON | N28 NON | N29 MET | N30 MET |
|---|---|---|---|---|---|---|---|---|---|---|
| IL-1a | 0.67 | −0.34 | −0.03 | 1.62 | −0.89 | −0.28 | −0.87 | −0.03 | 0.20 | 1.31 |
| IL-1b | 1.52 | 0.89 | 0.51 | 2.44 | 0.34 | 0.44 | 0.40 | 0.71 | 0.75 | 2.11 |
| IL-2 | −0.80 | −1.06 | −1.23 | −0.17 | −0.92 | −2.41 | −1.44 | −0.60 | −0.92 | 0.66 |
| IL-8 | 2.67 | 2.35 | 1.38 | 3.11 | 1.12 | 2.34 | 1.22 | 1.98 | 2.18 | 2.95 |
| IL-10 | −0.08 | 0.16 | −0.74 | −0.39 | −0.36 | | −1.26 | −0.09 | −0.45 | 1.70 |
| IL-12p35 | −0.44 | 0.17 | −0.71 | −0.39 | −0.89 | −0.04 | −0.76 | −1.03 | −1.02 | 0.86 |
| IL-15 | −0.42 | 0.28 | | −0.07 | | 0.50 | −0.72 | 0.00 | −0.72 | 0.45 |
| IFNr | | −1.35 | | −1.92 | | −2.74 | −1.75 | −1.54 | 0.27 | −0.48 |
| TNFa | 1.67 | 0.66 | 0.94 | 1.10 | 0.09 | 1.06 | −0.09 | 0.97 | 0.42 | 2.32 |
| CSF1 | 0.94 | 0.47 | 0.80 | 2.23 | 0.49 | | −1.28 | −0.12 | 0.27 | 1.90 |
| IL-6 | 0.73 | −1.81 | 1.72 | 1.12 | −0.32 | | −0.36 | 1.32 | 0.99 | 1.19 |

| | N31 MET | N32 MET | N33 MET | N34 MET | N35 MET | N36 MET | N37 MET | N38 MET | N39 MET | N40 MET |
|---|---|---|---|---|---|---|---|---|---|---|
| IL-1a | 1.39 | 1.15 | 1.28 | −2.24 | −1.11 | 1.75 | 1.27 | −0.83 | −0.52 | 1.13 |
| IL-1b | 2.18 | 2.07 | 1.76 | −1.95 | −0.35 | 2.00 | 1.42 | −0.10 | −0.23 | 1.93 |
| IL-2 | 0.68 | −0.09 | 0.30 | | −2.64 | −1.15 | 0.16 | | | 0.72 |
| IL-8 | 2.93 | 2.84 | 1.81 | −0.48 | 1.22 | 2.57 | 2.74 | 0.58 | 1.00 | 2.90 |
| IL-10 | 1.46 | 1.13 | 0.35 | | −2.10 | 0.01 | 0.31 | | | |
| IL-12p35 | 0.93 | 0.00 | 0.25 | | −1.46 | −0.39 | 1.01 | −0.83 | | |
| IL-15 | 0.51 | 0.57 | 0.34 | −1.64 | −1.21 | 0.60 | 1.70 | | 0.46 | 0.78 |
| IFNr | −0.74 | −1.05 | −0.55 | | | −1.37 | | | | |
| TNFa | 2.41 | 2.40 | 2.45 | −1.45 | 0.01 | 1.05 | 1.87 | | | 1.96 |
| CSF1 | 0.77 | 0.85 | 0.25 | −0.82 | 0.45 | −0.18 | −0.57 | −0.90 | −0.91 | −0.11 |
| IL-6 | 0.63 | 1.48 | −0.52 | −0.21 | 0.42 | 1.20 | 1.31 | 0.41 | 0.09 | −0.07 |

| | N41 NON | N42 NON | N43 NON | N44 NON | N45 NON | N46 NON | N47 NON | N48 NON | N49 NON | N50 NON |
|---|---|---|---|---|---|---|---|---|---|---|
| IL-1a | −0.13 | −1.49 | −0.31 | −0.49 | −1.01 | −1.64 | 2.19 | −0.62 | −1.56 | −0.46 |
| IL-1b | 1.17 | −0.97 | 0.64 | 0.01 | 0.13 | 0.17 | 2.89 | 0.35 | −0.67 | 0.06 |
| IL-2 | −0.59 | −1.82 | −1.32 | −1.55 | −2.03 | −1.62 | 0.20 | −1.12 | −2.01 | −1.73 |
| IL-8 | 2.16 | 0.21 | 1.98 | 1.79 | 1.11 | 1.24 | 2.72 | 1.11 | 0.41 | 0.13 |
| IL-10 | −0.44 | −1.17 | −1.10 | −1.20 | −1.03 | −1.35 | 0.25 | −0.73 | −1.30 | −1.95 |
| IL-12p35 | −0.12 | −1.02 | −1.03 | −1.13 | −1.47 | −0.69 | 0.46 | −0.38 | −1.63 | −1.58 |
| IL-15 | −0.19 | −1.11 | −0.93 | −1.20 | −1.26 | −1.29 | 0.41 | 0.24 | −0.71 | −1.14 |
| IFNr | −1.21 | −1.32 | −1.86 | −2.23 | −2.69 | −2.88 | −0.53 | −1.93 | −2.68 | −2.97 |
| TNFa | 0.54 | −0.46 | 0.77 | 0.02 | 0.05 | 0.32 | 2.79 | 0.91 | −0.16 | 0.01 |
| CSF1 | 0.50 | −0.18 | 0.76 | 0.63 | 1.19 | 0.33 | 0.80 | 1.15 | 0.88 | 1.00 |
| IL-6 | 0.88 | −0.99 | 1.02 | −0.93 | 0.36 | −0.71 | −0.80 | 1.05 | 0.17 | −0.82 |

| | N51 NON | N52 NON | N53 NON | N54 NON | N55 NON | N56 NON | N57 NON | N58 NON | N59 NON | N60 NON |
|---|---|---|---|---|---|---|---|---|---|---|
| IL-1a | −0.43 | −1.11 | | −0.29 | −0.64 | −0.70 | −0.28 | −1.84 | −0.37 | −0.84 |
| IL-1b | 0.47 | −0.35 | | 0.28 | −0.23 | −0.18 | 0.76 | −0.44 | 0.28 | −0.14 |
| IL-2 | −1.59 | −1.78 | | −1.04 | | −1.75 | −0.17 | −2.00 | −1.68 | −0.57 |
| IL-8 | 1.85 | 1.07 | −1.67 | 1.34 | 1.05 | 0.57 | 1.38 | 1.09 | 1.35 | 2.08 |
| IL-10 | −1.35 | −1.01 | | −0.37 | | −1.25 | 0.32 | −1.88 | −1.23 | −0.21 |
| IL-12p35 | −1.37 | −1.67 | | 0.16 | | −1.29 | 0.03 | −2.11 | −1.36 | −0.88 |
| IL-15 | −0.67 | −0.87 | −1.05 | −0.13 | 0.94 | −1.23 | | −2.00 | −0.89 | 0.09 |
| IFNr | −2.21 | −1.58 | | −1.77 | | −2.52 | | −2.23 | −2.30 | |
| TNFa | 0.92 | −0.14 | −2.72 | 1.30 | | −0.03 | 2.09 | −1.23 | 0.37 | 1.23 |
| CSF1 | 1.70 | 0.78 | | −0.10 | | 0.50 | 0.90 | −0.91 | 0.69 | 1.37 |
| IL-6 | 1.37 | 1.45 | | 0.16 | −0.43 | −0.73 | −0.52 | −0.54 | −0.06 | 0.52 |

| | N61 NON | N62 NON | N63 NON | N64 NON | N65 NON | N66 NON | N67 NON | N68 NON | N69 MET | N70 MET |
|---|---|---|---|---|---|---|---|---|---|---|
| IL-1a | −1.45 | 0.83 | 1.68 | −2.01 | 0.48 | −0.76 | −0.40 | −0.28 | 0.02 | 0.98 |
| IL-1b | 0.55 | 1.43 | 2.56 | −1.05 | 0.85 | −0.24 | 1.16 | 1.34 | 0.54 | 1.90 |
| IL-2 | −0.96 | −0.43 | 0.29 | −2.91 | −0.93 | | −0.47 | | −0.28 | −0.06 |

TABLE 1-continued

Exemplary classification table for raw data from non-cancerous tissue.

| | | | | | | | | | | |
|---|---|---|---|---|---|---|---|---|---|---|
| IL-8 | 0.63 | 2.63 | 3.18 | 0.47 | 1.75 | 0.36 | 2.22 | 2.06 | 2.56 | 2.74 |
| IL-10 | −0.05 | −0.19 | 0.39 | −2.24 | −1.31 | −0.80 | −0.85 | −0.29 | 0.63 | 1.19 |
| IL-12p35 | −0.37 | −0.57 | 0.35 | −2.34 | −0.35 | | −0.27 | −1.06 | −0.30 | |
| IL-15 | −0.32 | −0.33 | 0.85 | −1.70 | | −0.70 | 0.43 | 0.21 | 0.51 | |
| IFNr | −1.16 | | | −3.03 | | | −4.68 | −0.94 | 0.29 | −0.08 |
| TNFa | 1.24 | 1.82 | 2.43 | −0.36 | 0.87 | −0.78 | 1.74 | 0.65 | 0.49 | 3.21 |
| CSF1 | 0.11 | 1.19 | 1.45 | 0.33 | 1.11 | 0.61 | 0.02 | 0.02 | −0.09 | −0.22 |
| IL-6 | −1.66 | 0.82 | 0.77 | −0.28 | 0.20 | 0.11 | 0.89 | 1.09 | −0.48 | −0.01 |

| | N71 MET | N72 MET | N73 MET | N74 MET | N75 MET | N76 MET | N77 MET | N78 MET | N79 MET | N80 MET |
|---|---|---|---|---|---|---|---|---|---|---|
| IL-1a | 1.92 | 0.62 | −0.84 | −1.11 | 1.16 | −0.67 | −0.69 | −1.14 | −1.97 | 0.61 |
| IL-1b | 2.54 | 2.40 | 0.35 | 0.23 | 1.21 | −0.05 | 0.28 | 0.04 | −1.38 | 1.51 |
| IL-2 | 0.38 | 0.23 | −2.09 | −0.81 | 0.08 | −1.75 | −1.20 | −1.54 | −2.48 | |
| IL-8 | 2.80 | 3.30 | 1.38 | 1.04 | 2.07 | 1.86 | 1.54 | 1.24 | −0.07 | 3.71 |
| IL-10 | 1.01 | 0.88 | −0.53 | −0.58 | 0.36 | −1.08 | −0.56 | −1.11 | −1.94 | 1.51 |
| IL-12p35 | 0.97 | 0.38 | −1.70 | −0.99 | | −1.40 | −1.50 | −0.87 | | |
| IL-15 | | 0.62 | −1.04 | 0.14 | 0.10 | −0.78 | −0.89 | −0.76 | −1.10 | |
| IFNr | | | | −1.15 | | −2.65 | −2.09 | | −2.76 | |
| TNFa | 3.05 | 1.77 | 0.29 | 0.54 | 1.72 | −0.48 | −0.35 | −0.22 | −0.52 | 0.85 |
| CSF1 | 0.49 | 0.88 | 0.40 | 0.77 | 0.13 | −0.27 | −0.13 | −0.48 | −0.56 | 0.43 |
| IL-6 | −0.60 | 1.78 | 1.04 | 1.15 | 1.27 | 0.88 | 1.38 | 0.09 | 0.40 | 1.02 |

TABLE 2

Exemplary classification table for raw data from tumor tissue.

| | T1 GOOD | T2 GOOD | T3 GOOD | T4 GOOD | T5 GOOD | T6 GOOD | T7 GOOD | T8 GOOD | T9 GOOD | T10 GOOD |
|---|---|---|---|---|---|---|---|---|---|---|
| IL-1a | −0.76 | −1.15 | −1.06 | −0.66 | −1.62 | −2.23 | −0.61 | −1.41 | −1.84 | −1.96 |
| IL-1b | 0.36 | 0.21 | −0.17 | 1.16 | −0.69 | −0.45 | 0.27 | −0.42 | −1.03 | −1.07 |
| IL-2 | −1.19 | −1.50 | −1.80 | −0.36 | −1.60 | −1.95 | −2.34 | −3.08 | −2.49 | −3.02 |
| IL-8 | 0.72 | 0.59 | 0.30 | 2.55 | 0.42 | −0.03 | 1.11 | 1.02 | 0.66 | −0.17 |
| IL-10 | −0.75 | −0.80 | −0.91 | 0.80 | −1.23 | −0.98 | −0.69 | −0.67 | −1.31 | −1.62 |
| IL-12p35 | −0.95 | −1.72 | −0.59 | −0.01 | −1.54 | −1.67 | −1.37 | −1.38 | −1.61 | −2.26 |
| IL-15 | −1.08 | −1.41 | −0.83 | −0.36 | −0.65 | −1.02 | −1.02 | −1.65 | −1.88 | −2.09 |
| IFNr | −2.04 | −2.59 | −2.41 | −0.78 | −2.08 | −1.69 | −1.12 | −2.85 | −2.98 | −3.64 |
| TNFa | 0.35 | −0.06 | −0.73 | 0.63 | −1.05 | −0.35 | −0.29 | −0.90 | −1.61 | −0.95 |
| CSF1 | 0.19 | 0.46 | −0.32 | −0.28 | −1.06 | 0.71 | 1.08 | 0.81 | −0.14 | 0.05 |
| IL-6 | −1.94 | −2.01 | −1.15 | 1.36 | 0.01 | −0.07 | −1.89 | −0.53 | 0.22 | 0.08 |

| | T11 GOOD | T12 GOOD | T13 GOOD | T14 GOOD | T15 POOR | T16 POOR | T17 POOR | T18 POOR | T19 POOR | T20 POOR |
|---|---|---|---|---|---|---|---|---|---|---|
| IL-1a | −1.89 | −2.58 | 0.88 | 0.58 | 0.48 | −0.68 | −0.36 | −0.63 | 0.48 | 0.18 |
| IL-1b | −1.30 | −1.31 | 3.27 | 0.58 | 0.54 | 0.43 | 0.56 | 0.67 | 1.22 | 1.61 |
| IL-2 | | | 0.66 | −0.50 | −0.69 | −0.77 | −1.42 | 0.10 | −0.69 | −0.21 |
| IL-8 | −0.21 | 0.83 | 2.58 | 2.12 | 2.22 | 1.32 | 1.41 | 1.41 | 2.64 | 2.86 |
| IL-10 | −2.05 | −0.48 | 1.11 | −0.54 | −0.37 | −0.06 | −0.24 | −0.20 | 0.74 | 0.44 |
| IL-12p35 | | −1.77 | 0.38 | −0.08 | 0.37 | −0.42 | −0.24 | −0.37 | −0.92 | 0.30 |
| IL-15 | −1.47 | −2.00 | 1.40 | 0.99 | −0.06 | −0.01 | −0.20 | 0.19 | 0.26 | 0.98 |
| IFNr | | −1.70 | | | −0.80 | −0.85 | −0.99 | −0.41 | −1.26 | 0.27 |
| TNFa | | −1.49 | 2.05 | 0.02 | 1.27 | 1.43 | 0.55 | 0.16 | 1.60 | 1.47 |
| CSF1 | −1.47 | 0.32 | 0.62 | 0.04 | 0.07 | 0.70 | 0.69 | 0.07 | −0.47 | 0.72 |
| IL-6 | −0.54 | −0.74 | 0.10 | 0.06 | −0.20 | −0.97 | −0.64 | −1.57 | 1.42 | 0.15 |

| | T21 POOR | T22 POOR | T23 POOR | T24 POOR | T25 POOR | T26 POOR | T27 POOR | T28 POOR | T29 POOR | T30 POOR |
|---|---|---|---|---|---|---|---|---|---|---|
| IL-1a | −0.61 | 0.07 | −1.02 | 0.68 | −1.93 | −1.52 | −0.86 | −0.84 | 1.32 | 0.01 |
| IL-1b | 0.81 | 0.86 | 0.31 | 1.42 | −0.14 | −0.07 | 0.29 | 0.32 | 0.89 | 0.91 |
| IL-2 | −1.29 | −2.28 | −1.64 | −0.51 | −2.30 | −1.60 | −1.35 | −1.17 | −1.78 | −0.75 |
| IL-8 | 1.60 | 2.40 | 1.33 | 2.08 | 0.63 | 0.58 | 0.96 | 2.26 | 1.22 | 2.21 |
| IL-10 | −0.40 | 0.16 | −0.66 | 1.14 | −0.86 | −1.09 | −0.33 | 0.08 | −0.65 | −0.45 |
| IL-12p35 | −0.52 | −1.67 | −1.79 | 0.45 | −1.80 | −1.16 | −1.31 | −0.75 | −0.39 | 0.14 |
| IL-15 | −0.53 | −1.15 | −1.28 | 0.33 | −2.40 | −0.89 | −1.15 | −0.41 | −0.20 | 0.23 |
| IFNr | −1.67 | −0.68 | −2.34 | | −2.13 | −1.74 | −1.22 | −1.61 | −0.98 | −0.65 |
| TNFa | −0.01 | 0.00 | −0.29 | 1.49 | −1.15 | −0.13 | 0.26 | 0.32 | 0.55 | 0.92 |

TABLE 2-continued

Exemplary classification table for raw data from tumor tissue.

| | | | | | | | | | | |
|---|---|---|---|---|---|---|---|---|---|---|
| CSF1 | −0.12 | 0.57 | 0.16 | 1.56 | −0.52 | 1.11 | 1.27 | −0.16 | 0.41 | 0.79 |
| IL-6 | −1.22 | −1.28 | −2.81 | −2.49 | −0.97 | −2.26 | −1.50 | 0.26 | −0.22 | −0.66 |

| | T31 POOR | T32 POOR | T33 POOR | T34 POOR | T35 POOR | T36 POOR | T37 GOOD | T38 GOOD | T39 POOR | T40 GOOD |
|---|---|---|---|---|---|---|---|---|---|---|
| IL-1a | −0.28 | −0.12 | −1.23 | −2.65 | −1.28 | 0.15 | −1.10 | −1.15 | | −0.10 |
| IL-1b | 0.56 | 1.23 | −0.36 | −1.42 | −0.29 | 1.62 | −0.33 | −0.82 | −0.38 | 0.27 |
| IL-2 | −0.86 | −0.90 | −2.23 | −3.11 | −0.71 | −1.60 | −1.32 | −2.92 | | −2.14 |
| IL-8 | 2.18 | 2.80 | 1.88 | −0.16 | 1.65 | 3.43 | 0.85 | 0.70 | 1.58 | 0.99 |
| IL-10 | 0.48 | 0.34 | −1.30 | −2.20 | −0.77 | −0.71 | −0.75 | −1.54 | | −1.28 |
| IL-12p35 | −0.44 | 0.21 | −0.96 | −2.70 | −1.23 | −2.03 | −1.23 | −1.95 | | −1.64 |
| IL-15 | −0.04 | 0.00 | −0.68 | −2.52 | −1.21 | −0.97 | −1.20 | −1.22 | | −0.60 |
| IFNr | −1.00 | −1.88 | −2.71 | −3.06 | −0.50 | | −0.84 | | | −1.90 |
| TNFa | 0.40 | 1.77 | −0.03 | −2.17 | 0.23 | 0.50 | −0.37 | −0.92 | | 0.14 |
| CSF1 | 0.54 | 1.54 | −0.08 | −0.71 | −0.48 | −0.13 | −1.66 | 0.27 | −0.85 | 0.15 |
| IL-6 | 0.24 | 0.36 | −0.68 | −2.00 | −0.02 | 0.60 | 1.66 | −0.58 | 0.18 | 0.20 |

| | T41 GOOD | T42 GOOD | T43 GOOD | T44 GOOD | T45 GOOD | T46 GOOD | T47 GOOD | T48 GOOD | T49 GOOD | T50 GOOD |
|---|---|---|---|---|---|---|---|---|---|---|
| IL-1a | −1.40 | −1.04 | −0.18 | −0.59 | −0.33 | 0.05 | 0.77 | −1.38 | | −0.91 |
| IL-1b | −0.25 | −0.08 | 1.00 | 0.11 | 0.65 | 0.04 | 1.98 | −0.69 | −0.96 | 0.46 |
| IL-2 | −0.91 | −1.79 | −0.61 | −0.76 | −1.42 | −1.53 | −0.06 | −2.92 | | −1.90 |
| IL-8 | 0.94 | 0.32 | 1.95 | 1.41 | 1.41 | 0.83 | 1.85 | 0.90 | 0.43 | 1.16 |
| IL-10 | −0.55 | −0.98 | −0.27 | −0.42 | −0.22 | −0.92 | 0.64 | −1.46 | −1.35 | −0.52 |
| IL-12p35 | −0.95 | −1.33 | −0.11 | −0.79 | −0.24 | −0.89 | 0.22 | −2.38 | −2.27 | −1.67 |
| IL-15 | −0.43 | −0.98 | 0.08 | −0.27 | −0.20 | −0.52 | −0.87 | −1.71 | −1.60 | −1.32 |
| IFNr | −1.36 | −2.26 | −0.98 | −1.26 | −0.86 | −1.95 | | −2.41 | | −2.03 |
| TNFa | 0.21 | 0.01 | 0.84 | 0.09 | 0.55 | −0.40 | | −0.59 | −1.98 | −0.49 |
| CSF1 | 0.36 | 0.37 | 0.63 | 0.51 | 1.02 | 0.38 | 0.08 | −0.55 | 0.09 | 1.07 |
| IL-6 | 0.52 | −0.39 | −0.05 | −0.83 | −0.70 | −2.58 | −0.74 | −0.62 | −1.24 | 2.04 |

| | T51 GOOD | T52 GOOD | T53 GOOD | T54 GOOD | T55 GOOD | T56 POOR | T57 POOR | T58 POOR | T59 POOR | T60 POOR |
|---|---|---|---|---|---|---|---|---|---|---|
| IL-1a | −1.30 | −1.32 | | −1.37 | | −0.25 | 0.23 | 0.07 | 0.59 | −0.18 |
| IL-1b | 0.19 | −0.37 | −1.75 | −0.67 | −1.24 | 1.00 | 1.48 | 0.57 | 0.78 | 1.44 |
| IL-2 | −1.97 | −2.61 | −2.85 | −1.18 | | −0.10 | 0.18 | −0.63 | −1.00 | −0.89 |
| IL-8 | 1.55 | 1.57 | −0.57 | 0.91 | 0.13 | 1.80 | 2.39 | 2.00 | 1.64 | 1.96 |
| IL-10 | −0.86 | −1.32 | | −0.78 | −1.63 | 0.33 | 0.93 | −0.44 | −0.29 | 0.52 |
| IL-12p35 | −1.44 | −1.70 | | −2.04 | −1.82 | 0.05 | 0.13 | −0.79 | −0.70 | 0.70 |
| IL-15 | −1.24 | −1.70 | −1.93 | −1.54 | −0.90 | 0.54 | 0.09 | −0.30 | 0.18 | 0.81 |
| IFNr | −2.05 | −2.01 | −3.22 | −2.22 | | 0.09 | −0.74 | −1.16 | −1.02 | −0.95 |
| TNFa | −0.54 | −0.57 | −1.71 | −0.42 | −2.14 | 2.06 | 2.23 | 0.13 | 0.47 | 1.00 |
| CSF1 | 1.35 | 0.87 | | −1.67 | | −0.42 | 0.83 | −0.32 | 0.47 | 1.58 |
| IL-6 | 1.63 | −1.23 | −0.49 | −1.53 | 0.14 | −0.82 | −0.09 | −0.95 | −0.45 | −0.19 |

| | T61 POOR | T62 POOR | T63 POOR | T64 POOR | T65 POOR | T66 POOR | T67 POOR | T68 POOR | T69 POOR | T70 POOR |
|---|---|---|---|---|---|---|---|---|---|---|
| IL-1a | −0.07 | −0.52 | −0.12 | −1.81 | −1.92 | −1.21 | −0.76 | −0.16 | 0.17 | −0.90 |
| IL-1b | 1.97 | 0.31 | 0.31 | 0.21 | −0.34 | −0.56 | 0.80 | 0.31 | 0.71 | 0.50 |
| IL-2 | −0.21 | −0.94 | −0.95 | −1.61 | −2.82 | | −1.10 | −2.11 | −0.25 | −0.99 |
| IL-8 | 1.47 | 0.71 | 1.16 | 1.98 | 0.85 | 0.83 | 1.61 | 1.95 | 2.64 | 1.23 |
| IL-10 | 0.51 | −0.21 | 0.08 | −0.40 | −1.34 | −1.30 | −0.39 | −1.10 | 0.74 | −0.22 |
| IL-12p35 | 0.44 | −0.70 | −0.15 | −1.15 | −2.18 | −2.40 | −0.43 | −1.25 | −0.30 | −1.01 |
| IL-15 | −0.11 | −0.30 | 0.47 | −0.98 | −1.71 | −1.77 | 0.35 | −0.37 | 0.71 | 0.11 |
| IFNr | −1.42 | −1.28 | −0.86 | −1.63 | −1.92 | −3.62 | −0.22 | −2.54 | 0.16 | −1.35 |
| TNFa | 2.25 | 0.48 | 1.33 | −0.47 | −1.39 | −0.96 | 0.07 | 0.63 | 0.53 | 1.06 |
| CSF1 | 1.13 | −0.07 | 0.37 | 1.77 | 0.80 | 0.30 | −0.90 | 0.06 | −0.09 | −0.12 |
| IL-6 | −1.10 | −2.07 | −0.90 | −1.96 | −2.09 | | −0.79 | −0.73 | 0.29 | −0.48 |

| | T71 POOR | T72 POOR | T73 POOR | T74 GOOD | T75 POOR | T76 POOR | T77 POOR | T78 GOOD | T79 POOR | T80 POOR |
|---|---|---|---|---|---|---|---|---|---|---|
| IL-1a | −0.60 | −0.15 | −1.37 | −1.35 | −2.01 | −0.78 | −0.81 | −2.43 | −0.80 | −0.49 |
| IL-1b | −0.10 | 0.78 | 0.53 | −0.13 | −0.27 | 0.88 | 0.59 | −1.75 | 0.07 | 0.20 |
| IL-2 | −1.27 | −1.17 | −0.80 | −1.77 | −1.90 | −2.17 | −1.73 | | −2.48 | −0.71 |
| IL-8 | 1.34 | 1.70 | 1.65 | 0.66 | 1.12 | 1.71 | 0.63 | | 1.90 | 1.61 |
| IL-10 | −0.99 | −0.09 | −0.12 | −0.82 | −1.15 | 0.51 | 0.39 | | −1.07 | −0.46 |
| IL-12p35 | −0.67 | 0.02 | −0.55 | −1.08 | −2.27 | −1.23 | −0.82 | −2.18 | −1.20 | −0.62 |

TABLE 2-continued

Exemplary classification table for raw data from tumor tissue.

| | | | | | | | | | | |
|---|---|---|---|---|---|---|---|---|---|---|
| IL-15 | 0.06 | −0.64 | −0.69 | −0.94 | −2.10 | −0.99 | −2.06 | −2.10 | −0.88 | −0.56 |
| IFNr | −1.61 | −1.14 | −1.54 | −1.23 | −2.31 | −1.43 | −1.11 | | −1.62 | −1.02 |
| TNFa | 0.27 | 0.80 | 0.15 | −0.52 | −1.15 | −0.55 | 0.09 | −2.18 | −0.34 | 0.13 |
| CSF1 | 0.06 | 0.81 | 0.12 | 0.59 | 1.11 | 0.40 | 0.82 | −2.25 | 1.07 | 0.56 |
| IL-6 | −0.51 | −0.88 | −0.14 | 0.07 | −0.98 | 0.28 | −0.69 | | −0.44 | 0.46 |

TABLE 3

Exemplary classification table for normalized data from non-cancerous tissue.

| | N1 NON | N2 NON | N3 NON | N4 NON | N5 NON | N6 NON | N7 NON | N8 NON | N9 NON | N10 NON |
|---|---|---|---|---|---|---|---|---|---|---|
| IL-1a | 0.12 | 0.60 | 0.22 | 0.78 | 0.61 | −1.15 | −1.19 | −0.05 | −1.08 | −1.06 |
| IL-1b | 0.31 | 0.47 | 1.37 | 0.45 | 0.84 | −0.63 | −0.64 | −0.21 | 0.02 | −1.42 |
| IL-2 | −0.12 | 0.80 | 1.45 | 0.86 | 0.52 | | −0.45 | −0.15 | −0.01 | −1.13 |
| IL-8 | −0.60 | −1.37 | −0.05 | −0.56 | −0.27 | −2.13 | −1.33 | −0.89 | −0.58 | −3.12 |
| IL-10 | −0.66 | −0.85 | 1.04 | −0.82 | −0.43 | | −1.73 | −0.55 | −1.26 | −2.32 |
| IL-12p35 | −0.32 | 1.01 | 0.81 | 0.67 | 0.46 | | −0.20 | 0.61 | −0.07 | 0.18 |
| IL-15 | 0.10 | 0.61 | 0.84 | 0.94 | 1.19 | 0.43 | 0.52 | | | −0.14 |
| IFNr | 0.85 | 1.38 | 2.11 | 0.18 | 0.81 | | | | | |
| TNFa | −0.13 | 0.15 | 1.18 | 0.35 | 0.55 | −1.32 | −0.94 | 0.20 | −0.82 | −1.05 |
| CSF1 | −0.25 | −0.41 | 0.40 | 0.03 | 0.02 | −0.58 | −0.11 | 0.70 | −0.64 | 0.05 |
| IL-6 | 0.02 | −1.31 | −0.56 | 0.61 | 0.14 | 0.59 | 0.06 | | 0.98 | −0.61 |

| | N11 NON | N12 NON | N13 NON | N14 NON | N15 NON | N16 NON | N17 NON | N18 NON | N19 NON | N20 NON |
|---|---|---|---|---|---|---|---|---|---|---|
| IL-1a | −1.01 | 1.24 | 0.03 | 1.15 | −0.80 | 1.17 | −0.43 | −0.78 | −0.04 | −0.36 |
| IL-1b | | 1.18 | 0.45 | 1.01 | −0.87 | 1.28 | −0.11 | −0.65 | −0.08 | −0.13 |
| IL-2 | | 1.76 | 0.77 | 0.78 | 0.70 | 1.51 | −0.60 | −0.37 | −0.46 | 0.27 |
| IL-8 | −2.73 | −1.33 | −0.73 | −2.23 | −1.59 | 0.22 | −0.64 | −1.68 | −0.68 | −0.71 |
| IL-10 | | −1.73 | −0.25 | −1.90 | −0.48 | 0.60 | −1.35 | −1.33 | −0.29 | −0.49 |
| IL-12p35 | | 1.62 | 0.92 | 0.42 | 0.30 | | −0.56 | −0.62 | 0.40 | 1.42 |
| IL-15 | −0.03 | 1.99 | 1.44 | 1.81 | 0.35 | | 0.02 | 0.01 | 0.98 | 1.11 |
| IFNr | | 1.38 | 1.34 | 2.11 | 0.84 | | 0.60 | 0.19 | | 1.09 |
| TNFa | −1.49 | 1.09 | | 1.03 | −0.19 | | −0.43 | −0.56 | 0.14 | 0.70 |
| CSF1 | −1.97 | −0.79 | −1.05 | −0.25 | −0.83 | −0.09 | 0.51 | −0.13 | 0.34 | −0.67 |
| IL-6 | −0.07 | 0.15 | −0.36 | 0.95 | 0.00 | 0.75 | 0.94 | −0.51 | −0.21 | 0.15 |

| | N21 NON | N22 NON | N23 NON | N24 NON | N25 NON | N26 NON | N27 NON | N28 NON | N29 MET | N30 MET |
|---|---|---|---|---|---|---|---|---|---|---|
| IL-1a | 0.82 | −0.19 | 0.12 | 1.77 | −0.74 | −0.13 | −0.72 | 0.12 | 0.35 | 1.46 |
| IL-1b | 1.14 | 0.50 | 0.13 | 2.06 | −0.04 | 0.05 | 0.02 | 0.33 | 0.37 | 1.72 |
| IL-2 | 0.57 | 0.31 | 0.14 | 1.20 | 0.45 | −1.04 | −0.07 | 0.77 | 0.45 | 2.03 |
| IL-8 | 0.51 | 0.19 | −0.78 | 0.96 | −1.03 | 0.18 | −0.93 | −0.18 | 0.02 | 0.79 |
| IL-10 | −0.04 | 0.20 | −0.70 | −0.35 | −0.33 | | −1.22 | −0.05 | −0.42 | 1.74 |
| IL-12p35 | 0.74 | 1.36 | 0.47 | 0.79 | 0.29 | 1.14 | 0.42 | 0.15 | 0.17 | 2.04 |
| IL-15 | 0.77 | 1.47 | | 1.12 | | 1.69 | 0.47 | 1.18 | 0.46 | 1.64 |
| IFNr | | 1.45 | | 0.88 | | 0.06 | 1.04 | 1.25 | 3.07 | 2.32 |
| TNFa | 1.12 | 0.11 | 0.39 | 0.54 | −0.46 | 0.51 | −0.65 | 0.41 | −0.14 | 1.76 |
| CSF1 | 0.37 | −0.09 | 0.23 | 1.66 | −0.07 | | −1.84 | −0.68 | −0.30 | 1.34 |
| IL-6 | 0.88 | −1.67 | 1.86 | 1.26 | −0.18 | | −0.22 | 1.46 | 1.13 | 1.33 |

| | N31 MET | N32 MET | N33 MET | N34 MET | N35 MET | N36 MET | N37 MET | N38 MET | N39 MET | N40 MET |
|---|---|---|---|---|---|---|---|---|---|---|
| IL-1a | 1.54 | 1.30 | 1.43 | −2.09 | −0.96 | 1.90 | 1.42 | −0.68 | −0.37 | 1.28 |
| IL-1b | 1.80 | 1.69 | 1.38 | −2.34 | −0.73 | 1.61 | 1.04 | −0.48 | −0.61 | 1.55 |
| IL-2 | 2.05 | 1.29 | 1.68 | | −1.27 | 0.22 | 1.53 | | | 2.09 |
| IL-8 | 0.77 | 0.69 | −0.35 | −2.64 | −0.94 | 0.41 | 0.59 | −1.58 | −1.15 | 0.74 |
| IL-10 | 1.50 | 1.17 | 0.39 | | −2.06 | 0.04 | 0.35 | | | |
| IL-12p35 | 2.11 | 1.18 | 1.43 | | −0.28 | 0.79 | 2.19 | 0.36 | | |
| IL-15 | 1.69 | 1.76 | 1.52 | −0.45 | −0.02 | 1.79 | 2.89 | | 1.65 | 1.97 |
| IFNr | 2.05 | 1.75 | 2.25 | | | 1.43 | | | | |
| TNFa | 1.85 | 1.85 | 1.90 | −2.01 | −0.55 | 0.49 | 1.32 | | | 1.40 |
| CSF1 | 0.20 | 0.29 | −0.32 | −1.38 | −0.12 | −0.75 | −1.14 | −1.47 | −1.48 | −0.67 |
| IL-6 | 0.77 | 1.63 | −0.38 | −0.06 | 0.56 | 1.34 | 1.45 | 0.55 | 0.23 | 0.07 |

TABLE 3-continued

Exemplary classification table for normalized data from non-cancerous tissue.

|  | N41 NON | N42 NON | N43 NON | N44 NON | N45 NON | N46 NON | N47 NON | N48 NON | N49 NON | N50 NON |
|---|---|---|---|---|---|---|---|---|---|---|
| IL-1a | 0.02 | −1.34 | −0.16 | −0.34 | −0.86 | −1.49 | 2.34 | −0.47 | −1.41 | −0.31 |
| IL-1b | 0.78 | −1.36 | 0.25 | −0.37 | −0.26 | −0.22 | 2.51 | −0.03 | −1.06 | −0.32 |
| IL-2 | 0.79 | −0.45 | 0.05 | −0.18 | −0.66 | −0.25 | 1.57 | 0.25 | −0.64 | −0.36 |
| IL-8 | 0.00 | −1.95 | −0.18 | −0.36 | −1.05 | −0.92 | 0.56 | −1.05 | −1.74 | −2.03 |
| IL-10 | −0.40 | −1.13 | −1.06 | −1.16 | −0.99 | −1.31 | 0.29 | −0.69 | −1.26 | −1.91 |
| IL-12p35 | 1.06 | 0.16 | 0.15 | 0.05 | −0.29 | 0.49 | 1.64 | 0.80 | −0.45 | −0.39 |
| IL-15 | 1.00 | 0.08 | 0.26 | −0.02 | −0.07 | −0.10 | 1.59 | 1.43 | 0.47 | 0.05 |
| IFNr | 1.59 | 1.48 | 0.93 | 0.57 | 0.10 | −0.08 | 2.27 | 0.87 | 0.11 | −0.17 |
| TNFa | −0.02 | −1.02 | 0.21 | −0.54 | −0.51 | −0.23 | 2.24 | 0.36 | −0.72 | −0.54 |
| CSF1 | −0.07 | −0.75 | 0.19 | 0.06 | 0.62 | −0.24 | 0.23 | 0.58 | 0.31 | 0.43 |
| IL-6 | 1.02 | −0.84 | 1.16 | −0.79 | 0.50 | −0.57 | −0.65 | 1.19 | 0.31 | −0.68 |

|  | N51 NON | N52 NON | N53 NON | N54 NON | N55 NON | N56 NON | N57 NON | N58 NON | N59 NON | N60 NON |
|---|---|---|---|---|---|---|---|---|---|---|
| IL-1a | −0.28 | −0.96 |  | −0.14 | −0.49 | −0.55 | −0.13 | −1.69 | −0.22 | 0.69 |
| IL-1b | 0.09 | −0.73 |  | −0.10 | −0.62 | −0.56 | 0.37 | −0.82 | −0.11 | 0.59 |
| IL-2 | −0.22 | −0.41 |  | 0.33 |  | −0.38 | 1.20 | −0.63 | −0.31 | 0.80 |
| IL-8 | −0.30 | −1.09 | −3.83 | −0.81 | −1.10 | −1.59 | −0.77 | −1.07 | −0.81 | −0.08 |
| IL-10 | −1.31 | −0.97 |  | −0.33 |  | −1.21 | 0.36 | −1.85 | −1.19 | −0.17 |
| IL-12p35 | −0.19 | −0.49 |  | 1.35 |  | −0.11 | 1.21 | −0.93 | −0.18 | 0.30 |
| IL-15 | 0.51 | 0.31 | 0.14 | 1.06 | 2.13 | −0.04 |  | −0.81 | 0.30 | 1.27 |
| IFNr | 0.58 | 1.22 |  | 1.03 |  | 0.27 |  | 0.57 | 0.49 |  |
| TNFa | 0.36 | −0.70 | −3.28 | 0.75 |  | −0.59 | 1.54 | −1.78 | −0.18 | 0.68 |
| CSF1 | 1.13 | 0.21 |  | −0.67 |  | −0.07 | 0.33 | −1.48 | 0.13 | 0.80 |
| IL-6 | 1.51 | 1.59 |  | 0.30 | −0.29 | −0.59 | −0.38 | −0.39 | 0.08 | 0.67 |

|  | N61 NON | N62 NON | N63 NON | N64 NON | N65 NON | N66 NON | N67 NON | N68 NON | N69 MET | N70 MET |
|---|---|---|---|---|---|---|---|---|---|---|
| IL-1a | −1.30 | 0.98 | 1.83 | −1.86 | 0.63 | −0.61 | −0.25 | −0.13 | 0.17 | 1.13 |
| IL-1b | 0.17 | 1.04 | 2.17 | −1.43 | 0.46 | −0.63 | 0.78 | 0.96 | 0.16 | 1.51 |
| IL-2 | 0.41 | 0.95 | 1.66 | −1.54 | 0.44 |  | 0.90 |  | 1.09 | 1.31 |
| IL-8 | −1.52 | 0.47 | 1.02 | −1.69 | −0.41 | −1.80 | 0.06 | −0.10 | 0.40 | 0.58 |
| IL-10 | −0.01 | −0.15 | 0.43 | −2.20 | −1.27 | −0.76 | −0.81 | −0.25 | 0.67 | 1.23 |
| IL-12p35 | 0.81 | 0.61 | 1.53 | −1.16 | 0.83 |  | 0.91 | 0.12 | 0.88 |  |
| IL-15 | 0.87 | 0.86 | 2.04 | −0.51 |  | 0.49 | 1.62 | 1.40 | 1.70 |  |
| IFNr | 1.63 |  | −0.23 |  |  |  | −1.88 | 1.85 | 3.08 | 2.72 |
| TNFa | 0.69 | 1.26 | 1.88 | −0.92 | 0.31 | −1.33 | 1.18 | 0.09 | −0.06 | 2.65 |
| CSF1 | −0.46 | 0.62 | 0.88 | −0.24 | 0.54 | 0.04 | −0.55 | −0.55 | −0.65 | −0.79 |
| IL-6 | −1.52 | 0.96 | 0.91 | −0.14 | 0.34 | 0.25 | 1.03 | 1.23 | −0.34 | 0.14 |

|  | N71 MET | N72 MET | N73 MET | N74 MET | N75 MET | N76 MET | N77 MET | N78 MET | N79 MET | N80 MET |
|---|---|---|---|---|---|---|---|---|---|---|
| IL-1a | 2.07 | 0.77 | −0.69 | −0.96 | 1.31 | −0.52 | −0.54 | −0.99 | −1.82 | 0.76 |
| IL-1b | 2.15 | 2.02 | −0.04 | −0.15 | 0.83 | −0.43 | −0.10 | −0.34 | −1.77 | 1.12 |
| IL-2 | 1.75 | 1.61 | −0.72 | 0.56 | 1.45 | −0.38 | 0.17 | −0.17 | −1.11 |  |
| IL-8 | 0.65 | 1.15 | −0.78 | −1.11 | −0.09 | −0.29 | −0.61 | −0.92 | −2.23 | 1.55 |
| IL-10 | 1.05 | 0.91 | −0.49 | −0.54 | 0.40 | −1.04 | −0.52 | −1.07 | −1.90 | 1.55 |
| IL-12p35 | 2.15 | 1.56 | −0.52 | 0.20 |  | −0.22 | −0.32 | 0.31 |  |  |
| IL-15 |  | 1.81 | 0.15 | 1.33 | 1.29 | 0.41 | 0.30 | 0.43 | 0.09 |  |
| IFNr |  |  |  | 1.64 |  | 0.15 | 0.70 |  | 0.04 |  |
| TNFa | 2.50 | 1.21 | −0.26 | −0.01 | 1.16 | −1.04 | −0.90 | −0.78 | −1.08 | 0.30 |
| CSF1 | −0.08 | 0.31 | −0.17 | 0.20 | −0.44 | −0.83 | −0.70 | −1.05 | −1.13 | −0.14 |
| IL-6 | −0.46 | 1.92 | 1.18 | 1.29 | 1.41 | 1.02 | 1.52 | 0.23 | 0.54 | 1.17 |

TABLE 4

Exemplary classification table for normalized data from tumor tissue.

|  | T1 GOOD | T2 GOOD | T3 GOOD | T4 GOOD | T5 GOOD | T6 GOOD | T7 GOOD | T8 GOOD | T9 GOOD | T10 GOOD |
|---|---|---|---|---|---|---|---|---|---|---|
| IL-1a | −0.61 | −1.00 | −0.91 | −0.51 | −1.47 | −2.08 | −0.46 | −1.26 | −1.69 | −1.81 |
| IL-1b | −0.02 | −0.17 | −0.56 | 0.77 | −1.08 | −0.84 | −0.11 | −0.80 | −1.41 | −1.46 |
| IL-2 | 0.18 | −0.13 | −0.43 | 1.01 | −0.23 | −0.58 | −0.97 | −1.71 | −1.12 | −1.65 |
| IL-8 | −1.43 | −1.57 | −1.86 | 0.40 | −1.74 | −2.19 | −1.05 | −1.14 | −1.50 | −2.32 |

TABLE 4-continued

Exemplary classification table for normalized data from tumor tissue.

| | | | | | | | | | | |
|---|---|---|---|---|---|---|---|---|---|---|
| IL-10 | −0.71 | −0.76 | −0.87 | 0.84 | −1.19 | −0.94 | −0.65 | −0.63 | −1.27 | −1.58 |
| IL-12p35 | 0.23 | −0.54 | 0.59 | 1.17 | −0.36 | −0.48 | −0.19 | −0.20 | −0.42 | −1.08 |
| IL-15 | 0.11 | −0.22 | 0.36 | 0.83 | 0.54 | 0.17 | 0.17 | −0.46 | −0.69 | −0.90 |
| IFNr | 0.75 | 0.20 | 0.38 | 2.01 | 0.71 | 1.10 | 1.68 | −0.05 | −0.19 | −0.85 |
| TNFa | −0.20 | −0.61 | −1.29 | 0.07 | −1.60 | −0.91 | −0.85 | −1.46 | −2.16 | −1.50 |
| CSF1 | −0.37 | −0.11 | −0.89 | −0.84 | −1.63 | 0.15 | 0.51 | 0.24 | −0.71 | −0.52 |
| IL-6 | −1.80 | −1.86 | −1.01 | 1.50 | 0.15 | 0.08 | −1.74 | −0.39 | 0.36 | 0.22 |

| | T11 GOOD | T12 GOOD | T13 GOOD | T14 GOOD | T15 POOR | T16 POOR | T17 POOR | T18 POOR | T19 POOR | T20 POOR |
|---|---|---|---|---|---|---|---|---|---|---|
| IL-1a | −1.74 | −2.43 | 1.03 | 0.73 | 0.63 | −0.53 | −0.21 | −0.48 | 0.63 | 0.33 |
| IL-1b | −1.68 | −1.69 | 2.88 | 0.20 | 0.16 | 0.04 | 0.18 | 0.28 | 0.84 | 1.23 |
| IL-2 | | | 2.04 | 0.87 | 0.68 | 0.60 | −0.05 | 1.47 | 0.68 | 1.17 |
| IL-8 | −2.37 | −1.33 | 0.42 | −0.03 | 0.06 | −0.84 | −0.75 | −0.74 | 0.48 | 0.71 |
| IL-10 | −2.01 | −0.45 | 1.15 | −0.50 | −0.33 | −0.02 | −0.20 | −0.16 | 0.78 | 0.48 |
| IL-12p35 | | −0.59 | 1.56 | 1.10 | 1.55 | 0.76 | 0.94 | 0.81 | 0.26 | 1.48 |
| IL-15 | −0.28 | −0.81 | 2.59 | 2.18 | 1.13 | 1.18 | 0.99 | 1.38 | 1.44 | 2.17 |
| IFNr | | 1.09 | | | 2.00 | 1.94 | 1.81 | 2.38 | 1.53 | 3.06 |
| TNFa | | −2.05 | 1.50 | −0.54 | 0.71 | 0.88 | 0.00 | −0.40 | 1.05 | 0.91 |
| CSF1 | −2.04 | −0.25 | 0.06 | −0.53 | −0.49 | 0.13 | 0.12 | −0.50 | −1.03 | 0.16 |
| IL-6 | −0.40 | −0.59 | 0.24 | 0.20 | −0.06 | −0.83 | −0.50 | −1.43 | 1.57 | 0.29 |

| | T21 POOR | T22 POOR | T23 POOR | T24 POOR | T25 POOR | T26 POOR | T27 POOR | T28 POOR | T29 POOR | T30 POOR |
|---|---|---|---|---|---|---|---|---|---|---|
| IL-1a | −0.46 | 0.22 | −0.87 | 0.82 | −1.78 | −1.37 | −0.71 | −0.69 | 1.47 | 0.16 |
| IL-1b | 0.42 | 0.47 | −0.08 | 1.03 | −0.52 | −0.46 | −0.10 | −0.06 | 0.50 | 0.52 |
| IL-2 | 0.08 | −0.91 | −0.27 | 0.86 | −0.93 | −0.23 | 0.02 | 0.20 | −0.41 | 0.62 |
| IL-8 | −0.56 | 0.24 | −0.83 | −0.08 | −1.53 | −1.58 | −1.19 | 0.10 | −0.94 | 0.05 |
| IL-10 | −0.36 | 0.20 | −0.62 | 1.18 | −0.82 | −1.05 | −0.29 | 0.12 | −0.61 | −0.41 |
| IL-12p35 | 0.66 | −0.48 | −0.61 | 1.63 | −0.61 | 0.02 | −0.13 | 0.43 | 0.79 | 1.32 |
| IL-15 | 0.66 | 0.04 | −0.09 | 1.51 | −1.21 | 0.30 | 0.04 | 0.78 | 0.99 | 1.41 |
| IFNr | 1.13 | 2.11 | 0.45 | | 0.66 | 1.05 | 1.58 | 1.19 | 1.81 | 2.14 |
| TNFa | −0.56 | −0.55 | −0.84 | 0.94 | −1.70 | −0.68 | −0.29 | −0.24 | −0.01 | 0.37 |
| CSF1 | −0.68 | 0.00 | −0.40 | 0.99 | −1.09 | 0.54 | 0.70 | −0.73 | −0.16 | 0.22 |
| IL-6 | −1.08 | −1.13 | −2.67 | −2.35 | −0.83 | −2.12 | −1.36 | 0.41 | −0.08 | −0.52 |

| | T31 POOR | T32 POOR | T33 POOR | T34 POOR | T35 POOR | T36 POOR | T37 GOOD | T38 GOOD | T39 POOR | T40 GOOD |
|---|---|---|---|---|---|---|---|---|---|---|
| IL-1a | −0.13 | 0.03 | −1.08 | −2.50 | −1.13 | 0.30 | −0.95 | −1.00 | | 0.05 |
| IL-1b | 0.18 | 0.85 | −0.74 | −1.81 | −0.67 | 1.23 | −0.71 | −1.20 | −0.76 | −0.11 |
| IL-2 | 0.51 | 0.47 | −0.85 | −1.73 | 0.66 | −0.23 | 0.05 | −1.55 | | −0.77 |
| IL-8 | 0.03 | 0.64 | −0.27 | −2.32 | −0.51 | 1.27 | −1.30 | −1.46 | −0.58 | −1.17 |
| IL-10 | 0.52 | 0.38 | −1.26 | −2.16 | −0.73 | −0.67 | −0.71 | −1.50 | | −1.24 |
| IL-12p35 | 0.74 | 1.39 | 0.22 | −1.51 | −0.05 | −0.85 | −0.05 | −0.77 | | −0.45 |
| IL-15 | 1.15 | 1.19 | 0.50 | −1.33 | −0.02 | 0.22 | −0.02 | −0.03 | | 0.59 |
| IFNr | 1.79 | 0.91 | 0.09 | −0.27 | 2.29 | | 1.95 | | | 0.89 |
| TNFa | −0.15 | 1.21 | −0.58 | −2.72 | −0.33 | −0.06 | −0.92 | −1.48 | | −0.41 |
| CSF1 | −0.02 | 0.97 | −0.65 | −1.28 | −1.05 | −0.70 | −2.22 | −0.30 | −1.41 | −0.42 |
| IL-6 | 0.39 | 0.50 | −0.54 | −1.86 | 0.12 | 0.74 | 1.80 | −0.44 | 0.32 | 0.34 |

| | T41 GOOD | T42 GOOD | T43 GOOD | T44 GOOD | T45 GOOD | T46 GOOD | T47 GOOD | T48 GOOD | T49 GOOD | T50 GOOD |
|---|---|---|---|---|---|---|---|---|---|---|
| IL-1a | −1.25 | −0.89 | −0.03 | −0.44 | −0.18 | 0.20 | 0.92 | −1.23 | | −0.76 |
| IL-1b | −0.63 | −0.46 | 0.62 | −0.27 | 0.27 | −0.34 | 1.60 | −1.07 | −1.34 | 0.08 |
| IL-2 | 0.46 | −0.42 | 0.77 | 0.61 | −0.05 | −0.16 | 1.32 | −1.55 | | −0.53 |
| IL-8 | −1.22 | −1.84 | −0.20 | −0.75 | −0.75 | −1.33 | −0.31 | −1.25 | −1.73 | −0.99 |
| IL-10 | −0.51 | −0.94 | −0.23 | −0.38 | −0.18 | −0.88 | 0.68 | −1.42 | −1.31 | −0.48 |
| IL-12p35 | 0.23 | −0.15 | 1.08 | 0.39 | 0.94 | 0.29 | 1.40 | −1.20 | −1.09 | −0.49 |
| IL-15 | 0.76 | 0.21 | 1.27 | 0.91 | 0.99 | 0.66 | 0.32 | −0.52 | −0.41 | −0.14 |
| IFNr | 1.43 | 0.53 | 1.81 | 1.54 | 1.93 | 0.84 | | 0.38 | | 0.76 |
| TNFa | −0.35 | −0.54 | 0.29 | −0.46 | 0.00 | −0.96 | | −1.14 | −2.54 | −1.04 |
| CSF1 | −0.21 | −0.19 | 0.06 | −0.06 | 0.45 | −0.19 | −0.48 | −1.12 | −0.48 | −0.50 |
| IL-6 | 0.67 | −0.25 | 0.09 | −0.68 | −0.56 | −2.44 | −0.60 | −0.48 | −1.10 | 2.18 |

| | T51 GOOD | T52 GOOD | T53 GOOD | T54 GOOD | T55 GOOD | T56 POOR | T57 POOR | T58 POOR | T59 POOR | T60 POOR |
|---|---|---|---|---|---|---|---|---|---|---|
| IL-1a | −1.15 | −1.17 | | −1.22 | | −0.10 | 0.38 | 0.22 | 0.74 | −0.03 |
| IL-1b | −0.19 | −0.75 | −2.13 | −1.06 | −1.62 | 0.62 | 1.09 | 0.19 | 0.40 | 1.05 |

TABLE 4-continued

Exemplary classification table for normalized data from tumor tissue.

| | | | | | | | | | | |
|---|---|---|---|---|---|---|---|---|---|---|
| IL-2 | −0.60 | −1.24 | −1.48 | 0.19 | | 1.27 | 1.55 | 0.74 | 0.37 | 0.48 |
| IL-8 | −0.61 | −0.59 | −2.73 | −1.25 | −2.02 | −0.36 | 0.24 | −0.16 | −0.51 | −0.20 |
| IL-10 | −0.82 | −1.28 | | −0.74 | −1.59 | 0.37 | 0.97 | −0.40 | −0.25 | 0.56 |
| IL-12p35 | −0.26 | −0.51 | | −0.86 | −0.64 | 1.23 | 1.31 | 0.39 | 0.48 | 1.88 |
| IL-15 | −0.05 | −0.51 | −0.74 | −0.35 | 0.29 | 1.73 | 1.28 | 0.89 | 1.37 | 2.00 |
| IFNr | 0.75 | 0.79 | −0.42 | 0.57 | | 2.88 | 2.06 | 1.63 | 1.78 | 1.84 |
| TNFa | −1.10 | −1.13 | −2.27 | −0.97 | −2.70 | 1.51 | 1.67 | −0.43 | −0.09 | 0.44 |
| CSF1 | −0.78 | 0.30 | | −2.24 | | −0.99 | 0.26 | −0.89 | −0.10 | 1.01 |
| IL-6 | 1.77 | −1.09 | −0.35 | −1.39 | 0.28 | −0.68 | 0.05 | −0.81 | −0.30 | −0.05 |

| | T61 POOR | T62 POOR | T63 POOR | T64 POOR | T65 POOR | T66 POOR | T67 POOR | T68 POOR | T69 POOR | T70 POOR |
|---|---|---|---|---|---|---|---|---|---|---|
| IL-1a | 0.08 | −0.37 | 0.03 | −1.66 | −1.77 | −1.06 | −0.61 | −0.01 | 0.32 | −0.75 |
| IL-1b | 1.58 | −0.07 | −0.08 | −0.17 | −0.73 | −0.94 | 0.42 | −0.08 | 0.33 | 0.11 |
| IL-2 | 1.17 | 0.43 | 0.42 | −0.24 | −1.44 | | 0.27 | −0.74 | 1.12 | 0.38 |
| IL-8 | −0.69 | −1.45 | −1.00 | −0.17 | −1.31 | −1.32 | −0.55 | −0.21 | 0.48 | −0.93 |
| IL-10 | 0.54 | −0.17 | 0.12 | −0.36 | −1.30 | −1.26 | −0.35 | −1.06 | 0.78 | −0.18 |
| IL-12p35 | 1.62 | 0.48 | 1.04 | 0.03 | −1.00 | −1.22 | 0.75 | −0.07 | 0.88 | 0.17 |
| IL-15 | 1.08 | 0.89 | 1.66 | 0.21 | −0.52 | −0.58 | 1.54 | 0.82 | 1.90 | 1.30 |
| IFNr | 1.38 | 1.52 | 1.94 | 1.17 | 0.88 | −0.82 | 2.57 | 0.26 | 2.95 | 1.44 |
| TNFa | 1.69 | −0.07 | 0.78 | −1.03 | −1.94 | −1.51 | −0.48 | 0.08 | −0.03 | 0.51 |
| CSF1 | 0.56 | −0.64 | −0.20 | 1.20 | 0.23 | −0.26 | −1.47 | −0.51 | −0.65 | −0.69 |
| IL-6 | −0.96 | −1.93 | −0.76 | −1.82 | −1.94 | | −0.65 | −0.59 | 0.43 | −0.34 |

| | T71 POOR | T72 POOR | T73 POOR | T74 GOOD | T75 POOR | T76 POOR | T77 POOR | T78 GOOD | T79 POOR | T80 POOR |
|---|---|---|---|---|---|---|---|---|---|---|
| IL-1a | −0.45 | 0.00 | −1.22 | −1.20 | −1.86 | −0.63 | −0.66 | −2.28 | −0.65 | −0.34 |
| IL-1b | −0.48 | 0.39 | 0.14 | −0.51 | −0.66 | 0.50 | 0.20 | −2.13 | −0.31 | −0.19 |
| IL-2 | 0.10 | 0.20 | 0.57 | −0.40 | −0.53 | −0.80 | −0.36 | | −1.11 | 0.67 |
| IL-8 | −0.81 | −0.45 | −0.50 | −1.50 | −1.04 | −0.45 | −1.53 | −1.20 | −0.25 | −0.55 |
| IL-10 | −0.95 | −0.05 | −0.08 | −0.78 | −1.11 | 0.55 | 0.42 | | −1.03 | −0.42 |
| IL-12p35 | 0.51 | 1.20 | 0.63 | 0.10 | −1.09 | −0.05 | 0.36 | −1.00 | −0.02 | 0.56 |
| IL-15 | 1.25 | 0.55 | 0.50 | 0.25 | −0.91 | 0.20 | −0.88 | −0.91 | 0.31 | 0.63 |
| IFNr | 1.19 | 1.66 | 1.26 | 1.57 | 0.49 | 1.37 | 1.68 | | 1.17 | 1.78 |
| TNFa | −0.29 | 0.25 | −0.41 | −1.08 | −1.71 | −1.11 | −0.47 | −2.73 | −0.89 | −0.43 |
| CSF1 | −0.51 | 0.24 | −0.45 | 0.02 | 0.54 | −0.17 | 0.25 | −2.82 | 0.50 | −0.01 |
| IL-6 | −0.36 | −0.74 | 0.00 | 2.21 | −0.84 | 0.42 | −0.55 | | −0.29 | 0.60 |

As shown in FIG. 1B, in a particular example, the non-cancerous and tumor cytokine expression data (raw or normalized), as well as the appropriate classification tables, are inputted, for example into a algorithm that can generate class centroids from the classification table. The classification tables (e.g. Tables 1 and 2 or Tables 3 and 4) are subjected to the algorithm for "training", which provides a type of calibration to generate centroids for each cytokine and each classification (metastasis, non-metastasis, good prognosis, poor prognosis). This provides a classification for metastasis/non-metastasis and good/poor prognosis for known conditions, which can be used to then classify a subject with an unknown prognosis. The algorithm then compares the non-cancerous tissue sample cytokine expression values to known values (e.g. Table 1 or 3) using distance between the sample and the class centroids, and outputs a non-metastasis or metastasis prognosis. The algorithm also compares the tumor tissue sample cytokine expression values to known values (e.g. Table 2 or 4) using distance between the sample and the class centroids. The sample is then classified as a non-metastasis or metastasis and good prognosis or poor prognosis (see Step 3 in FIG. 1B), for example by using the class centroid closest to the expression profile of the sample. Based on the metastasis status and prognosis status determined, the subject is then classified as low risk or high risk of death, for example the likelihood of death within one year, three years, or five years (Step 4, FIG. 1B). An exemplary algorithm that can be used is prediction analysis of microarrays (PAM). The method is described, for example, in Tibshirani et al., *Proc. Nat. Acad. Sci.* 99:6567-62, 2002, incorporated by reference.

In one example, an increased expression of IL-1a, IL-8, and TNF-a in the adenocarcinoma sample (for example relative to a sample from the same organ from a cancer free subject) indicates a poor prognosis for the subject. In another example, increased expression of IL-6, IL-8 and IL-10 in the non-cancerous tissue sample (for example relative to a sample from the same organ of a cancer free subject) indicates poor prognosis for the subject. In an additional example, increased expression of IL-1a, IL-1b, IL-2, IL-6, IL-8, IL-10, IL-12, IL-15, TNF-a and IFN-γ in the non cancerous tissue from the organ as compared to the cancer-free tissue from the organ of one or more control subjects, and decreased expression of CSF-1, indicates a poor prognosis for the subject, such as the tumor with metastasize. In a second example, increased expression of IL-1a, IL-1b, IL-2, IL-6, IL-8, IL-10, IL-12, IL-15, TNF-a, CSF-1 and IFN-γ in the adenocarcinoma as compared to cancer-free tissue from the organ of one or more control subjects indicates a poor survival of the subject. In this example, increased expression can indicate that the subject will survive for less than five years, less than four years, less than two years, or less than one year. In a third example, (1) increased expression of IL-1a, IL-1b, IL-2, IL-6, IL-8, IL-10, IL-12, IL-15, TNF-a and IFN-γ in the non cancerous tissue from the organ as compared to the cancer-free tissue from the organ of one or more control subjects, and decreased expression of CSF-1 in the adenocarcinoma as compared to the cancer-free tissue from the organ of one or more control subjects; and (2), increased expression of IL-1a, IL-1b, IL-2, IL-6, IL-8, IL-10, IL-12, IL-15, TNF-a, CSF-1 and IFN-γ in the adenocarcinoma as compared to cancer-free tissue from the organ of one or more control subjects indicates a poor prognosis for the subject. Thus, the expression indicates that the adenocarcinoma can metastasize and/or indicates a low likelihood of survival of the subject.

In one specific, non-limiting example, the following pattern of cytokine expression is used to determine the prognosis of a subject, wherein such a pattern indicates poor prognosis such as increased likelihood of metastasis and the probability of surviving, such as for about three years, about five years, about 10 years, or longer.

| Cytokine | Noncancerous tissue/Normal control | Cancerous tissue/Normal control |
| --- | --- | --- |
| IL-1a | up-regulated | up-regulated |
| IL-1b | up-regulated | up-regulated |
| IL-2 | up-regulated | up-regulated |
| IL-8 | up-regulated | up-regulated |
| IL-10 | up-regulated | up-regulated |
| IL-12p35 | up-regulated | up-regulated |
| IL-15 | up-regulated | up-regulated |
| IFNr | up-regulated | up-regulated |
| TNFa | up-regulated | up-regulated |
| IL-6 | up-regulated | up-regulated |
| CSF-1 | down-regulated | up-regulated |

In one example, the "normal control" is tissue from the same organ from a control subject, wherein the control subject has not been diagnosed with cancer in that organ, including the cancer of interest. In another example, "normal control" can also be a tissue from the same organ a control subject, wherein the control subject has not be diagnosed with any cancer. In a third example, the "normal control" is healthy, and does not have any known disease process or cancer.

In several examples, the pattern of cytokine expression is used to determine the prognosis of the subject, such to determine if there is a greater than 50% chance that the subject will not survive to a specified time point (such as one, two, three, for or five years), and/or a greater than 50% chance that the tumor will metastasize. The pattern of cytokine expression can be used to determine if there is a poor prognosis for the subject, such that there is a greater than 60%, 70%, 80%, or 90% probability that the subject will not survive and/or a greater than 60%, 70%, 80% or 90% probability that the tumor will metastasize. The pattern of cytokine expression can also be used to determine if there is a good prognosis for the subject, such that there is a greater than 60%, 70%, 80%, or 90% probability that the subject will survive and/or a greater than 60%, 70%, 80% or 90% probability that the tumor will not metastasize.

The adenocarcinoma can be clinically staged in addition to the above assays. Clinical staging can be performed by any method known to one of skill in the art. For example, for a lung cancer, the cancer can be staged using TNM staging.

The methods disclosed herein can be used to determine the prognosis of a subject with any adenocarcinoma of interest, including, but not limited to, lung adenocarcinoma, prostate adenocarcinoma, breast adenocarcinoma, gastric adenocarcinoma, pancreas adenocarcinoma, cervical adenocarcinoma, colon adenocarcinoma or a renal cell adenocarcinoma. In one specific, non-limiting example, a method for determining the likelihood of survival, the likelihood of tumor metastasis, or both for an individual of interest with a lung adenocarcinoma is disclosed herein.

In one example, the method includes quantitating the expression of interleukin (IL)-1a, IL-1b, IL-2, IL-6 IL-8, IL-10, IL-12, IL-15, CSF-1, IFN-γ and tumor necrosis factor (TNF)-a mRNA in a plurality of samples of adenocarcinoma, a plurality of samples of non-cancerous tissue, and in some examples also a plurality of sample of tissue from cancer-free subjects. In one example, the tissue is lung. The plurality of samples of adenocarcinomas and noncancerous tissue is from the same set of subjects with a known clinical outcome, which includes both survival and tumor metastasis. The centroid values of IL-1a, IL-1b, IL-2, IL-6, IL-8, IL-10, IL-12, IL-15, CSF-1 IFN-γ and TNF-a in the plurality of sample of lung adenocarcinoma, the plurality of samples of noncancerous lung tissue, and in some examples also tissue from the cancer-free subjects is calculated.

A numerical value that corresponds to the amount of IL-1a, IL-1b, IL-2, IL-6, IL-8, IL-10, IL-12, IL-15, CSF-1, IFN-γ and TNF-a in the noncancerous tissue and the adenocarcinoma (which is in some examples normalized to the tissue from the cancer-free subjects) is then provided as input to a computer program that provides statistical information, such as PAM. The relationship of the values from the noncancerous tissue and the adenocarcinoma is compared to the centroid values of cytokine expression from subjects with the known clinical outcome (for example using Tables 1 and 2 or 3 and 4), such as metastasis and/or the survival of the subjects.

Thus, following the determination of centroid values, the expression of IL-1a, IL-1b, IL-2, IL-6, IL-8, IL-10, IL-12, IL-15, CSF-1 IFN-γ and TNF-a in a sample of lung adenocarcinoma and noncancerous tissue from the individual of interest is determined. A statistical calculation is then performed to correlate expression of IL-1a, IL-1b, IL-2, IL-6, IL-8, IL-10, IL-12, IL-15, CSF-1 IFN-γ and TNF-a in the adenocarcinoma and non-cancerous sample with the prognosis for the known population. Altered expression of IL-1a, IL-1b, IL-2, IL-8, IL-10, IL-12, IL-15, IFN-γ and TNF-a in the lung adenocarcinoma sample, the noncancerous tissue sample, or both from the individual of interest determines the prognosis for that the individual of interest. Thus, the statistical calculation can determine the likelihood that the individual will not survive five years, the tumor will metastasize, or both. The value from a future (unknown) sample can then be compared to the centroid values.

In another example, a method for determining the likelihood of survival, the likelihood of tumor metastasis, or both for an individual of interest with a lung adenocarcinoma is provided. The method includes quantitating the expression of IL-1a, IL-1b, IL-2, IL-6, IL-8, IL-10, IL-12, IL-15, CSF-1, IFN-γ and TNF-a mRNA in a plurality of samples of lung adenocarcinoma, a plurality of samples of non-cancerous lung tissue, and in some examples also a plurality of samples of lung tissue from cancer-free subjects. The plurality of samples of lung adenocarcinomas and the plurality of samples of noncancerous lung tissue is from the same set of subjects with a known clinical outcome, including both survival and tumor metastasis. A statistical method is used to evaluate the centroid values of IL-1a, IL-1b, IL-2, IL-6 IL-8, IL-10, IL-12, IL-15, CSF-1, IFN-γ and TNF-a in the plurality of samples of lung adenocarcinoma and the plurality of samples of noncancerous lung tissue. The relationship of the centroid values of IL-1a, IL-1b, IL-2, IL-6 IL-8, IL-10, IL-12, IL-15, CSF-1, IFN-γ and TNF-a in the plurality of samples of lung adenocarcinoma and the plurality of samples of noncancerous lung tissue to the known condition of the subject (good prognosis, poor prognosis, metastasis, non-metastasis) is determined. These comparative values are correlated the known clinical outcome is determined, wherein alterations in expression of IL-1a, IL-1b, IL-2, IL-6, IL-8, IL-10, IL-12, IL-15, CSF-1 IFN-γ and TNF-a in the plurality of adenocarcinomas and alterations in expression of IL-1a, IL-1b, IL-2, IL-6, IL-8, IL-10, IL-12, IL-15, CSF-1 IFN-γ and TNF-a in the plurality of noncancerous tissue is correlated with the prognosis of the subjects using a statistical method such as PAM. These values can then be used to validate or predict the clinical outcome of an additional population of subjects.

In one example, an increase in the expression of IL-1a, IL-1b, IL-2, IL-6, IL-8, IL-10, IL-12, IL-15, IFN-γ and TNF-a, and a decrease in the expression of CSF-1 in the noncancerous tissue as compared to the centroid values from tissue from cancer-free subjects indicates the tumor will metastasize. In another example, an increase in the expression of IL-1a, IL-1b, IL-2, IL-6, IL-8, IL-10, IL-12, IL-15, CSF-1, IFN-γ and TNF-a in the plurality of adenocarinma as compared to the centroid values from tissue from cancer-free subjects indicates a poor survival. In yet a further example, alterations in the expression of IL-1a, IL-1b, IL-2, IL-6, IL-8, IL-10, IL-12, IL-15, CSF-1 IFN-γ and TNF-a in the noncancerous tissue as compared to the centroid values from tissue from cancer-free subjects and alterations in the expression of IL-1a, IL-1b, IL-2, IL-6, IL-8, IL-10, IL-12, IL-15, CSF-1 IFN-γ and TNF-a in the plurality of adenocarinma as compared to the centroid values from tissue from cancer-free subjects indicates a poor prognosis for the subject. The comparison of expression of IL-1a, IL-1b, IL-2, IL-6, IL-8, IL-10, IL-12, IL-15, CSF-1 IFN-γ and TNF-a can be performed by any statistical method, including but not limited to PAM.

Screening Test Agents

Methods are disclosed for evaluating the effect of a test anti-cancer agent in a mammalian subject with an adenocarcinoma in an organ, such as a human subject, laboratory animal, or veterinary subject. In one example, the subject is evaluated as described above to determine the prognosis, such as the likelihood of survival and/or the likelihood of metastasis.

The method can include obtaining a first sample of the adenocarcinoma and a first sample of a noncancerous tissue from the organ of the subject prior to administration of the anti-cancer agent. The expression of a plurality of cytokines of interest is evaluated in the first sample of the adenocarcinoma and in the first sample of the noncancerous tissue. The test agent is then administered to the subject, and a second sample of the adenocarcinoma and a second sample of a noncancerous tissue from the organ of the subject is obtained following administration of the test agent. The expression of a plurality of cytokines of interest in the second sample of the adenocarcinoma and the second sample of the noncancerous tissue is evaluated. Altered expression of at least two of IL-1a, IL-1b, IL-2, IL-6, IL-8, IL-10, IL-12, IL-15, CSF-1, IFN-γ and TNF-a, or of all of these cytokines, in the first samples as compared to the second samples in the organ determines if the anti-cancer agent is effective. Altered expression of IL-1a, IL-1b, IL-2, IL-6, IL-8, IL-10, IL-12, IL-15, CSF-1 IFNγ and TNF-a in the adenocarcinoma as compared to the non-cancerous tissue in the organ determines if the anti-cancer agent is effective.

The of plurality cytokines of interest can consist essentially of or consist of IL-1a, IL-1b, IL-2, IL-6, IL-8, IL-10, IL-12, IL-15, CSF-1, IFN-γ and TNF-a. The expression of a control protein (or mRNA encoding the protein), such as ribosomal RNA, can also be evaluated. In some examples, the expression of one or more of IL-4 and IL-5; and/or HLA-DR, HLA-DPA1, ANXA1 and PRG1 is also evaluated.

In one example, decreased expression of IL-1a, IL-8, and TNF-a in the adenocarcinoma as compared to the non-cancerous tissue indicates that the agent is effective for anti-cancer treatment. In another example, decreased expression of IL-6, IL-8 and IL-10 in the non-cancerous tissue as compared to normal tissue indicates that the agent is effective for anti-cancer treatment. In an additional example, decreased expression of IL-1a, IL-1b, IL-2, IL-6, IL-8, IL-10, IL-12, IL-15, TNF-a and IFN-γ in the non cancerous tissue from the organ as compared to the cancer-free tissue from the organ of one or more control subjects, and increased expression of CSF-1, indicates that the agent is effective. In a second example, decreased expression of IL-1a, IL-1b, IL-2, IL-6, IL-8, IL-10, IL-12, IL-15, TNF-a, CSF-1 and IFN-γ in the adenocarcinoma as compared to cancer-free tissue from the organ of one or more control subjects indicates that the agent is effective for the treatment of the subject. In a third example, (1) decreased expression of IL-1a, IL-1b, IL-2, IL-6, IL-8, IL-10, IL-12, IL-15, TNF-a and IFN-γ in the non cancerous tissue from the organ as compared to the cancer-free tissue from the organ of one or more control subjects, and increased expression of CSF-1 in the adenocarcinoma as compared to the cancer-free tissue from the organ of one or more control subjects; and (2), decreased expression of IL-1a, IL-1b, IL-2, IL-6, IL-8, IL-10, IL-12, IL-15, TNF-a, CSF-1 and IFN-γ in the adenocarcinoma as compared to cancer-free tissue from the organ of one or more control subjects indicates that the agent is effective for the treatment of the subject.

Generally, the expression of cytokines, such as IL-1a, IL-1b, IL-2, IL-8, IL-10, IL-12, IL-15, IFNγ and TNF-a can be analyzed using any quantitative method. Once the quantitative values are obtained, any statistical method for the evaluation of class prediction known in the art. These methods include evaluation of t-statistic value (see Golub et al., *Science* 286:531-6, 1999; Hedenfalk et al., *N. Engl. J. Med.* 344:539-48, 2001; Hastie et al., *Genome Biol.* 2:1-12, 2001). One approach to cancer class prediction utilizes nearest shrunken centroids, which identifies the subset of genes that best characterize a calls. This method finds the smallest set of genes that can accurately classify samples. In one example, the statistical method utilized is PAM. A computer program that evaluates shrunken centroids can be downloaded from the Stanford University department of statistics, Tibshirani homepage, from the internet.

Evaluating mRNA

Cytokine expression can be evaluated by detecting mRNA encoding the cytokine of interest. Thus, the disclosed methods can include evaluating mRNA encoding IL-1a, IL-1b, IL-2, IL-6 IL-8, IL-10, IL-12, IL-15, CSF-1 IFN-γ and TNF-a. In some examples, the mRNA is quantitated.

RNA can be isolated from a sample of an adenocarcinoma from an organ of a subject, a sample of a non-cancerous tissue from the organ, from a cancer-free organ from a normal subject, or combinations thereof, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In one example, RNA isolation can be performed using purification kit, buffer set and protease from commercial manufacturers, such as QIAGEN®, according to the manufacturer's instructions. For example, total RNA from cells in culture (such as those obtained from a subject) can be isolated using QIAGIN® RNeasy minicolumns. Other commercially available RNA isolation kits include MASTERPURE®. Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using northern blotting or in situ hybridization (Parker & Barnes, Methods in Molecular Biology 106:247-283, 1999); RNAse protection assays (Hod, Biotechniques 13:852-4, 1992); and PCR-based methods, such as reverse transcription polymerase chain reaction (RT-PCR) (Weis et al., Trends in Genetics 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantitating mRNA are well known in the art. In one example, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700® Sequence Detection System® (Perkin-Elmer-Applied Biosystems, Foster City, Calif.), or Lightcycler (Roche Molecular Biochemicals, Mannheim, Germany). In one example, the 5' nuclease procedure is run on a real-time quantitative PCR device such as the ABI PRISM 7700® Sequence Detection System®. The system includes of thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

In some examples, 5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

A variation of RT-PCR is real time quantitative RT-PCR, which measures PCR product accumulation through a dual-labeled fluorogenic probe (e.g. TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., Genome Research 6:986 994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantitating gene expression using fixed, paraffin-embedded tissues as the RNA source, including mRNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tumor tissue samples or adjacent non-cancerous tissue. The RNA is then extracted, and protein and DNA are removed. Alternatively, RNA is located directly from a tumor sample adjacent non-cancerous tissue. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as mRNA encoding IL-1a, IL-1b, IL-2, IIL-6 IL-8, IL-10, IL-12, IL-15, CSF-1 IFN-γ and TNF-a. Primers that can be used to amplify IL-1a, IL-1b, IL-2, IL-6, IL-8, IL-10, IL-12, IL-15, CSF-1, IFN-γ and TNF-a are commercially available.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "house keeping" gene or "internal control" can also be evaluated. These terms include any constitutively or globally expressed gene whose presence enables an assessment of cytokine mRNA levels. Such an assessment includes a determination of the overall constitutive level of gene transcription and a control for variations in RNA recovery.

In some examples, gene expression is identified or confirmed using the microarray technique. Thus, the expression profile can be measured in either fresh or paraffin-embedded tumor tissue, using microarray technology. In this method, cytokine nucleic acid sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors, and corresponding noncancerous tissue and normal tissues or cell lines.

In a specific embodiment of the microarray technique, PCR amplified inserts of cDNA clones are applied to a substrate in a dense array. At least probes for IL-1a, IL-1b, IL-2, IL-6, IL-8, IL-10, IL-12, IL-15, CSF-1, IFN-γ and TNF-a nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for IL-1a, IL-1b, IL-2, IL-6, IL-8, IL-10, IL-12, IL-15, CSF-1, IFN-γ and TNF-a. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2): 10614-9, 1996). Microarray analysis can be performed by commercially available equipment, following manufacturer's protocols, such as are supplied with Affymetrix GenChip technology, or Incyte's microarray technology.

Serial analysis of gene expression (SAGE) is another method that allows the simultaneous and quantitative analysis of a large number of gene transcripts, without the need of providing an individual hybridization probe for each transcript. First, a short sequence tag (about 10-14 basepairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, for example, Velculescu et al., *Science* 270:484-7, 1995; and Velculescu et al., *Cell* 88:243-51, 1997.

Evaluation of Proteins

In some examples, expression of IL-1a, IL-1b, IL-2, IL-6, IL-8, IL-10, IL-12, IL-15, CSF-1, IFN-γ and TNF-a proteins is analyzed. Suitable biological samples include samples containing protein obtained from an adenocarcinoma of a subject, noncancerous tissue from the subject, and protein obtained from one or more samples of cancer-free subject(s). An alteration in the amount of IL-1a, IL-1b, IL-2, IL-6, IL-8, IL-10, IL-12, IL-15, CSF-1, IFN-γ and TNF-a proteins in an adenocarcinoma and a non-cancerous sample from the subject, such as an increase or decrease in expression, indicates the prognosis of the subject, as described above.

The availability of antibodies specific to IL-1a, IL-1b, IL-2, IL-6, IL-8, IL-10, IL-12, IL-15, CSF-1, IFN-γ and TNF-a proteins facilitates the detection and quantitation of cytokines by one of a number of immunoassay methods that are well known in the art, such as those presented in Harlow and Lane (*Antibodies, A Laboratory Manual*, CSHL, New York, 1988). Methods of constructing such antibodies are known in the art. It should be noted that antibodies to all of these cytokines are available from several commercial sources.

Any standard immunoassay format (such as ELISA, Western blot, or RIA assay) can be used to measure protein levels. A comparison to tissue from an organ of a cancer-free subject can easily be performed. Thus, IL-1a, IL-1b, IL-2, IL-6, IL-8, IL-10, IL-12, IL-15, CSF-1, IFN-γ and TNF-a polypeptide levels in an adenocarcinoma or in noncancerous tissue from the same organ can readily be evaluated using these methods. Immunohistochemical techniques can also be utilized for cytokine detection and quantification. General guidance regarding such techniques can be found in Bancroft and Stevens (*Theory and Practice of Histological*

Techniques, Churchill Livingstone, 1982) and Ausubel et al. (*Current Protocols in Molecular Biology*, John Wiley & Sons, New York, 1998).

For the purposes of quantitating cytokine proteins, a biological sample of the subject that includes cellular proteins can be used. Quantitation of IL-1a, IL-1b, IL-2, IL-6, IL-8, IL-10, IL-12, IL-15, CSF-1, IFN-γ and TNF-a protein can be achieved by immunoassay. The amount IL-1a, IL-1b, IL-2, IL-6, IL-8, IL-10, IL-12, IL-15, CSF-1, IFN-7 and TNF-a protein can be assessed in both the adenocarcinoma and in noncancerous tissue from the same organ can be assessed, and in some examples also in tissue from cancer-free subjects. The amounts in the adenocarcinoma and the noncancerous tissue can be compared to levels of the protein found in cells from a cancer-free subject. A significant increase or decrease in the amount can be evaluated using statistical methods disclosed herein and/or known in the art.

Quantitative spectroscopic approaches methods, such as SELDI, can be used to analyzed IL-1a, IL-1b, IL-2, IL-6, IL-8, IL-10, IL-12, IL-15, CSF-1, IFN-γ and TNF-a expression in a sample (such as non-cancerous tissue, tumor tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as cytokine proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as cytokines) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind IL-1a, IL-1b, IL-2, IL-6, IL-8, IL-10, IL-12, IL-15, CSF-1, IFN-γ and TNF-a. In other examples, the chromatographic surface consists essentially of, or consists of, antibodies that specifically bind IL-1a, IL-1b, IL-2, IL-6, IL-8, IL-10, IL-12, IL-15, CSF-1, IFN-γ and TNF-a. In this context "consists essentially of" indicates that the chromatographic surface does not include antibodies that bind any other cytokines, but can include antibodies that bind other molecules, such as housekeeping proteins (e.g. actin or myosin).

In another example, antibodies are immobilized onto the surface using a bacterial Fc binding support. The chromatographic surface is incubated with a sample, such as a sample of an adenocarcinoma or non-cancerous tissue from the same organ. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems. It should be noted that these values can also be inputted into PAM.

The disclosure is illustrated by the following non-limiting Examples.

EXAMPLES

It has been determined that unique cytokine gene expression signature of noncancerous tissues (such as that surrounding an adenocarcinoma) can be used to classify subjects with an adenocarcinoma into major two groups that reflected the lymph node status and poor survival in hierarchical clustering analysis. In contrast, the cytokine gene signature of lung tumor tissues from the same individuals affected the disease prognosis independent of lymph node metastasis in hierarchical clustering analysis. These results demonstrated that an 11-cytokine gene profile (CLASS-11) of noncancerous and tumor tissue from the same patients had different signatures for carcinogenesis and progression in lung adenocarcinoma. The expression profile of CLASS-11 consists of 11 pro- and anti-inflammatory cytokine genes.

A combined classification algorithm from the prediction of both noncancerous and tumor specimens by 11-gene signature was used to accurately predict the high-risk from the low-risk adenocarcinoma cases. In one example, this 1'-gene signature was used to classify stage I lung adenocarcinoma. This prediction model was confirmed using a validation set. Thus, the experiments described below demonstrate that an 11-cytokine gene signature was a significant independent prognostic factor by multivariate analysis. Therefore, the disclosed CLASS-11 can be used when both noncancerous and tumor tissue are used for the prediction of high-risk stage I adenocarcinoma cases.

Example 1

Methods

This Example provides the methods used in Examples 2-6.

Clinical Samples:

138 pairs of noncancerous and corresponding primary lung tumor tissues from lung adenocarcinoma cases in US were evaluated. All cases had undergone surgical resection in the Baltimore, Md. metropolitan area from 1988 to 1999 with informed consent. Five-year survival information after surgery was available for all patients. All tissue was freshly collected during surgery, snap-frozen, and stored at −80° C. The noncancerous lung tissue was obtained from a minimum of 2 cm away from the tumor to assure that the distant noncancerous lung tissues were free from cancerous cells. Peripheral portions of resected lung tumors were sectioned, stained with hematoxylin-eosin, and evaluated by the study pathologist to confirm that the lung tumors met the histologic criteria for adenocarcinoma according to the 2004 WHO classification (World Health Organization Classification of Tumours, Pathology and Genetics: Tumours of the Lung, Pleura, Thymus and Heart. Lyon: IARC Press; 2004). Patients were excluded if they presented with histological subtypes other than adenocarcinoma (adenosquamous and sarcomatoid or pleomorphic carcinoma with adenocarcinoma component; n=5), samples had less than 50% tumor cell content on the slides (n=1), or were defined by qRT-PCR exclusion criteria as described below (n=52). Therefore, 80 pairs of noncancerous lung tissue and corresponding primary lung tumor tissues from U.S. lung adenocarcinoma patients ultimately were used to identify a gene signature: 53 patients had stage I disease, 20 had stage II disease, six had stage III disease, and one had stage IV disease according to World Health Organization (WHO) TNM (tumor-node-metastasis) staging (Mountain, Chest 111(6): 1710-7, 1997). Normal lung tissue from four cancer-free patients who had undergone surgical resection at the University of Maryland Medical Center from 1996 to 1999 was used as a reference group for each tissue sample; two of the four patients had a smoking history of 20 or more pack-years (one had a bronchial carcinoid, the other had a hamartoma) and the other two patients had a smoking history of less than 20 pack-years (one had a bronchial carcinoid, the other had a fibrous soft tissue tumor).

An independent validation set of tumor and corresponding noncancerous tissue samples were used from 50 Japanese patients with stage I adenocarcinoma who had undergone surgical resection from 1999 to 2003 at the National Cancer Center Hospital (Tokyo) and Hamamatsu University School of Medicine Hospital. Information on patient survival and recurrence during 3 years of follow-up was available for all 50 cases (Table 5).

TABLE 5

Clinical characteristics of US and Japan cases with stage 1.

| Clinical variable | U.S. (n = 53) No. | (%) | Japan (n = 50) No. | (%) | P* |
|---|---|---|---|---|---|
| Age (y) | | | | | |
| <62 | 26 | 49 | 15 | 30 | .07 |
| ≥62 | 27 | 51 | 35 | 70 | |
| Sex | | | | | |
| Male | 25 | 47 | 29 | 58 | .41 |
| Female | 28 | 53 | 21 | 42 | |
| Smoking history (pack-years) | | | | | |
| <20 | 3 | 6 | 32 | 64 | <.001§ |
| ≥20 | 48 | 94 | 18 | 36 | |
| Tumor differentiation | | | | | |
| Well | 14 | 26 | 26 | 52 | .009§ |
| Moderate/Poor | 39 | 74 | 24 | 48 | |
| Subtyping† | | | | | |
| Mixed | 16 | 30 | 35 | 71 | .71 |
| Acinar | 21 | 40 | 3 | 6 | |

TABLE 5-continued

Clinical characteristics of US and Japan cases with stage 1.

| Clinical variable | U.S. (n = 53) No. | (%) | Japan (n = 50) No. | (%) | P* |
|---|---|---|---|---|---|
| Papillary | 6 | 11 | 7 | 14 | |
| Solid | 7 | 13 | 0 | 0 | |
| BAC‡ | 3 | 6 | 4 | 8 | |
| Tumor stage | | | | | |
| IA | 28 | 53 | 28 | 56 | .84 |
| IB | 25 | 47 | 22 | 44 | |
| Survival | | | | | |
| ≥3 years | 38 | 72 | 42 | 84 | .15 |
| <3 years | 15 | 28 | 8 | 16 | |

*Fisher's exact test was used to compare training and test sets
†P-value was calculated between bronchioalveolar adenocarcinoma (BAC) and Non-BAC types
‡Bronchioalveolar adenocarcinoma
§Statistically significant; P-value < 0.05

RNA Isolation and Real-Time Quantitative RT-PCR Analysis:

Total RNA was isolated from the lung tumor and noncancerous lung tissues from the 80 U.S. patients, the lung tumor and noncancerous lung tissues from the 50 Japanese patients, and the normal lung tissue from the four cancer-free patients, with TRIzol (Invitrogen, Carlsbad, Calif.) according to the manufacturer's instructions.

For quantitative reverse transcription-polymerase chain reaction (qRT-PCR) analysis, 3 µg of total RNA was converted to cDNA with random hexamers using SuperScript III First-Strand (Invitrogen) according to the manufacturer's instructions. The expression profiles of 12 cytokine genes (IL-1α, IL-1β, IL-2, IL-4, IL-5, IL-8, IL-1, IL-12p35, IL-12p40, IL-15, IFNγ and TNFα) gene profiles were quantified by using the Taqman Cytokine Gene Expression Plates (Applied Biosystems, Foster City, Calif.). Expression of six genes (interleukin 6 [IL-6], major histocompatibility complex (MHC) class II antigen [DR alpha (HLA-DRA)], MHC class II antigen [DP alpha 1 (HLA-DPA1)], annexin A1 [ANXA1], platelet proteoglycan [PRG1], and colony-stimulating factor [CSF1]) was analyzed using TaqMan Gene Expression assays (Applied Biosystems). Therefore, the gene expression profile contained 18 genes.

Reactions were performed with the ABI PRISM 7700 Sequence Detector System (Applied Biosystems). Human 18S rRNA, labeled with VIC™ reporter dye, was used as an endogenous control. Gene expression was quantified using the comparative method ($2^{-\Delta\Delta C_T}$), where $C_T$=threshold cycle, $\Delta\Delta CT=(C_{T\ cytokine}-C_{T\ 18S\ rRNA})-(C_{T\ reference}-C_{T\ 18S\ rRNA})$, as previously described (Bustin, J. Mol. Endocrinol. 25:169-93, 2000). Gene expression data was excluded for 52 U.S. patients because the average $C_T$ values for the cytokine genes were greater than 35.

Determination of Tissue Cytokine Concentrations:

Protein lysates were prepared by homogenizing 50 mg of lung tumor tissue or noncancerous tissues in 500 µL of tissue homogenizing buffer (50 mM Tris HCl pH 7.6, 150 mM NaCl, 0.1% sodium dodecyl sulfate, 1% Nonidet P-40, and 0.5% sodium-deoxycholate). The homogenates were kept on ice for 30 minutes, then centrifuged at 13000 g for 30 minutes. The supernatant was collected and the protein concentration of the supernatant was measured by a Bradford assay (Bio-Rad, Hemel Hempstead, UK). We determined the protein concentrations of six cytokines (IL-8, IL-1β, IL-2, IL-10, IFNγ, and TNFα) by using cytokine assay kits (Meso Scale Discovery, Gaithersburg, Md.) according to the manufacturer's instructions. Results are expressed as pg of cytokine per mg of total protein.

Statistical Analyses:

Unsupervised hierarchical clustering analysis was performed by Cluster and Tree View (available on the internet from the Stanford University website). For class prediction based on the qRT-PCR profiling, Prediction Analysis of Microarray (PAM), an algorithm for class prediction from gene expression data developed by Tibshirani et al. (*Proc. Natl. Acad. Sci. USA* 99(10):6567-72, 2002), in which classification is based on the nearest shrunken centroid, coupled with 10-fold cross-validation (see below) was used. PAM has been used to classify several types of tumors on the basis of their gene expression profiles (Xi et al., *Clin. Cancer Res.* 11(11):4128-35, 2005; Budhu et al., *Cancer Cell* 10(2):99-111, 2006; Tibshirani et al., *Proc. Natl. Acad. Sci. USA* 99(10):6567-72, 2002). This method is also efficient in finding genes for classification and prediction of cancer. The 80 patients were randomly assigned to training (n=40) and test (n=40) sets for cross-validation analysis. These two cohorts had similar clinical profiles (Table 6).

TABLE 6

Clinical characteristics of two cohorts in U.S. 80 patients

| Clinical variable | Training set (n = 40) | | Test set (n = 40) | | P* |
|---|---|---|---|---|---|
| | No. | % | No. | % | |
| Age (y) | | | | | |
| <62 | 21 | 53 | 15 | 38 | .26 |
| ≥62 | 19 | 48 | 25 | 63 | |
| Sex | | | | | |
| Male | 18 | 45 | 22 | 55 | .50 |
| Female | 22 | 55 | 18 | 45 | |
| Race | | | | | |
| White | 30 | 75 | 32 | 80 | .60 |
| Black | 10 | 25 | 8 | 20 | |
| Smoking history (pack-years) | | | | | |
| <20 | 1 | 3 | 7 | 18 | .06 |
| ≥20 | 36 | 97 | 32 | 82 | |
| Tumor differentiation | | | | | |
| Well | 7 | 18 | 13 | 33 | .19 |
| Moderate/Poor | 33 | 83 | 27 | 68 | |
| Lymph node status | | | | | |
| N0 | 28 | 70 | 28 | 70 | .00 |
| N1-2 | 12 | 30 | 12 | 30 | |
| TNM stage | | | | | |
| I | 27 | 68 | 26 | 65 | .82 |
| II, III, IV | 13 | 33 | 14 | 35 | |
| Survival | | | | | |
| ≥5 years | 17 | 43 | 17 | 43 | .00 |
| <5 years | 23 | 58 | 23 | 58 | |

*Fisher's exact test was used to compare training and test sets

Kaplan-Meier survival analysis was used to compare patient survival for 79 of the 80 US cases investigated (one patient died during the surgery; that patient's survival time was 0 days). The resulting survival curves were compared with one another using the Cox-Mantel log-rank test. Due to the sample size of the Japanese cohort, the resulting survival curves were compared using the Wilcoxon log-rank test, a test statistic that gives more weight to differences between the survival curves at smaller values of time. Cox proportional hazards modeling (univariate and multivariate tests) was used to analyze the effect of six clinical variables (age, sex, race, smoking status, histologic differentiation, and TNM stage) on patient survival. Both of the final models met the proportional hazards assumption as determined by Schoenfeld residuals. Kaplan-Meier survival analysis was performed using GraphPad Prism 4 (Aurona, Colo.) and verified with STATA 9.1 (College Station, Tex.). Cox proportional hazards modeling was performed using STATA 9.1 and statistical significance was defined as a p-value<0.05. The Wilcoxon matched pairs signed-rank test (in Prism 4 software) was used to compare the protein expression between tumor and noncancerous tissues. All statistical tests were two-sided, and statistical significance was defined as P less than 0.05.

Univariate Cox proportional hazards regression was used to investigate the individual relationship of the CLASS-11 and six clinical variables on survival, including age, gender, race, smoking status, histological differentiation, and TNM staging. TNM stage was categorized into two groups: Stage I representing non-invasive, non-metastatic tumors and Stage II, III and IV representing invasive tumors or tumors positive for node and/or distant metastasis. Age and smoking status were dichotomized into two groups of <62 and ≥62 years old and <20 and ≥20 pack year, respectively. The multivariate analysis was used to estimate the hazards ratio of CLASS-11 while controlling for the effects of clinical covariates which were identified, in a stepwise fashion, by both forward variable addition and backward variable elimination. The CLASS-11 was locked into the model and the significance was set at a p-value less than 0.05 or greater than 0.05 for the forward variable addition and backward variable elimination, respectively, to generate the most parsimonious model. In the all case model, both selection methods identified TNM stage as a necessary covariate; whereas in the stage I case model, race and histological differentiation and TNM stage (dichotomized as Stage IA and IB) were identified. Additionally, a criterion of a 10% change in the hazards ratio for CLASS-11 with the addition of a single covariate to the model containing CLASS-11 alone was used to assess potential confounding by covariates. In both the all case and stage I case models, TNM stage was identified as a confounder. Therefore, the final all case model included CLASS-11 and TNM stage. The stage I case model included the CLASS-11, race, histological differentiation, and TNM stage. Potential collinearity of variables was assessed and found not to be present. Furthermore, it was determined that both final models met the proportional hazards assumption.

Figure 3A:
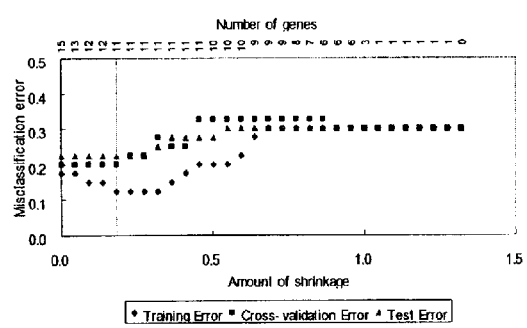
FIGS. 3A-3B are graphs showing the misclassification error rates of lymph node classification (A) and prognosis prediction (B) of during the reduction of the signature gene number is shown as a function of the threshold parameter. The threshold level cut off of 0.18 was chosen and yields a subset of 11 genes for classifying the lymph node status. The threshold of 0.39 (11 genes) was used as a classification cutoff for the prognosis prediction.
Figure 3B:
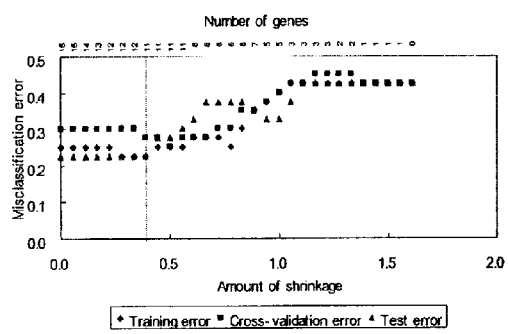
Figure 3C:
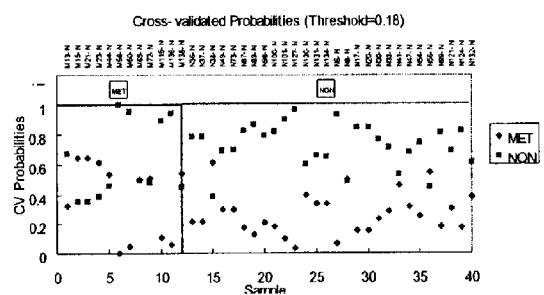
FIGS. 3C-3D are graphs showing the classification probability of lymph node status (C) and prognosis (D) by PAM for the training cohort. Samples are partitioned by the pathological diagnosis (Upper) and the PAM prediction (Lower).
Figure 3D:
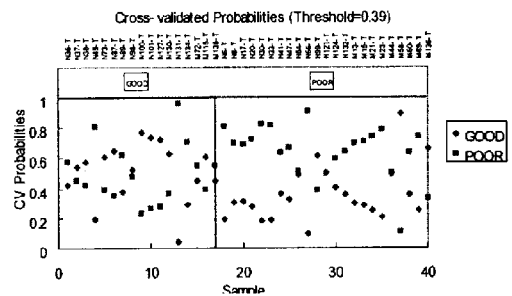

Minimization of the 15-Gene Signature by PAM:

The 15-gene signature was refined by minimizing the number of genes required for accurate class prediction. The misclassification error rate increased dramatically when a single signature gene was used during cross-validation (FIGS. 3A and 3B). The same prediction accuracy was maintained when the 11 most differentially expressed signature genes were used; therefore, 11 genes were a suitable number for lymph node and prognosis prediction. A threshold of 0.18 with 11 genes yielded 96% correct prediction for N0 and 58% of N+, respectively (FIG. 3C). A threshold of 0.39 with 11 genes yielded 59% correct prediction for SHORT and 83% of GOOD, respectively (FIG. 3D).

Example 2

Hierarchical Clustering Analysis of Paired Non-Cancerous Lung Tissue and Corresponding Lung Adenocarcinoma Using 15-Cytokine Expression Profile To investigate the role of the lung environment in promoting metastasis, the 18-cytokine gene expression profile was analyzed in noncancerous lung tissue from the 80 US lung adenocarcinoma. Seventeen of these genes were previously shown to be part of a unique inflammation/immune response-related signature in noncancerous hepatic tissue from hepatocellular carcinoma (HCC) patients, which could discriminate HCC with metastasis from HCC without metastasis (Budhu et al. *Cancer Cell* 10:99-111, 2006). The signature also contained a multifunctional cytokine IL-6 gene, which was predominantly expressed in tumor-infiltrating lymphocytes and normal bronchial epithelial cells in lung cancer (Takizawa et al., *Cancer Res.* 53:4175-81, 1993; Asselin-Paturel et al. *Int. J Cancer* 77:7-12, 1998). Previous studies reported high circulating levels of IL-6 are associated with a rapid progression of disease and poor survival in lung cancer patients (De Vita et al., *Oncol. Rep.* 5:649-52, 1998; Yanagawa et al. *Br. J Cancer* 71:1095-8, 1995).

The IL-4, IL-5, and IL-12p40 genes were eliminated from the 18-gene profile because their expression was detected in only 24 (30%), 20 (25%), and 26 (33%) noncancerous lung tissue samples, respectively. The profile was reduced to 15 genes whose expression was detected in more than 70% of the noncancerous lung tissue cases.

Unsupervised hierarchical clustering analysis of the 80 noncancerous lung tissue samples, which was based on the similarities in expression patterns of the 15-gene panel, resulted in a clear separation into two clusters, namely cluster A (n=31) and cluster B (n=49). An examination of the relationship between the two clusters and patient and tumor characteristics revealed statistically significant differences between cluster A and cluster B with respect to lymph node metastasis status (N0 versus N1-2; P=0.002, Fisher's exact test) and TNM stage (stage I versus stages II-IV; P=0.002, Fisher's exact test) (Table 7). Only one case with distant metastasis (M1) was included among the 80 U.S. cases. Therefore, the 15-cytokine gene signature was not influenced by distant metastasis status (M0 versus M1). These results indicate that the 15-cytokine gene signature of noncancerous tissue reflected primarily the lymph node status (metastasis versus no metastasis) of these 80 patients. However, there was no statistically significant difference in overall survival between the patients in the two clusters (Table 7 and FIG. 2B).

TABLE 7

Clinicopathologic characteristics of the 80 U.S. adenocarcinoma cases by unsupervised hierarchical cluster group

| Clinical variable | Cluster A (n = 31) | | Cluster B (n = 49) | | | Cluster C (n = 40) | | Cluster D (n = 40) | | |
|---|---|---|---|---|---|---|---|---|---|---|
| | No. | (%) | No. | (%) | P* | No. | (%) | No. | (%) | P* |
| Age (y)† | | | | | | | | | | |
| <62 | 16 | (52) | 20 | (41) | .36 | 20 | (50) | 16 | (40) | .50 |
| ≥62 | 15 | (48) | 29 | (59) | | 20 | (50) | 24 | (60) | |
| Sex | | | | | | | | | | |
| Male | 13 | (42) | 27 | (55) | .26 | 16 | (40) | 24 | (30) | .12 |
| Female | 18 | (58) | 22 | (45) | | 24 | (60) | 16 | (70) | |
| Race | | | | | | | | | | |
| White | 24 | (77) | 38 | (78) | 1.00 | 32 | (80) | 30 | (75) | .61 |
| Black | 7 | (23) | 11 | (22) | | 8 | (20) | 10 | (25) | |
| Smoking history (pack-years)‡ | | | | | | | | | | |
| <20 | 2 | (6) | 6 | (13) | .46 | 3 | (8) | 5 | (13) | .71 |
| ≥20 | 29 | (94) | 39 | (87) | | 34 | (92) | 34 | (87) | |
| Tumor differentiation | | | | | | | | | | |
| Well | 6 | (19) | 14 | (29) | .57 | 8 | (20) | 12 | (30) | .31 |
| Moderate/Poor | 25 | (81) | 35 | (71) | | 32 | (80) | 28 | (70) | |
| Lymph node status | | | | | | | | | | |
| N0 | 28 | (90) | 28 | (57) | .002 | 26 | (65) | 30 | (75) | .34 |
| N1-2 | 3 | (10) | 21 | (43) | | 14 | (35) | 10 | (25) | |
| TNM stage§ | | | | | | | | | | |
| I | 27 | (87) | 26 | (53) | .002 | 23 | (58) | 30 | (75) | .10 |
| II, III, or IV | 4 | (13) | 23 | (47) | | 17 | (43) | 10 | (25) | |
| Survival‖ | | | | | | | | | | |
| ≥5 years | 17 | (55) | 17 | (35) | .14 | 11 | (28) | 23 | (58) | .01 |
| <5 years | 14 | (45) | 32 | (65) | | 29 | (73) | 17 | (43) | |

*P values are for cluster A versus cluster B or for cluster C versus cluster D (Fisher's exact test, two-sided).
†Age was dichotomized into two groups based on the median age (62 years).
‡Smoking history of four cases was unknown. The population was divided into two groups according to the classification of our previous lung study (52).
§Tumor-Node-Metastasis (TNM) classification according to the World Health Organization TNM staging system (2).
‖Survival at 5 years was chosen as a cut-off point according to the primary end point of adjuvant chemotherapy study (48).

To evaluate the cytokine profile of the primary tumors, the 15-cytokine gene panel of the corresponding lung tumor tissue was analyzed from the same 80 individuals. Unsupervised hierarchical clustering analysis divided the corresponding 80 lung cancer tissues into two different clusters consisting of 40 cases of cluster C and 40 cases of cluster D. There were no statistically significant differences between clusters C and D with respect to lymph node metastasis status or TNM stage (Table 7). However, survival status (≥5 years versus <5 years) was statistically significantly different between clusters C and D (P=0.01; Table 7), as were the Kaplan-Meier curves for overall survival (P=0.009) (FIG. 2C).

Figure 2A:
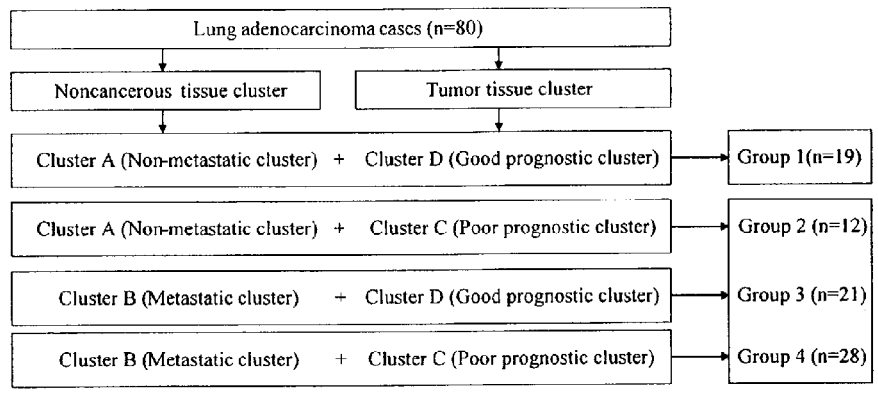
FIGS. 2A-2E are graphs and schematic diagrams showing a cytokine gene expression profile of 15 genes and its association with prognosis. (A) The four cluster groups representing the noncancerous and tumor tissue cluster patterns of each patient. Non-metastatic cluster=Cluster of patients with a low risk of lymph node metastasis. Metastatic cluster=Cluster of patients with a high risk of lymph node metastasis. Good prognostic cluster=Cluster of patients likely to have long survival. Poor prognostic cluster=Cluster of patients likely to have short survival. (B) Kaplan-Meier analysis of overall survival for cluster A versus cluster B. (C) Kaplan-Meier analysis of overall survival for cluster C versus cluster D. (D) Kaplan-Meier analysis of overall survival for four cluster groups based on the cluster pattern of the noncancerous lung tissue and the lung tumor tissue of each patient. (E) Kaplan-Meier analysis of overall survival for patients with stage I disease in the four cluster groups based on the cluster pattern of the noncancerous lung tissue and the lung tumor tissue of each individual P values were calculated by the Cox-Mantel log-rank test; statistical significance was defined as P<0.05.
Figure 2B:
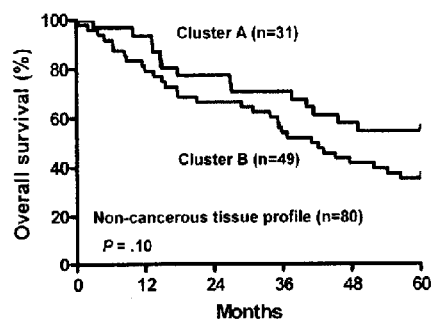

The 80 cases were divided into four cluster groups representing the noncancerous and tumor tissue cluster pattern of each individual (FIG. 2A). Group 1 (n=19) comprised patients whose noncancerous lung tissue was in cluster A (nonmetastatic) and whose tumor tissue was in cluster D (good prognosis); these patients were categorized as being at low risk of death. In contrast, groups 2-4 (n=61) comprised patients whose noncancerous lung tissue was in cluster B (metastatic) and/or whose tumor tissue was in cluster C (poor prognosis); these patients were categorized as being at high risk of death.

Figure 2C:
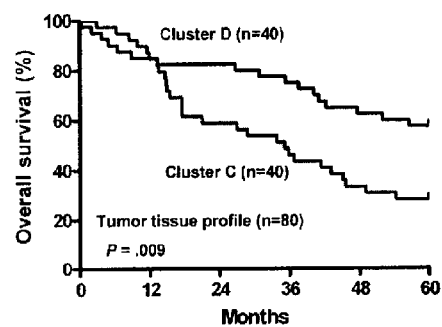
Figure 2D:
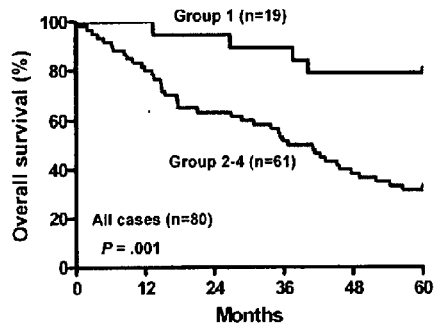
Figure 2E:
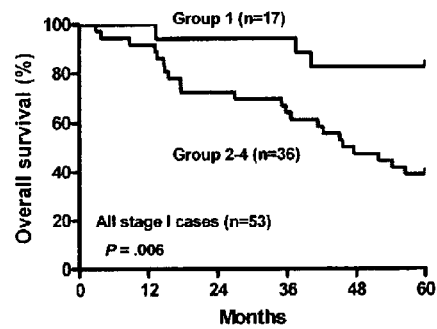

Kaplan-Meier survival analysis revealed that the 5-year overall survival rate for patients in groups 2-4 was statistically significantly less than that of patients in group 1 [32% versus 79%, difference=47%, 95% CI=25% to 69%), P=0.001] (FIG. 2C). When the analysis to patients with stage I adenocarcinoma (n=53), the 5-year overall survival rate for patients in groups 2-4 (n=36) was still statistically significantly less than that of patients in group 1 (n=17) (39% versus 82%, difference=43%, 95% CI=19% to 67%, P=0.006] (FIG. 2E). These results indicate that the combination of the 15-cytokine gene profile of the noncancerous lung tissue with that of lung tumor tissue from the same individual is strongly associated with disease outcome, even in stage I cases.

Example 3

Association Between 15-Cytokine Gene Expression Profile and Lymph Node Metastasis and Prognosis in Lung Adenocarcinoma This example describes use of the PAM cross-validation algorithm to demonstrate the ability of the 15-cytokine gene profile of noncancerous tissue to classify patients for lymph node metastasis (N0 versus N1-2).

The 80 US patients were randomly distributed in training (n=40) and test (n=40) sets for this cross-validation analysis. Overall, the PAM classification of the 15-cytokine gene profile using a threshold value of 0.00 correctly identified the lymph node status of 32 (80%) of 40 cases in the training set (Table 8). Furthermore, patients with lymph node metastasis (n=24) expressed statistically significantly higher levels of five cytokine genes (IL-10, IL-8, IL-6, IL-2, and IFN-γ) than cases with no nodal metastasis (n=56) (Table 9). Of those five genes, those encoding cytokines IL-10, IL-8, and IL-6 were the top three genes for discriminating cases with lymph node metastasis from cases without metastasis by PAM ranking.

TABLE 8

Misclassification error rates during reduction of signature gene number

| Number of Genes | Threshold | Training* | Cross-validation† | Test‡ |
|---|---|---|---|---|
| a. Prediction accuracy of lymph node status by PAM analysis | | | | |
| 15 | 0.00 | 0.18 | 0.20 | 0.23 |
| 13 | 0.05 | 0.18 | 0.20 | 0.23 |
| 12 | 0.09 | 0.15 | 0.20 | 0.23 |
| 11 | 0.18 | 0.13 | 0.20 | 0.23 |
| 10 | 0.50 | 0.20 | 0.33 | 0.28 |
| 9 | 0.64 | 0.28 | 0.33 | 0.30 |
| b. Prediction accuracy of prognosis by PAM analysis | | | | |
| 15 | 0.00 | 0.25 | 0.30 | 0.23 |
| 14 | 0.11 | 0.25 | 0.30 | 0.23 |
| 13 | 0.17 | 0.25 | 0.30 | 0.23 |
| 12 | 0.33 | 0.23 | 0.30 | 0.23 |
| 11 | 0.39 | 0.23 | 0.28 | 0.23 |
| 8 | 0.61 | 0.28 | 0.28 | 0.33 |

*Training misclassification error rates by PAM for 40 training set
†Cross-validated misclassification error rates by PAM for 40 training set
‡Test misclassification error rates by PAM for 40 test set PAM classification of the 15-cytokine gene profile from corresponding lung tumor tissue was able to classify patients according to 5-year survival. Overall, PAM classification of the 15-cytokine gene profile using a threshold value of 0.00 correctly classified outcomes in 28 (70%) of the 40 cases in the training cohort (Table 8). Of the 15 cytokine genes, nine (IL-10, IL-8, TNFα, IL-1α, IL-15, IL-2, IFN-γ, IL-β, and IL-12p35) were expressed at statistically significantly lower levels (P<0.05 to P<0.001) in the lung tumor tissue of patients who survived for at least 5 years (n=34) than in patients who survived for fewer than 5 years (n=56) (Table 9). Of the nine genes, IL-8, TNFα and IFNγ and had the highest fold differences in expression between patients who survived for at least 5 years versus those who survived for fewer than 5 years (4.2, 3.9, and 5.4, respectively). In the PAM analysis, these genes were the top three genes that contributed to survival by PAM ranking. The gene expression products of these genes have potential angiogenic activities in several cancers including NSCLC (Smith et al., J. Exp. Med. 179, 1409-15, 1994). These results indicate that increased levels of IL-8 and TNFα can contribute to poor survival through their angiogenic properties.

TABLE 9

Prediction Analysis of Microarray (PAM) ranking of contributions of 15 cytokine genes to lymph node metastasis and prognosis*

| | | Gene expression in noncancerous lung tissue | | | Gene expression in lung tumor tissue | | |
|---|---|---|---|---|---|---|---|
| Gene symbol | Unigene ID | Fold difference (N+/N0) | P† (N+ vs N0) | PAM ranking‡ (MET vs NON) | Fold difference (SHORT/LONG) | P† (SHORT vs LONG) | PAM ranking§ (POOR vs GOOD) |
| IL-10 | Hs.193717 | 11.6 | .003 | 1 | 1.7 | <.001 | 7 |
| IL-8 | Hs.624 | 3.0 | .003 | 2 | 4.2 | <.001 | 1 |

TABLE 9-continued

Prediction Analysis of Microarray (PAM) ranking of contributions of 15 cytokine genes to lymph node metastasis and prognosis*

| | | Gene expression in noncancerous lung tissue | | | Gene expression in lung tumor tissue | | |
|---|---|---|---|---|---|---|---|
| Gene symbol | Unigene ID | Fold difference (N+/N0) | P† (N+ vs N0) | PAM ranking‡ (MET vs NON) | Fold difference (SHORT/LONG) | P† (SHORT vs LONG) | PAM ranking§ (POOR vs GOOD) |
| IL-6 | Hs.512234 | 2.0 | .007 | 3 | 0.3 | .29 | 10 |
| TNFα | Hs.241570 | 6.4 | .12 | 4 | 3.9 | <.001 | 2 |
| IL-1α | Hs.1722 | 2.1 | .07 | 5 | 1.7 | .01 | 5 |
| IL-15 | Hs.311958 | 4.0 | .06 | 6 | 1.0 | .002 | 9 |
| IL-2 | Hs.89679 | 4.7 | .03 | 7 | 2.1 | .02 | 6 |
| IFNγ | Hs.856 | 9.1 | .02 | 8 | 5.4 | <.001 | 3 |
| IL-12p35 | Hs.673 | 5.4 | .15 | 9 | 2.3 | .007 | 8 |
| IL-1β | Hs.126256 | 1.8 | .13 | 10 | 2.0 | <.001 | 4 |
| CSF1 | Hs.173894 | 0.7 | .07 | 11 | 2.0 | .35 | 11 |
| HLA-DRA | Hs.520048 | 1.0 | .59 | 12 | 1.0 | .55 | 15 |
| PRG1 | Hs.1908 | 1.0 | .18 | 13 | 2.0 | .22 | 13 |
| HLA-DPA1 | Hs.347270 | 0.9 | .76 | 14 | 0.3 | .82 | 14 |
| ANXA1 | Hs.494173 | 1.0 | .76 | 15 | 0.6 | .49 | 12 |

*Fold differences were calculated based on the average value for each cluster group. N+ = cases with lymph node metastasis; N0 = cases without lymph node metastasis; MET = cases with lymph node metastasis predicted by PAM; NON = cases without lymph node metastasis predicted by PAM; LONG = cases with long survival (≥5 years); SHORT = cases with short survival (<5 years); POOR = Poor-prognosis cases predicted by PAM; GOOD = Good-prognosis cases predicted by PAM.
†Two-sided Mann-Whitney U test.
‡Genes were ranked according to their contribution to lymph node metastasis by PAM classification
§Genes were ranked according to their contribution to prognosis by PAM classification Cytokines IL-10, IL-8 and IL-6 were the most informative for discrimination of lymph node metastasis (MET) cases from nonmetastatic (NON) cases in the PAM analysis. Therefore, it appears that a Th2 cytokine dominant expression pattern occurs in noncancerous tissue and may mediate metastasis, indicating involvement of the humoral immune response.

Example 4

Construction of the CLASS-11 Prognosis Predictor

The PAM analysis showed excellent performance of the gene signature in noncancerous tissue as a lymph node status classifier. This example describes methods used to identify the smallest number of cytokine genes whose expression could accurately classify lung adenocarcinoma patients according to lymph node status.

Using 10-fold cross-validation by PAM, both the cross-validated and test errors were minimized near a shrinkage value of 0.18 (Table 9; FIG. 3A). The value 0.18 yielded a subset of 11 selected genes. The top 11 genes (IL-10, IL-8, IL-6, TNFα, IL-1α, IL-15, IL-2, IFN-γ, IL-1β, IL-12p35, and CSF1) according to the PAM ranking were subsequently found to be the minimum number necessary for lymph node classification. Overall, PAM classification of these 11 genes correctly identified the lymph node status of 32 (80%) of the 40 cases in the training set (Table 8; FIG. 3C). In addition, these 11 genes were also the optimal number of genes for prognostic classification (at a shrinkage value of 0.39) (Table 9; FIG. 3B). Overall, PAM classification of the 11 genes correctly classified prognosis in 29 (73%) of the 40 cases in the training set (Table 10; FIG. 3D). This gene expression signature is referred to as the Cytokine Lung Adenocarcinoma Survival Signature of 11 genes (CLASS-11).

TABLE 10

Prediction abilities of CLASS-11

| | No. | PAM classification | No. | Accuracy (%) |
|---|---|---|---|---|
| a. Prediction accuracy of lymph node status by PAM analysis Training set (n = 40) | | | | |
| Pathology | | | | |
| N0* | 28 | NON‡ | 25 | 25/28 (96%) |
| | | MET§ | 3 | |
| N+† | 12 | MET§ | 7 | 7/12 (58%) |
| | | NON‡ | 5 | |
| Total | 40 | | 40 | 32/40 (80%) |
| N0* | 28 | NON‡ | 26 | 26/28 (93%) |
| | | MET§ | 2 | |
| N+† | 12 | MET§ | 5 | 5/12 (42%) |
| | | NON‡ | 7 | |
| Total | 40 | | 40 | 31/40 (78%) |
| b. Prediction accuracy of prognosis by PAM analysis Training set (n = 40) | | | | |
| Survival of cases | | | | |
| LONG‖ | 17 | GOOD** | 10 | 10/17 (59%) |
| | | POOR†† | 7 | |
| SHORT¶ | 23 | POOR†† | 19 | 19/23 (83%) |
| | | GOOD** | 4 | |
| Total | 40 | | 40 | 29/40 (73%) |
| Test set (n = 40) Survival of cases | | | | |
| LONG‖ | 17 | GOOD** | 11 | 11/17 (65%) |
| | | POOR†† | 6 | |
| SHORT¶ | 23 | POOR†† | 20 | 20/23 (87%) |
| | | GOOD** | 3 | |
| Total | 40 | | 40 | 31/40 (78%) |

Figure 3E:
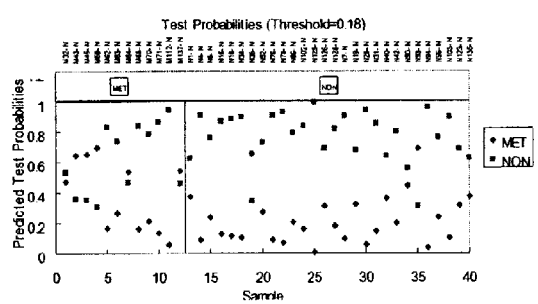
FIGS. 3E-3F are graphs showing the classification probability of lymph node status (E) and prognosis (F) by PAM for the test cohort. Samples are partitioned by the pathological diagnosis (Upper) and the PAM prediction (Lower).
Figure 3F:
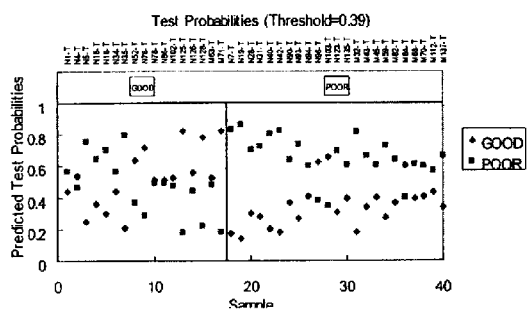

†Cases with lymph node metastasis
‡Negative lymph node metastasis group classified by Prediction analysis of Microarray (PAM) analysis
§Positive lymph node metastasis group classified by PAM analysis
‖Cases with long term survival (≥5 years)
¶Cases with short term survival (<5 years)
**Good prognosis group classified by PAM analysis
††Poor prognosis group classified by PAM analysis CLASS-11 genes were tested using a validation cohort of 40 patients. PAM classification revealed that CLASS-11 correctly predicted both lymph node status and prognosis in 31 (78%) of the 40 patients (Table 10 and FIGS. 3E and 3F). PAM classification of CLASS-11 was performed for all 80 U.S. adenocarcinoma cases. Consistently, CLASS-11 correctly predicted lymph node status in 63 (79%) of the 80 patients and prognosis in 60 (75%) of the 80 patients.

Figure 4:
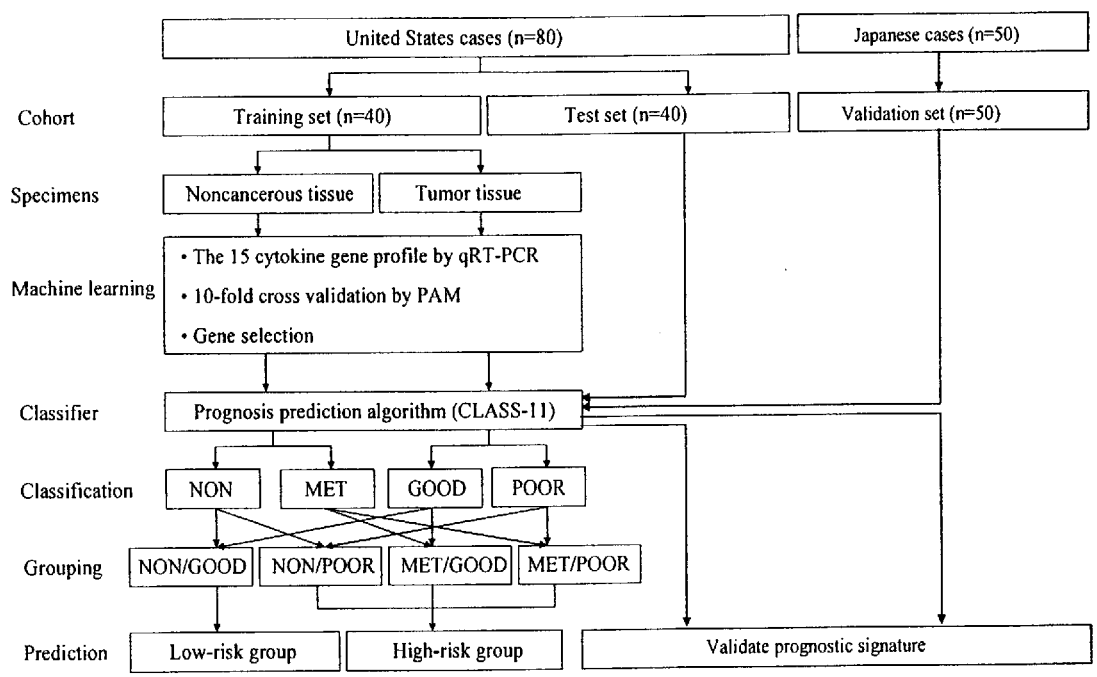
FIG. 4 is a schematic diagram of the development of the Cytokine Lung Adenocarcinoma Survival Signature of 11 genes (CLASS-11) classifier and presents an overview of the approach used for development and validation of a prognosis predictor based on CLASS-11. qRT-PCR=Real-time quantitative reverse transcription-polymerase chain reaction. PAM=Prediction analysis of Microarray. NON=Non lymph node metastasis cases predicted by PAM. MET=Lymph node metastasis cases predicted by PAM. GOOD=Good prognosis cases predicted by PAM. POOR=Poor prognosis cases predicted by PAM.
Figure 5A:
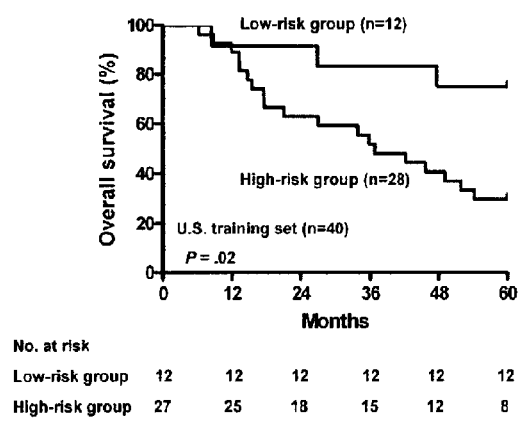
FIGS. 5A-5F are a set of graphs showing Kaplan-Meier curves by CLASS-11 risk group. (A) Overall survival among the cases in the 40 U.S. patients assigned to the training cohort, according to the two survival risk groups. (B) Overall survival among the cases in the U.S. test cohort. (C) Overall survival among all 80 U.S. patients. (D) Overall survival among all 53 U.S. stage I patients. P values for A-D were calculated by the Cox-Mantel log-rank test and statistical significance was defined as P<0.05. (E) Overall survival among the independent cohort of Japanese stage I cases, according to the two survival risk groups. (F) Disease-free survival among the cases in the Japanese cohort. P values for E and F were calculated by the Wilcoxon log-rank test; statistical significance was defined as P<0.05.
Figure 5B:
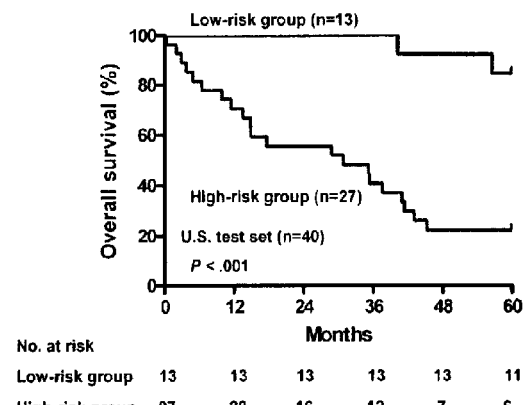

Based on the results of the clustering analyses of non-cancerous tissue and the lung tumor tissues, a combination of the two PAM classifiers (i.e., lymph node status classifier and prognosis classifier) was used to improve the prognostic classification by CLASS-11 for potential future clinical application (FIG. 4). CLASS-11 classified the 40 cases in the training set into one of two survival risk groups: the low risk of death group or high risk of death group. The low risk of death group (n=12 cases) comprised patients whose non-cancerous lung tissue was classified by PAM as no lymph node metastasis (i.e., NON) and whose tumor tissue was classified by PAM as good prognosis (i.e., GOOD). The high risk of death group (n=28 cases) comprised patients whose noncancerous lung tissue was classified by PAM as lymph node metastasis (i.e., MET) and/or whose tumor tissue was classified by PAM as poor prognosis (i.e., POOR). The 5-year survival rates were 75% (95% CI=41% to 91%) for the low risk of death group and 30% (95% CI=14% to 47%) for the high risk of death group. Kaplan-Meier survival analysis showed that the high risk group had statistically significantly worse survival than the low risk group (P=0.02) (FIG. 5A). Subsequent evaluation of the predictive power of CLASS-11 in the test set classified the 40 cases into a high risk of death group (n=27 cases) or the low risk of death group (n=13 cases). The high risk group had statistically significantly worse survival than the low-risk group (P=0.001) (FIG. 5B). The 5-year survival rates were 85% (95% CI=51% to 96%) in the low risk of death group and 22% (95% CI=9% to 39%) in the high risk of death group.

Figure 5C:
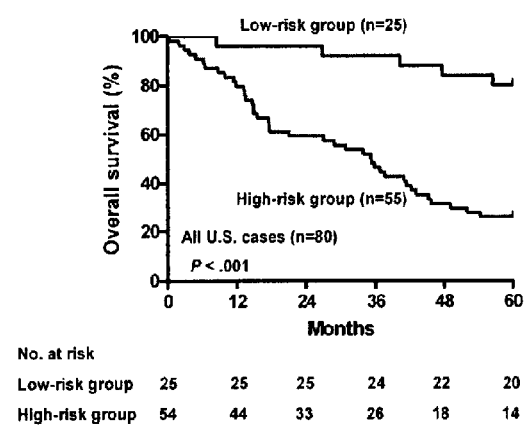
Figure 5D:
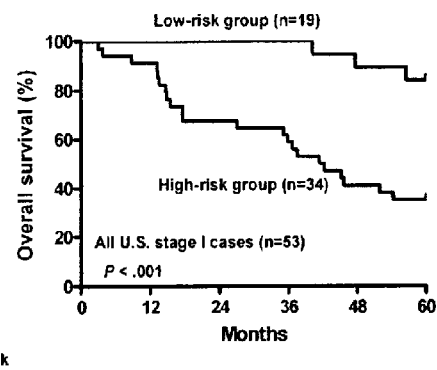

For the 80 U.S. patients, those classified by CLASS-11 as being at high risk of death (n=55) had statistically significantly worse survival than those classified by CLASS-11 as being at low risk of death (n=25) (P<0.001) (FIG. 5C). In addition, among the 53 patients with stage I adenocarcinoma, those classified by CLASS-11 as being at high risk of death (n=34) had statistically significantly worse survival than those classified by CLASS-11 as being at low risk of death (n=19) (P<0.001) (FIG. 5D). Among the stage I patients, the 5-year survival rates were 84% (95% CI=59% to 95%) for those at low risk of death and 35% (95% CI=20% to 51%) for those at high risk of death. Notably, CLASS-11 correctly predicted poor survival in 24 (89%) of the 27 stage I cases in the high risk of death group.

Figure 6A:
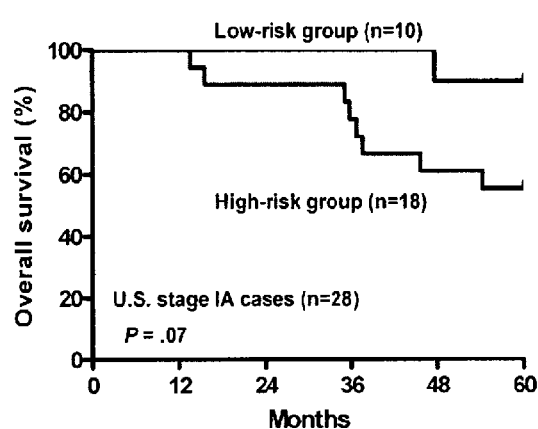
FIGS. 6A-C are graphs showing (A) overall survival among 28 patients with stage IA disease (P=0.07), (B) Kaplan-Meier plots of overall survival of 25 patients with stage IB disease (P<0.001), and (C) Kaplan-Meier plots of overall survival of 20 patients with stage II disease (P=0.01). P-values were calculated by the COX-Mantel log-rank test and statistical significance was considered to be <0.05.
Figure 6B:
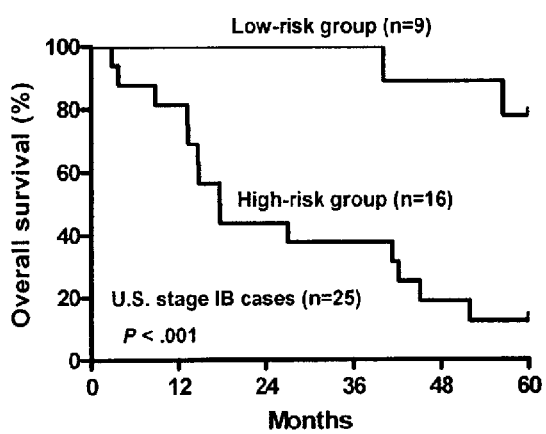
Figure 6C:
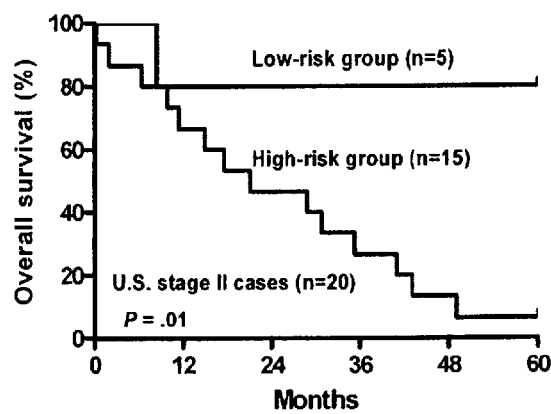

The three cases of bronchioloalveolar adenocarcinoma were excluded from the Kaplan-Meier survival analysis of the stage I cases because this histological subtype can be associated with a more favorable prognosis. Among the remaining stage I patients (n=50), those classified by CLASS-11 as being at high risk of death (n=32) had statistically significantly worse survival than those classified by CLASS-11 as being at low risk of death (n=18) (P<0.001). The prognostic ability of CLASS-11 was also examined for differences with respect to stage. Among patients with stage IA adenocarcinoma (n=28), there was a non-statistically significant difference in survival between the groups at high and low risk of death (P=0.07) (FIG. 6A). Among patients with stage IB (n=25) or stage II (n=20) adenocarcinoma, those classified by CLASS-11 as being at high risk of death had statistically significantly poorer survival than those classified by CLASS-11 as being at low risk of death (P<0.001 and P=0.01, respectively) (FIGS. 6B and 6C).

Whether the prognostic ability of CLASS-11 was affected by underlying clinical covariates was determined by performing univariate and multivariable Cox proportional hazards survival analyses. The univariate analysis of the 80 U.S. patients revealed that TNM stage (hazard ratio [HR] for death in the stage II-IV group compared with the stage I reference group=2.58, 95% CI=1.42 to 4.67; P=0.002) and CLASS-11 prognostic classification (HR for death in the high risk CLASS-11 group compared with the low risk CLASS-11 reference group=6.23, 95% CI=2.44 to 15.86; P<0.001) were both statistically significant predictors of survival (Table 11). The multivariable analysis of the 80 U.S. patients, which adjusted for TNM stage, showed that the CLASS-11 prognostic classification was statistically significantly associated with survival and was an independent prognostic factor for lung adenocarcinoma (HR for death in the high risk CLASS-11 group compared with the low risk CLASS-11 reference group=5.94, 95% CI=2.32 to 15.17; P<0.001).

Univariate and multivariable survival analyses were performed for the 53 stage I patients. The univariate analysis revealed that histologic differentiation (HR for death in the moderate/poorly differentiated group compared with the well-differentiated reference group=3.51, 95% CI=1.05 to 11.74; P=0.04), TNM stage (HR for death in the stage II-IV group compared with the stage I reference group=2.76, 95% CI=1.21 to 6.25; P=0.02), and CLASS-11 prognostic classification (HR for death in the high risk CLASS-11 group compared with the low risk CLASS-11 reference group=6.54, 95% CI=1.95 to 21.96; P=0.002) were statistically significantly associated with survival (Table 11). The multivariable Cox proportional hazards model of all stage I patients, which controlled for race, histologic differentiation, and TNM stage, also revealed that the CLASS-11 prognostic classification was statistically significantly associated with survival and was an independent prognostic factor for stage I cases (HR for death in the high risk CLASS-11 group compared with the low risk CLASS-11 reference group=7.46, 95% CI=2.14 to 26.05; P=0.002).

When the three bronchioloalveolar adenocarcinoma cases were excluded from both the univariate and multivariate analyses, the results remained statistically significant. Therefore, the presence of this histologic subtype did not influence the prediction of survival by CLASS-11. Bronchioloalveolar carcinoma patients been reported to have a favorable prognosis. These results indicate that 5-year overall survival was still statistically significantly different between low-risk and high-risk groups in the 50 U.S. cases without bronchioloalveolar carcinoma.

TABLE 11

Univariate and multivariable Cox proportional hazards models of factors associated w/ death for U.S. and stage I cases*

| Variable | Reference; Comparison | Univariate analysis | | | Multivariable analysis | | |
|---|---|---|---|---|---|---|---|
| | | HR | 95% CI | P† | HR | 95% CI | P† |
| All cases (n = 80) | | | | | | | |
| CLASS-11 | Low risk; High risk | 6.23 | 2.44 to 15.86 | <.001 | 5.94 | 2.32 to 15.17 | <.001 |
| Age | <62 y; ≥62 y | 1.09 | 0.60 to 1.99 | .77 | | | |
| Sex | Male; Female | 0.87 | 0.49 to 1.57 | .65 | | | |
| Race | White; Black | 1.08 | 0.53 to 2.18 | .83 | | | |
| Smoking history | <20 pack-years; ≥20 pack-years | 0.69 | 0.29 to 1.63 | .40 | | | |
| Tumor differentation | Well; Moderate-Poor | 2.06 | 0.96 to 4.43 | .06 | | | |
| TNM stage | I; II-IV | 2.58 | 1.42 to 4.67 | .002 | 2.37 | 1.30 to 4.30 | .005 |
| Stage I cases (n = 53) | | | | | | | |
| CLASS-11 | Low risk; High risk | 6.54 | 1.95 to 21.96 | .002 | 7.46 | 2.14 to 26.05 | .002 |
| Age | <62 y; ≥62 y | 1.11 | 0.50 to 2.44 | .80 | | | |
| Sex | Male; Female | 0.93 | 0.43 to 2.05 | .87 | | | |
| Race | White; Black | 1.32 | 0.55 to 3.16 | .54 | 2.60 | 0.94 to 7.16 | .07 |
| Smoking history | <20 pack-years; ≥20 pack-years | 0.79 | 0.19 to 3.37 | .75 | | | |
| Tumor differentiation | Well; Moderate-Poor | 3.51 | 1.05 to 11.74 | .04 | 1.68 | 0.47 to 5.97 | .42 |
| TNM stage | IA; IB | 2.76 | 1.21 to 6.25 | .02 | 4.58 | 1.79 to 11.71 | .002 |

*HR = hazard ratio; CI = confidence interval; CLASS-11 = Cytokine Lung Adenocarcinoma Survival Signature of 11 genes; TNM = Tumor-Node-Metastasis.
†Two-sided Cox proportional hazards regression using normal approximation.

The inflammatory status of noncancerous tissue surrounding a tumor may play a role in promoting tumor progression and metastasis. Th1 cells produce proinflammatory cytokines (e.g., IL-2, IFN-γ, and TNF-α) as part of the cell-mediated immune response, and Th2 cells regulate humoral immunity by expressing anti-inflammatory cytokines (e.g., IL-4 and IL-10). These results indicate that the propensity of a tumor to metastasize may depend on genetic and epigenetic changes that effect cytokine gene expression in the tumor and on the immunologic status of the patient.

The identification of 11 cytokine markers that are associated with lymph node metastasis of lung cancer patients provides information for future therapies of lung cancer. Long-term survival is associated with the development of cellular immunity and inversely associated with the development of a humoral immune response produced by Th2 cytokines in the regional lymph nodes. Lymphocytic infiltration of primary lung tumor is also associated with lymph node metastasis. It was previously reported that up to one-third of the total tumor infiltrating lymphocyte population in lung tumors are immunosuppressive $CD4^+$ $CD25^+$ regulatory T cells. In addition, the extent of infiltration of these regulatory T cells in the tumor plays a role in the outcome for NSCLC patients. NSCLC cells themselves have been reported to produce as well as to induce Th2 cytokines. Thus, immunohistochemical analysis and laser capture microdissection technique can be used to delineate the roles of various immune cells in contributing to molecular pathogenesis of lung cancer. The information of the immune cells can be useful in stratifying patients for the trials of adjuvant therapy including immunotherapy.

IL-8 and TNFα were the top two genes for predicting prognosis by PAM ranking, and may have angiogenic activities in cancer. Elevated levels of IL-8 and TNFα in tumor tissue from adenocarcinoma patients could enhance angiogenesis and the occurrence of microinvasion. IL-8 (also known as CXCL8) also functions as a positive autocrine growth factor for NSCLC. Consequently, high expression levels of IL-8 and TNFα in tumors may increase tumor growth rate, resulting in poor survival independent of lymph node status.

Example 5

Validation of the CLASS-11 Prognosis Predictor

The robustness of CLASS-11 in classifying patients into prognostic groups in an independent set of tumor and corresponding noncancerous lung tissue samples from 50 Japanese stage I adenocarcinoma patients who had undergone surgical resection from 1999 to 2003.

Figure 5E:
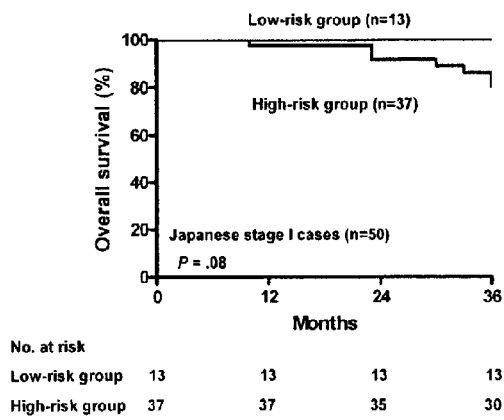
Figure 5F:
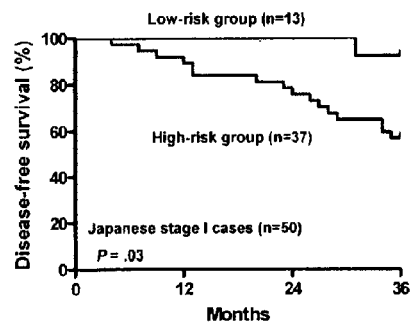

The Japanese and U.S. patients differed from each other in several respects, in particular that there was a higher frequency of heavy smokers (smoking history of 20 or more pack-years) and patients with moderate or poorly differentiated carcinoma among the U.S. patients than among the Japanese patients (P<0.001 and P=0.009, respectively) (Table 5). The CLASS-11 prognostic classifier identified the 50 Japanese cases as high risk of death (n=37 cases) and low risk of death (n=13 cases). The Kaplan-Meier survival curves, stratified by CLASS-11 prognostic classification, are shown in FIGS. 5E and 5F. Although CLASS-11 correctly classified the eight Japanese patients who had died during the 3 years of follow-up as being at high risk of death, there was no statistically significant difference between low-risk and high-risk groups in overall survival, perhaps because of the shorter follow-up period for this cohort (P=0.08; Wilcoxon log-rank test) (FIG. 5E). However, the group classified as being at high risk of death (n=37) had statistically significantly poorer disease-free survival than the group at low risk of death (n=13) (P=0.03; Wilcoxon log-rank test) (FIG. 5F).

These results demonstrate the robustness of CLASS-11, as CLASS-11 was able to predict high-risk of recurrence in Japanese stage I cases. Therefore, CLASS-11 is a unique signature in predicting prognosis of adenocarcinomas.

Example 6

Confirmation of Cytokine Gene Expression by ELISA

This example describes methods used to correlate cytokine mRNA expression as measured by qRT-PCR and cytokine protein expression as measured by ELISA.

Cytokine protein concentrations were measured in pairs of noncancerous tissue and tumor tissue from 30 of the 80 U.S. cases that had tissue available for this analysis. IL-8 protein was detected in all tumor and noncancerous tissues examined (FIG. 7A), whereas five other cytokines (IL-1β, IL-2, IL-10, IFNγ, and TNFα) were not detectable in many of the tissues examined. The tumor tissues expressed statistically significantly higher levels of IL-8 than the noncancerous tissues for tumor versus noncancerous tissue (median IL-8 concentrations): 6.45 pg/mg tissue (interquartile range=1.11 pg/mg to 10.25 pg/mg) versus 1.89 pg/mg tissue (interquartile range=1.19 pg/mg to 4.61 pg/mg), P=0.003, Wilcoxon matched pairs signed-rank test). There was no correlation between IL-8 mRNA expression and IL-8 protein concentration in noncancerous tissue (Spearman's rho=0.10; P=0.59). However, in tumor tissue, IL-8 protein concentration was statistically significantly correlated with IL-8 mRNA expression (Spearman's rho=0.47; P=0.009) (FIG. 7B).

Furthermore, Kaplan-Meier survival analysis of these 30 cases stratified by the median IL-8 concentration in tumor tissue revealed that patients whose tumors expressed IL-8 protein at levels at or greater than the median concentration (n=16) had statistically significantly worse survival than patients whose tumors expressed IL-8 protein at levels below the median (n=14) (P=0.03) (FIG. 7C). Thus, the increased level of IL-8 gene expression in tumor tissue was associated with elevated IL-8 protein concentration in the tumor tissue and with poor overall survival.

Example 7

Exemplary Centroid Values

RNA was isolated from tumor sample (T) and corresponding noncancerous lung sample (N) from same individual. Normal lung tissue pool from 4 cancer-free patients was used as a control (C). Quantitative real time RT-PCR was performed using primers for the 11 cytokines on RNA obtained from the T, N and C samples. Real time quantitative RT-PCR analysis was performed by the Taqman Cytokine Gene Expression Plate (Applied Biosystems). Each column of the plate contained primers and probes of 11 cytokine genes (FAM dye layers) and 18SrRNA endogenous control (VIC dye layers).

The raw qRT-PCR values were calculated. The ratio of abundance in each tissue sample (T and N) compared with control (C) was used for statistical analyses. After qRT-PCR, two raw data of Ct value was obtained. The quantification of gene expression was calculated using the comparative (ΔΔCT) method, as previously described (Bustin, *J. Mol. Endocrinol.* 25:169-93, 2000, incorporated by reference).
For example:
T(ΔCT)=IL-10Ct 32, 18SrRNACt 15
N(ΔCT)=IL-10Ct 33, 18SrRNACt 15

The normal tissue pool from four cancer-free patients was used as a normal control (C). For example: C(ΔCT)=IL-10Ct 30, 18SrRNACt 15

Relative ratio was calculated as follows: T(ΔΔCT)=T(ΔCT)−C(ΔCT)=(TCt-18SrRNA)−(C Ct-18SrRNA)=(32-15)−(30-15)=2

$2^{(-\Delta\Delta CT)}$=0.25(=Raw data)

N(ΔΔCT)=N(ΔCT)−C(ΔCT)=(TCt-18SrRNA)−(C Ct-18SrRNA)=(33-15)−(30-15)=3

$2^{(-\Delta\Delta CT)}$=0.125(=Raw data)

The centroid values obtained are shown below:

| | Tissue | | | |
| --- | --- | --- | --- | --- |
| | Noncancerous tissue | | Tumor tissue | |
| | Prediction | | | |
| | Lymph node status | | Prognosis | |
| PAM outcome | NON | MET | GOOD | POOR |
| IL-1a | −0.08 | 0.19 | −0.17 | 0.13 |
| IL-1b | −0.07 | 0.16 | −0.22 | 0.17 |
| IL-2 | −0.08 | 0.17 | −0.19 | 0.13 |
| IL-6 | −0.08 | 0.20 | −0.10 | 0.07 |
| IL-8 | −0.11 | 0.26 | −0.28 | 0.20 |
| IL-10 | −0.14 | 0.33 | −0.21 | 0.16 |
| IL-12p35 | −0.05 | 0.12 | −0.19 | 0.14 |
| IL-15 | −0.06 | 0.16 | −0.17 | 0.13 |
| CSF-1 | 0.04 | −0.10 | −0.09 | 0.07 |
| IFNr | −0.07 | 0.17 | −0.26 | 0.20 |
| TNFa | −0.07 | 0.16 | −0.27 | 0.20 |

MET: Lymph node positive
NON: Lymph node negative
POOR: <5-year survival
GOOD: >5-year survival

Example 8

Determining Prognosis of a Subject with Adenocarcinoma using CLASS-11

This example provides an exemplary protocol for determining the prognosis of a subject having an adenocarcinoma. As shown in the Examples above, the 11 cytokine gene expression signature of noncancerous lung tissue and corresponding tumor tissue in adenocarcinoma predicts metastasis and disease progression. The CLASS-11 algorithm, which was based on the gene expression profiles of both noncancerous and tumor tissue, identified stage I adenocarcinoma patients who are at high risk of death.

Expression of IL-1a, IL-1b, IL-2, IL-6, IL-8, IL-10, IL-12, IL-15, CSF-1, IFN-γ and TNF-a is determined in a noncancerous sample and an adenocarcinoma sample from the same mammalian subject, such as a human or veterinary subject. In some examples the subject has a stage I, IB, II, or III adenocarcinoma. For example, such samples can be obtained during a tumor biopsy. RNA can be isolated from the samples using a commercial kit, and subjected to quantitative real time RT-PCR to quantitate expression of the 11 cytokines. However, one skilled in the art will appreciate that other expression detection systems can be used, and that cytokine proteins can be evaluated instead of or in addition to cytokine nucleic acid molecules.

The resulting raw values for the 11 cytokines in the non-cancerous sample and the tumor sample are analyzed using PAM and the raw values for known subjects shown in Tables 1 and 2, respectively. If desired, the raw values can be normalized to expression values obtained for the 11 cytokines obtained from normal tissue from the same organ (e.g. sample obtained from a cancer-free subject). In such an example, the resulting normalized values for the 11 cytokines in the non-cancerous sample and the tumor sample are analyzed using PAM and the normalized values for known subjects shown in Tables 3 and 4, respectively.

In some examples, the subject's classification is used by a clinician to select an appropriate anti-tumor therapy. For example, if the subject is classified as having a low risk of death, a less aggressive therapy can be selected. In contrast, if the subject is classified as having a high risk of death, a more aggressive therapy (such as adjuvant chemotherapy) can be selected. For example, use of CLASS-11 can be used for predicting which stage IB and II patients are at high risk of death and who thus may therefore benefit from adjuvant therapy. This signature could improve the selection of lung cancer cases for adjuvant therapy after surgery, resulting in the improvement of 5-year survival.

Example 9

Exemplary Method for Classification of Adenocarcinoma

This example describes methods that can be used to classify an adenocarcinoma using cytokine expression values.

Figure 8:
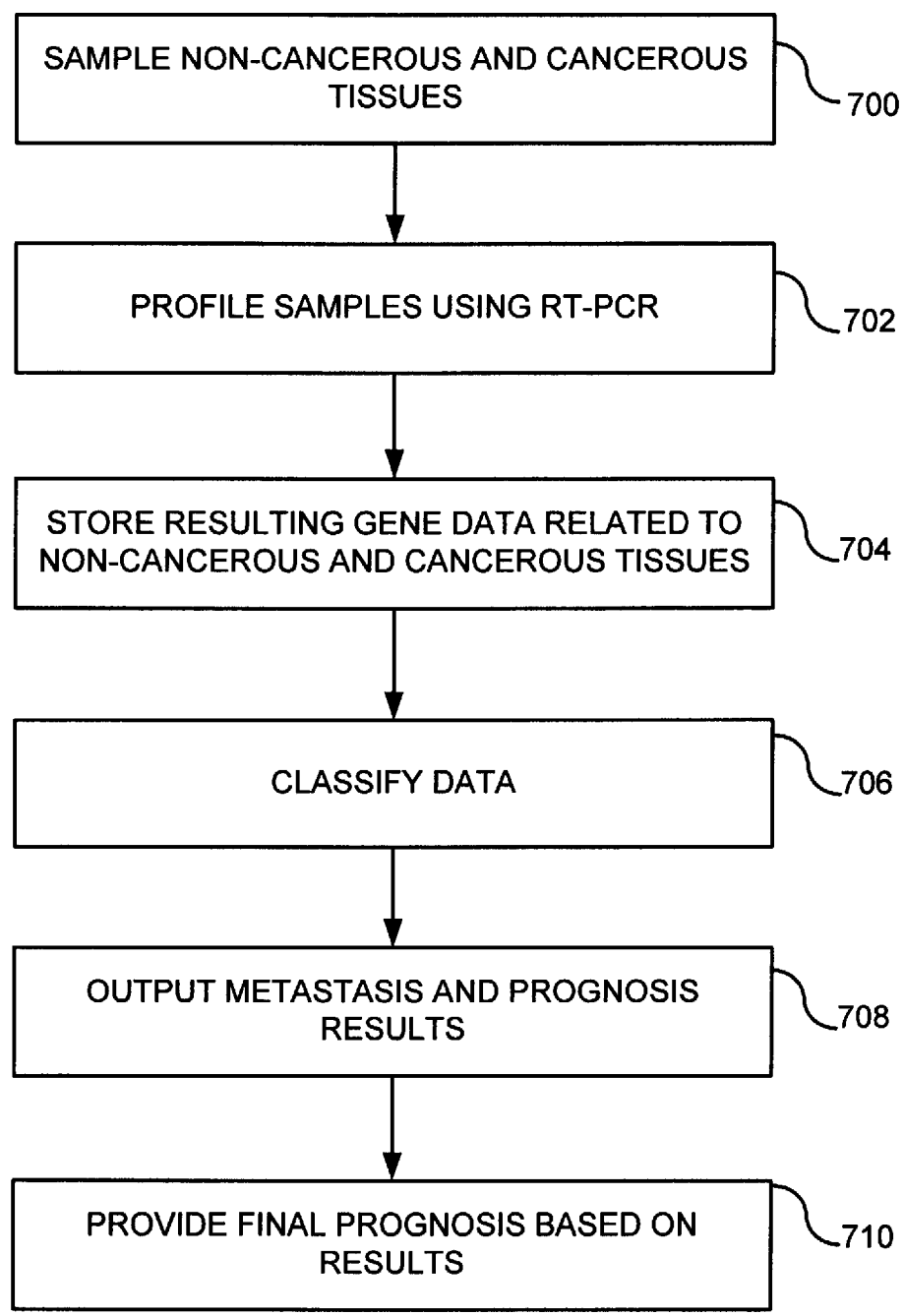
FIG. 8 is a flowchart of a method for diagnosing a patient using class prediction software on an input sample gene expression.

FIG. 8 is a flowchart of a method for classifying non-cancerous and cancerous tissues. In process block 700, samples of both cancerous tissue (adenocarcinoma) and non-cancerous tissue are obtained from the same patient. In process block 702, the samples are profiled by detecting expression of the 11 cytokines as described herein. In process block 704, the resulting gene expression data for non-cancerous and tumor samples are stored. In some examples, such stored data is raw expression data, or expression data normalized to a normal control sample (e.g. from the same organ from a cancer-free subject). For example, the gene expression data can be stored in one or more tables, such as a spreadsheet. In process block 706, the stored gene expression data are input into a classifier that classifies the data and outputs metastasis and prognosis results (process block 708). For example, the results could indicate whether a tumor has metastasized or not and whether the prognosis for the patient is favorable or unfavorable. In process block 710, the final prognosis is provided based on the metastasis and prognosis results results. Generally, if the results indicate the tumor metastasized, the prognosis is poor, or both, the final prognosis is a high risk of death (see FIG. 1B). In contrast, if the results indicate both that the tumor has not metastasized and the prognosis is good, the final prognosis is a low risk of death (see FIG. 1B).

FIG. 9 is a flowchart providing further details of the data classification (e.g., process block 706). Generally, the classification is performed using a linear classifier, but other classifiers may be used. One example classifier is the Prediction Analysis for Microarrays (PAM), which performs class prediction and survival analysis for genomic expressions and is publicly available through Stanford University (see Tibshirani et al., Proc Natl. Acad. Sci. 99:6567-72, 2002). In process block 800, the cytokine expression data for the adenocarcinoma and non-cancerous samples (raw or normalized) are inputted into the classifier. In process block 802, classification tables for gene expressions of known cases (for non-cancerous and tumor samples) is also inputted into the classifier (e.g. Tables 1 and 2 or Table 3 and 4). In process block 804, centroids are generated using the classification tables. As is well understood in the art, a centroid is substantially the average of multiple points in three-dimensional space. In this particular example, there are four centroids and each centroid is assigned a classification, such as metastasis, non metastasis, good prognosis or bad prognosis. In process block 806, a comparison is performed between the non-cancerous sample and the centroids and between the tumor sample and the centroids. In process block 808, the subject is classified by determining which centroid is closest to the samples. This is typically accomplished by computing the squared distance from the sample to each centroid. The centroid that is the closest to the sample determines the sample's classification as it will be assigned the same classification as that centroid.

Example 10

Arrays for Detecting Cytokines

This example describes particular arrays that can be used to evaluate cytokine expression, for example to prognose an adenocarcinoma. When describing an array that consists essentially of probes or primers specific for IL-1a, IL-1b, IL-2, IL-6, IL-8, IL-10, IL-12, IL-15, CSF-1, IFN-γ and TNF-a, such an array includes probes or primers specific for these 11 cytokines, and can further include control probes (for example to confirm the incubation conditions are sufficient), 1-6 additional cytokines, but not other probes. Exemplary control probes include GAPDH, actin, and YWHAZ. In one example, an array is a multi-well plate (e.g. 98 or 364 well plate).

In one example, the array includes, consists essentially of, or consists of probes or primers (such as an oligonucleotide or antibody) that can recognize IL-1a, IL-1b, IL-2, IL-6, IL-8, IL-10, IL-12, IL-15, CSF-1, IFN-γ and TNF-a. The oligonucleotide probes or primers can further include one or more detectable labels, to permit detection of hybridization signals between the probe and target sequence (such as one of the 11 cytokines disclosed herein).

Array Substrate

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoride, polyfluoroethylene-propylene, polyethylenevinyl alcohol, polymethylpentene, polychlorotrifluoroethylene, polysulformes, hydroxylated biaxially oriented polypropylene, animated biaxially oriented polypropylene, thiolated biaxially oriented polypropylene, etyleneacrylic acid, ethylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material animated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g. multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

Example 11

Quantitative Spectroscopic Methods

This example describes quantitative spectroscopic approaches methods, such as SELDI, that can be used to analyze a biological sample to detect and quantitate expression of IL-1a, IL-1b, IL-2, IL-6, IL-8, IL-10, IL-12, IL-15, CSF-1, IFN-γ and TNF-a proteins.

In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as cytokine proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as cytokine proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind at least IL-1a, IL-1b, IL-2, IL-6, IL-8, IL-10, IL-12, IL-15, CSF-1, IFN-γ and TNF-a. In one example, antibodies are immobilized onto the surface using a bacterial Fc binding support. The chromatographic surface is incubated with a sample from the subject, such as a non-cancerous sample and a tumor sample. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

Example 12

Kits

Kits are provided for evaluating an adenocarcinoma, for example for determining the prognosis of a subject having an adenocarcinoma, and determining a treatment regimen for a subject who has adenocarcinoma. The kits can be used to detect expression of IL-1a, IL-1b, IL-2, IL-6, IL-8, IL-10, IL-12, IL-15, CSF-1, IFN-γ and TNF-a nucleic acids (such as mRNA) or proteins (such as kits containing nucleic acid probes, proteins, antibodies, or other protein specific binding agents).

Kits can include reagents needed to detect IL-1a, IL-1b, IL-2, IL-6, IL-8, IL-10, IL-12, IL-15, CSF-1, IFN-γ and TNF-a nucleic acids or proteins on an array. These kits can each include instructions, for instance instructions that provide raw or normal cytokine expression data for known adenocarcinoma cases (e.g. Tables 1-2 or 3-4).

Kits are provided that permit detection of cytokine mRNA expression levels. Such kits include an appropriate amount of one or more of the oligonucleotide primers for use in, for instance, real time RT-PCR reactions, and can also include reagents necessary to carry out real time RT-PCR or other in vitro amplification reactions, including, for instance, RNA sample preparation reagents (such as an RNAse inhibitor), appropriate buffers (such as polymerase buffer), salts (such as magnesium chloride), and deoxyribonucleotides (dNTPs).

In examples of such a kit, an appropriate amount of oligonucleotide primers specific for sequences consisting essentially of or consisting of IL-1a, IL-1b, IL-2, IL-6, IL-8, IL-10, IL-12, IL-15, CSF-1, IFN-γ and TNF-a is provided in one or more containers. A kit can include more than two primers to facilitate the in vitro amplification of sequences consisting of or consisting essentially of IL-1a, IL-1b, IL-2, IL-6, IL-8, IL-10, IL-12, IL-15, CSF-1, IFN-γ and TNF-a. The oligonucleotide primers or probes can be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers are provided in pre-measured single use amounts in individual, typically disposable, tubes, or equivalent containers. With such an arrangement, the sample to be assayed can be added to the individual tubes and in vitro amplification carried out directly.

The amount of each primer supplied in the kit can be any amount, depending for instance on the market to which the product is directed. For instance, if the kit is adapted for research or clinical use, the amount of each oligonucleotide primer provided is likely an amount sufficient to prime several in vitro amplification reactions. Those of ordinary skill in the art know the amount of oligonucleotide primer that is appropriate for use in a single amplification reaction. General guidelines can be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, New York, 1989), and Ausubel et al. (In *Current Protocols in Molecular Biology*, John Wiley & Sons, New York, 1998).

In some examples, kits also include the reagents needed to perform in vitro amplification reactions, such as DNA sample preparation reagents, appropriate buffers (for example polymerase buffer), salts (for example magnesium chloride), and deoxyribonucleotides (dNTPs). Written instructions can also be included. Kits can further include labeled or unlabeled oligonucleotide probes to detect the in vitro amplified sequences (amplicons). The appropriate sequences for such a probe will be any sequence that falls between the annealing sites of two provided oligonucleotide primers, such that the sequence the probe is complementary to is amplified during the in vitro amplification reaction (if it is present in the sample).

One or more control sequences can be included in the kit for use in the in vitro amplification reactions. The design of appropriate positive and negative control sequences is well known to one of ordinary skill in the art.

In some examples, kits are provided with the reagents needed to perform quantitative or semi-quantitative Northern analysis of cytokine mRNA. Such kits can include oligonucleotides for use as probes for IL-1a, IL-1b, IL-2, IL-6, IL-8, IL-10, IL-12, IL-15, CSF-1, IFN-γ and TNF-a.

Probes or primers in the kit can be labeled, for example with a radioactive isotope, enzyme substrate, co-factor, ligand, chemiluminescent or fluorescent agent, hapten, or enzyme.

In particular examples, a kit includes one or more of the detection arrays disclosed herein (such as those disclosed in Example 10). In one example, the array consists essentially of probes that can detect IL-1a, IL-1b, IL-2, IL-6, IL-8, IL-10, IL-12, IL-15, CSF-1, IFN-γ and TNF-a, and control probes (such as GAPDH, actin, and YWHAZ), 1-6 additional cytokines, or combinations thereof. Probes that recognize the cytokines and control sequences (such as negative and positive controls) can be on the same array, or on different arrays.

Kits are also provided for the detection of cytokine protein expression, for instance increased expression of proteins consisting of or consisting essentially of IL-1a, IL-1b, IL-2, IL-6, IL-8, IL-10, IL-12, IL-15, CSF-1, IFN-γ and TNF-a. Such kits can include cytokine specific binding agents (such as a polyclonal or monoclonal antibody or antibody fragment), and can include at least one control. The cytokine protein specific binding agent and control can be contained in separate containers. The kits can also include agents for detecting cytokine protein:agent complexes, for instance the agent can be detectably labeled. If the detectable agent is not labeled, it can be detected by second antibodies or protein A, for example, either of both of which also can be provided in some kits in one or more separate containers. Such techniques are well known.

Additional components in some kits include instructions for carrying out the assay, which can include reference values (e.g. control values, such as those in Tables 1-4). Instructions can also permit the tester to determine whether detected cytokine expression levels are elevated, reduced, or unchanged in comparison to a control sample. Reaction vessels and auxiliary reagents such as chromogens, buffers, enzymes, and the like can also be included in the kits.

It will be apparent that the precise details of the methods or arrays described may be varied or modified without departing from the spirit of the described invention. We claim all such modifications and variations that fall within the scope and spirit of the claims below.

We claim:

1. A method for treating a subject with a stage I, IB, or II lung adenocarcinoma, comprising:
    contacting a stage I, IB, or II lung adenocarcinoma sample obtained from the subject with nucleic acid probes and/or nucleic acid primers specific for cytokines consisting of interleukin (IL)-1a, IL-1b, IL-2, IL-6, IL-8, IL-10, IL-12, IL-15, colony stimulating factor (CSF)-1, interferon (IFN)-γ, and tumor necrosis factor (TNF)-a;
    measuring
        (a) increased nucleic acid expression of cytokines consisting of IL-1a, IL-8, and TNF-a in the stage I, IB, or II lung adenocarcinoma as compared to a control comprising values for IL-1a, IL-1b, IL-2, IL-6, IL-8, IL-10, IL-12, IL-15, CSF-1, IFN-γ, and TNF-a nucleic acid expression for a subject without lung adenocarcinoma, or
        (b) increased nucleic acid expression of cytokines consisting of IL-1a, IL-1b, IL-2, IL-6, IL-8, IL-10, IL-12, IL-15, TNF-a, CSF-1 and IFN-γ in the stage I, IB, or II lung adenocarcinoma as compared to the control; and
    administering chemotherapy or radiation to the subject following surgical resection of the lung adenocarcinoma, thereby treating the subject.

2. The method of claim 1, wherein the control is a centroid value for expression of IL-1a, IL-1b, IL-2, IL-6, IL-8, IL-10, IL-12, IL-15, CSF-1, IFN-γ and TNF-a in a subject that is cancer-free in the lung.

3. The method of claim 1, further comprising staging the adenocarcinoma using clinical parameters.

4. The method of claim 1, wherein measuring increased nucleic acid expression of IL-1a, IL-1b, IL-2, IL-6, IL-8, IL-10, IL-12, IL-15, CSF-1, IFN-γ and TNF-a as compared to the control comprises the use of a shrunken centroid calculation.

5. The method of claim 4, wherein the shrunken centroid calculation comprises the use of a prediction analysis of microarrays (PAM).

6. The method of claim 1, wherein measuring increased nucleic acid expression comprises:
    generating centroids; and
    comparing the adenocarcinoma tissue expression values to the centroids and comparing the non-cancerous lung tissue values to the centroids.

7. The method of claim 1, wherein the subject is a mammal.

8. The method of claim 7, wherein the mammal is a human.

9. The method of claim 1, wherein the control comprises lung tissue from a subject that has not been diagnosed with lung adenocarcinoma.

10. The method of claim 1, wherein the control comprises lung tissue from a subject that has not be diagnosed with any cancer.

11. The method of claim 1, wherein the chemotherapy comprises carboplatin or cis-platinum.

12. The method of claim 1, wherein the chemotherapy comprises 5-fluorouracil (5-FU), azathioprine, cyclophosphamide, an antimetabolite, an antineoplastic, carboplatin, cis-platinum or a taxane.

13. A method for treating an individual of interest with a lung adenocarcinoma, comprising,
    contacting a plurality of lung adenocarcinoma samples from subjects with known prognosis and metastasis status with nucleic acid probes and/or nucleic acid primers specific for cytokines consisting of interleukin (IL)-1a, IL-1b, IL-2, IL-6, IL-8, IL-10, IL-12, IL-15, colony stimulating factor (CSF)-1, interferon (IFN)-γ, and tumor necrosis factor (TNF)-a;
    contacting a plurality of non-cancerous lung tissue samples with nucleic acid probes and/or nucleic acid primers specific for cytokines consisting of IL-1a, IL-1b, IL-2, IL-6, IL-8, IL-10, IL-12, IL-15, CSF-1, IFN-γ, and TNF-a;
    measuring mRNA expression of cytokines consisting of IL-1a, IL-1b, IL-2, IL-6, IL-8, IL-10, IL-12, IL-15, CSF-1, IFN-γ and TNF-a in the plurality of lung adenocarcinoma samples and in the plurality of non-cancerous lung samples;
    using a statistical method to evaluate the centroid values of IL-1a, IL-1b, IL-2, IL-6, IL-8, IL-10, IL-12, IL-15, CSF-1, IFN-γ, TNF-a in the plurality of lung adenocarcinoma samples and in the plurality of non-cancerous lung samples;
    measuring mRNA expression of IL-1a, IL-1b, IL-2, IL-6, IL-8, IL-10, IL-12, IL-15, CSF-1, IFN-γ, TNF-a in a sample of lung adenocarcinoma k the individual of interest;
    comparing the mRNA expression of IL-1a, IL-1b, IL-2, IL-6, IL-8, IL-10, IL-12, IL-15, CSF-1, IFN-γ, TNF-a a in the lung adenocarcinoma sample from the individual of interest as compared to the centroid values for the plurality of non-cancerous lung samples;
    measuring
        (a) increased mRNA expression of cytokines consisting of IL-1a, IL-8, TNF-a in the lung adenocarcinoma sample from the individual of interest as compared to the centroid values for the plurality of non-cancerous lung samples, or
        (b) increased mRNA expression of cytokines consisting of IL-1a, IL-1b, IL-2, IL-6, IL-8, IL-10, IL-12, IL-15, TNF-a, CSF-1 and IFN-γ in the lung adenocarcinoma sample from the individual of interest as compared to the centroid values for the plurality of non-cancerous lung samples; and administering chemotherapy or radiation to the individual of interest following surgical resection of the lung adenocarcinoma, thereby treating the individual of interest.

14. The method of claim 13, wherein the individual of interest is a mammal.

15. The method of claim 14, wherein the mammal is a human.

16. The method of claim 13, wherein the chemotherapy comprises carboplatin or cis-platinum.

17. The method of claim 13, wherein the chemotherapy comprises 5-fluorouracil (5-FU), azathioprine, cyclophosphamide, an antimetabolite, an antineoplastic, carboplatin, cis-platinum or a taxane.

* * * * *